(12) United States Patent
Li et al.

(10) Patent No.: US 9,550,741 B2
(45) Date of Patent: Jan. 24, 2017

(54) BENZOISOTHIAZOLE COMPOUNDS AND METHODS OF TREATING SCHIZOPHRENIA

(71) Applicant: SHANGHAI INSTITUTE OF PHARMACEUTICAL INDUSTRY, Shanghai (CN)

(72) Inventors: Jianqi Li, Shanghai (CN); Xiaowen Chen, Shanghai (CN); Zhilong Ma, Shanghai (CN); Li Zhang, Shanghai (CN); Ning Cui, Shanghai (CN)

(73) Assignee: Shanghai Institute of Pharmaceutical Industry, Shanghai (CN)

( * ) Notice: Subject to any disclaimer, the term of this patent is extended or adjusted under 35 U.S.C. 154(b) by 0 days.

(21) Appl. No.: 14/889,831

(22) PCT Filed: May 8, 2014

(86) PCT No.: PCT/CN2014/000474
§ 371 (c)(1),
(2) Date: Nov. 6, 2015

(87) PCT Pub. No.: WO2014/180165
PCT Pub. Date: Nov. 13, 2014

(65) Prior Publication Data
US 2016/0096811 A1   Apr. 7, 2016

(30) Foreign Application Priority Data
May 8, 2013   (CN) .......................... 2013 1 0166896

(51) Int. Cl.
*C07D 417/12*   (2006.01)
*A61K 31/496*   (2006.01)
*C07D 275/04*   (2006.01)

(52) U.S. Cl.
CPC ........... *C07D 275/04* (2013.01); *C07D 417/12* (2013.01)

(58) Field of Classification Search
None
See application file for complete search history.

(56) References Cited

FOREIGN PATENT DOCUMENTS

| | | |
|---|---|---|
| CN | 102947310 A | 2/2013 |
| CN | 103130737 A | 6/2013 |
| WO | WO 2006/082456 A1 | 8/2006 |
| WO | WO 2010031735 A1 | 3/2010 |
| WO | WO 2010/034646 A1 | 4/2010 |
| WO | WO 2012/117001 A1 | 9/2012 |

OTHER PUBLICATIONS

Toru et al., "Creativity in the Development of the Drug, Aripiprazole: A Novel Partial Dopamine $D_2$ Receptor Agonist for the Treatment of Schizophrenia", Seishin-Igaku, (Psychiatry), vol. 46, pp. 855-864, (2004).*
Li et al. Partial Translation for CN103130737 (Jun. 5, 2013) pp. 1-11 only provided.*
WIPO, PCT/CN2014/000474, International Search Report, Jul. 30, 2014, 13 pgs.

* cited by examiner

*Primary Examiner* — Emily Bernhardt
(74) *Attorney, Agent, or Firm* — Haynes and Boone, LLP

(57) ABSTRACT

Disclosed are benzoisothiazole compounds and a use in the preparation of anti-schizophrenia drugs. The benzoisothiazole compounds of the present invention not only have strong affinity for dopamine $D_3$ receptor, $5-HT_{1A}$ receptor and $5-HT_{2A}$ receptor, but also can observably improve the symptoms of schizophrenia relevant to apomorphine model and MK-801 model mice, with oral absorption being good, safety being high and side-effect being less, and having developmental value as new anti-neurotic disease drugs. The present invention is the compounds having a structure of general formula (I), or geometric isomers, free alkalies, salts, hydrates or solvates thereof.

12 Claims, No Drawings

BENZOISOTHIAZOLE COMPOUNDS AND METHODS OF TREATING SCHIZOPHRENIA

CROSS-REFERENCE TO RELATED APPLICATIONS

This is the national stage of PCT/CN2014/000474, filed May 8, 2014, which claims the benefit of CN201310166896.6, filed May 8, 2013, the contents of each of which are hereby incorporated herein in its entirety by express reference thereto.

TECHNICAL FIELD

The present invention relates to benzoisothiazole compounds with antipsychotic activities and its use as anti-schizophrenia drugs.

BACKGROUND ART

Psychotic diseases include anxiety, schizophrenia, dipolar disorder, etc. Schizophrenia is the most serious and harmful one among the psychotic diseases, and it is the seventh disease which contributes to the society burden. Its main clinical manifestation comprises thought disorder (thought broadcasting, thought withdrawal, thought poverty, delusion, etc.), hallucination, mood disorder (abepithymia, parathymia), behavior disorder (social withdrawal, bizarre behavior, catatonic excitement, stupor, etc.) and learning and working memory deficits. With the deterioration of social environment and the increasing life stress, the incidence of schizophrenia shows a clear upward trend.

In modern medicine, schizophrenia is considered as a syndrome, a collection of symptoms and signs with unclear causes. In the recent decade, the researches on neurotransmitters and receptors are active, and it is found that in some of the schizophrenic patients, the neuroendocrine is affected due to central neurotransmitter and receptor dysfunction. The above research result is used in clinic and for developing novel therapeutic drugs. Numerous researches show that psychotic diseases are associated with central monoamine neurotransmitter and receptor dysfunction, and the central dopamine (DA) system and 5-hydroxyl tryptamine (5-HT) system are closely related with the human psychomotility. Studies show that DA and 5-HT system dysfunction may lead to multiple neuropsychiatric diseases such as schizophrenia, depression, mania, anxiety, Parkinson's disease, neuropathic pain, etc.

At present, clinically available antipsychotic drugs mainly act on DA and 5-HT systems, which can be divided into classical antipsychotics and non-classical antipsychotics based on their mechanisms and targets. The former mainly acts on DA system ($D_2$ receptor antagonist), while the latter mainly acts on DA system and 5-HT system (for example, $D_2$/5-$HT_{2a}$ dual antagonist). The current first-line drugs in clinic are mainly non-classical antipsychotics. The classical antipsychotics may lead to side effects such as extrapyramidal system effect (EPS) and byperprolactinemia, etc. due to their superantagonism toward substantia nigra-striatum and tubero-infundibular $D_2$ receptor. In addition, since they act on DA system alone, they are only effective for schizophrenic positive symptoms, and are ineffective for negative symptoms and cognitive impairment. Non-classical antipsychotics such as ziprasidone, risperidone, aripiprazole, quetiapine, etc. which can be used to treat positive symptoms also show some improvement effect on negative symptoms, although they cannot significantly improve cognitive impairment. All of them show corresponding side effects, such as higher EPS probability, obesity, akathisia, insomnia, anxiety, cardiotoxicity, etc. Therefore, there are no currently marketed drugs which can effectively reduce the above side effects while improving the whole spectrum of schizophrenia. Thus, the focus in developing antipsychotic drugs is to look for novel anti-schizophrenia drugs with high efficacy, low toxicity and wide treatment spectrum.

Five subtypes of dopamine receptors $D_1$, $D_2$, $D_3$, $D_4$ and Dg belong to two families, i.e. $D_1$ family, which includes $D_1$ and $D_5$, and $D_2$ family, which includes $D_2$, $D_3$ and $D_4$. Currently, more researches are focused on $D_2$ receptor family. $D_2$ receptor in central system is mainly distributed in substantia nigra, corpus striatum, caudate nucleus, nucleus accumbens and limbic system. Existing antipsychotics exert their anti-schizophrenic positive symptom effect by antagonizing the $D_2$ receptor. $D_3$ receptor shows high homology to $D_2$ receptor. Intracerebral $D_3$ receptor is mainly distributed in mesencephalon cortex and limbic system. Blockage of $D_3$ receptor will eliminate side effects such as extrapyramidal system (EPS) effect and the like, and is useful in treating catalepsy and improving cognition function in patients. Thus, a $D_3$ receptor-selective antagonist has a favorable application prospect as an anti-schizophrenia drug. However, $D_3$ receptor mRNA shows less distribution in the brain than $D_2$ receptor. Thus, it is required that the drugs should possess $D_3$ receptor selectivity when acting on $D_2$ and $D_3$ receptors both, that is to say, the drugs should possess 10 folds or higher affinity to $D_3$ receptor than to $D_2$ receptor so as to exert physiological effects on catalepsy, cognition improvement and the like. Numerous researches show that 5-$HT_{2A}$ receptor antagonists can remove the inhibition of dopaminergic neurons in limbic system to restore the normal function of dopaminergic neurons and thereby to improve the negative symptoms.

In recent years, the improvement effect of 5-$HT_{1A}$ receptor for reducing side effects of anti-schizophrenia drugs and improving cognition function has been gradually recognized in the academic community. It is demonstrated that the activation (or partial activation) of 5-$HT_{1A}$ can effectively reduce EPS and other side effects caused by excessive $D_2$ blockage; in prefrontal cortex, NMDA (N-methyl-D-aspartic acid) receptor channel shares the same target as 5-$HT_{1A}$ receptor, and thus the action on 5-$HT_{1A}$ receptor in prefrontal cortex may facilitate the improvement of cognition function; and the activation of postsynaptic 5-$HT_{1A}$ receptor may reduce the release of glutamic acid, which helps to improve negative symptoms and cognition function. The partial activation of 5-$HT_{1A}$ and the synergism with $D_3$ can reduce EPS below the observable level at therapeutic dosages. Therefore, novel anti-schizophrenia drugs which act on $D_2$, $D_3$, 5-$HT_{1A}$ and 5-$HT_{2A}$ receptor simultaneously and possess $D_3$ selectivity have become a new direction in developing anti-schizophrenia drugs at present, and offer a guideline for the development of drugs for treating relevant diseases.

Cariprazine (RGH-188, with its chemical structure shown below) is a partial agonist of $D_2$/$D_{3/5}$-$HT_{1A}$ receptor jointly developed by Forest Laboratories and Gedeon Richter, which has passed Phase III clinical trial in USA, and now is at the registration stage. Its indications include schizophrenia, mania and depression. It is demonstrated by the results of receptor affinity tests that Cariprazine shows strong affinity to $D_2$, $D_3$ and 5-$HT_{1A}$ receptors (with the Ki values of 0.69 nM, 0.085 nM and 2.46 nM, respectively), moderate affinity to 5-$HT_{2A}$ receptor (with the Ki value of 19 nM), and a certain degree of $D_3$/$D_2$ receptor selectivity. In vivo tests demonstrates that it shows a clear efficacy with low toxicity and is unlikely to cause weight gain in patients of schizophrenia, depression and mania. It is further demonstrated by the clinical trials that Cariprazine shows good efficacy in treating manic depression. If it is successfully approved for the market, single drug treatment for manic depression will be realized for the first time, which will improve the compliance of the patients, and avoid the combination administration of anti-schizophrenia drugs and anti-depression drugs.

However, it is further demonstrated by the clinical trials that 22% of the patients who received Cariprazine at doses of 3 mg/d and 4.5 mg/d suffer from EPS, probably due to the excessively strong affinity to $D_2$ receptor and the excessive blockage, or alternatively, due to that the effect on $5\text{-}HT_{1A}$ receptor fails to completely improve the excessive blockage of $D_2$ receptor. In animal experiments, Cariprazine shows good improvement effect on cognitive impairment, which, however, is not clearly demonstrated in clinical patients. This may be probably due to that the $D_3/D_2$ receptor selectivity is still insufficient to exhibit the improvement effect on $D_3$ receptor-mediated cognition function.

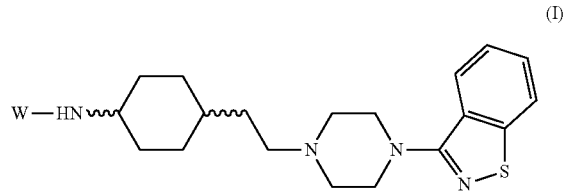

(I)

Chemical Structure of Cariprazine

SUMMARY OF THE INVENTION

The first technical problem to be solved by the present invention is to disclose a benzoisothiazole compound for overcoming the side effects of the existing drugs, for example akathisia, EPS, catalepsy, etc., and defects such as poor efficacy in treating cognitive impairment, etc., so as to meet the demand for clinical use.

The second technical problem to be solved by the present invention is to disclose the use of the above compound in preparation of a medicament for treating schizophrenia and relevant neuropsychiatric diseases.

The benzoisothiazole compound according to the present invention is a compound having the structure of general formula (I) or the geometric isomers, free alkalies, salts, hydrates or solvates thereof:

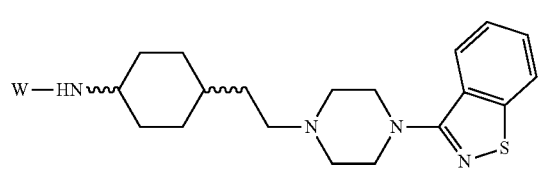

(I)

wherein:
W is:

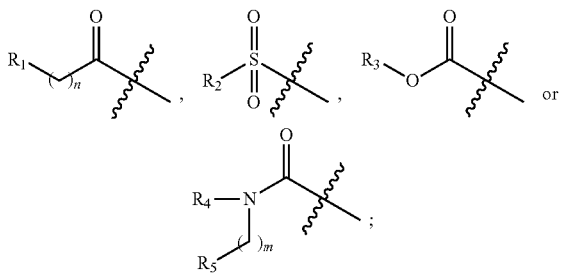

$R_1$ and $R_2$ independently represent heteroaryl or substituted heteroaryl;
n is 0, 1, 2 or 3, preferably 0 or 1;
m is 0, 1 or 2, preferably 0 or 1;
$R_3$ represents $C_1\text{-}C_4$ alkyl, substituted $C_1\text{-}C_4$ alkyl, $C_3\text{-}C_6$ cycloalkyl, substituted $C_3\text{-}C_6$ cycloalkyl, phenyl, substituted phenyl, benzyl, substituted benzyl, heteroaryl, substituted heteroaryl, heteroarylmethyl, or substituted heteroarylmethyl;
$R_4$ is hydrogen atom or $C_1\text{-}C_4$ alkyl;
$R_5$ is phenyl, substituted phenyl, heteroaryl or substituted heteroaryl; wherein the heteroaryl represented by $R_1$ and $R_2$ is selected from furyl, pyrrolyl, thienyl, benzofuryl, indolyl or benzothienyl;
the substituent of the substituted heteroaryl represented by $R_1$ and $R_2$ is selected from halogen, cyano, $C_1\text{-}C_2$ alkyl carbonyl, nitro, methoxyl or $C_1\text{-}C_4$ alkyl;
the $C_1\text{-}C_4$ alkyl represented by $R_3$ can be substituted by 1-3 fluorine atom(s);
the substituent of the substituted cycloalkyl represented by $R_3$ is selected from $C_1\text{-}C_2$ alkyl;
the substituent of the substituted phenyl, substituted benzyl, substituted heteroaryl or substituted heteroarylmethyl represented by $R_3$ is Selected from halogen, $C_1\text{-}C_2$ alkoxy, nitro or $C_1\text{-}C_2$ alkyl;
the heteroaryl represented by $R_3$ is preferably furyl, thienyl, pyridyl or benzofuryl;
the heteroarylmethyl represented by $R_3$ is preferably furylmethyl, thenyl, picolyl, benzofurylmethyl or benzothienyl;
the substituent of the substituted heteroaryl represented by $R_3$ is preferably furyl, thienyl, pyridyl or benzofuryl, substituted with halogen, $C_1\text{-}C_2$ alkoxy, nitro or $C_1\text{-}C_2$ alkyl;
the substituent of the substituted heteroarylmethyl represented by $R_3$ is preferably furylmethyl, thenyl, picolyl, benzofurylmethyl or benzothienyl, substituted with halogen, $C_1\text{-}C_2$ alkoxy, nitro or $C_1\text{-}C_2$ alkyl;
the heteroaryl represented by $R_5$ comprises furyl, pyrrolyl, thienyl, pyridyl, benzofuryl, benzothienyl or indolyl;
the substituent of the substituted phenyl or substituted heteroaryl represented by $R_5$ comprises halogen, $C_1\text{-}C_2$ alkoxy, nitro or $C_1\text{-}C_2$ alkyl; the hydrate comprises a hydrate containing 0.5-3 molecules of crystal water;
the salt is a salt containing a pharmaceutically acceptable anion, such as hydrochloride, hydrobromide, hydriodate, nitrate, sulfate or bisulfate, phosphate or acid phosphate, acetate, lactate, orotate, citrate, tartrate, maleate, fumarate, gluconate, saccharate, benzoate, mesylate, esylate, besylate, p-tosylate, and palmitate, wherein hydrochloride, hydrobromide, sulfate, trifluoroacetate, tartrate, mesylate or palmitate is preferred; and the salt preferably further comprises 0.5-6 molecules of crystal water, wherein hydrochloride, hydrobromide, sulfate, trifluoroacetate, mesylate or palmitate is preferred;

the compounds of the present invention may comprise, but are not limited to, the following preferred compounds:

I-1 trans-N-(4-(2-(4-(benzo[d]isothiazol-3-yl)piperazin-1-yl)ethyl)cyclohexyl)furyl-2-carboxamide,
I-2 trans-N-(4-(2-(4-(benzo[d]isothiazol-3-yl)piperazin-1-yl)ethyl)cyclohexyl)thienyl-2-carboxamide,
I-3 trans-N-(4-(2-(4-(benzo[d]isothiazol-3-yl)piperazin-1-yl)ethyl)cyclohexyl)-1H-pyrrolyl-2-carboxamide,
I-4 trans-N-(4-(2-(4-(benzo[d]isothiazol-3-yl)piperazin-1-yl)ethyl)cyclohexyl)-1H-indolyl-2-carboxamide,
I-5 trans-N-(4-(2-(4-(benzo[d]isothiazol-3-yl)piperazin-1-yl)ethyl)cyclohexyl)benzofuryl-2-carboxamide,
I-6 trans-N-(4-(2-(4-(benzo[d]isothiazol-3-yl)piperazin-1-yl)ethyl)cyclohexyl)benzo[b]thienyl-2-carboxamide,
I-7 trans-N-(4-(2-(4-(benzo[d]isothiazol-3-yl)piperazin-1-yl)ethyl)cyclohexyl)-5-cyano-furyl-2-carboxamide,
I-8 trans-N-(4-(2-(4-(benzo[d]isothiazol-3-yl)piperazin-1-yl)ethyl)cyclohexyl)-3-tert-butyl furyl-2-carboxamide,
I-9 trans-N-(4-(2-(4-(benzo[d]isothiazol-3-yl)piperazin-1-yl)ethyl)cyclohexyl)-5-methyl-1H-pyrrolyl-2-carboxamide,
I-10 trans 5-acetyl-N-(4-(2-(4-(benzo[d]isothiazol-3-yl)piperazin-1-yl)ethyl)cyclohexyl)furyl-2-carboxamide,
I-11 trans-N-(4-(2-(4-(benzo[d]isothiazol-3-yl)piperazin-1-yl)ethyl)cyclohexyl)-3-methylthienyl-2-carboxamide
I-12 trans-N-(4-(2-(4-(benzo[d]isothiazol-3-yl)piperazin-1-yl)ethyl)cyclohexyl)-3-bromothienyl-2-carboxamide,
I-13 trans-N-(4-(2-(4-(benzo[d]isothiazol-3-yl)piperazin-1-yl)ethyl)cyclohexyl)-3-ethylbenzo[b]thienyl-2-carboxamide,
I-14 trans-N-(4-(2-(4-(benzo[d]isothiazol-3-yl)piperazin-1-yl)ethyl)cyclohexyl)-3-chlorobenzo[b]thienyl-2-carboxamide,
I-15 trans-N-(4-(2-(4-(benzo[d]isothiazol-3-yl)piperazin-1-yl)ethyl)cyclohexyl)-5-nitro-1H-indolyl-2-carboxamide,
I-16 trans-N-(4-(2-(4-(benzo[d]isothiazol-3-yl)piperazin-1-yl)ethyl)cyclohexyl)-5-methoxylbenzofuryl-2-carboxamide,
I-17 trans-N-(4-(2-(4-(benzo[d]isothiazol-3-yl)piperazin-1-yl)ethyl)cyclohexyl)-2-(thien-2-yl)acetamide,
I-18 trans-N-(4-(2-(4-(benzo[d]isothiazol-3-yl)piperazin-1-yl)ethyl)cyclohexyl)-2-(benzofuran-3-yl)acetamide,
I-19 cis-N-(4-(2-(4-(benzo[d]isothiazol-3-yl)piperazin-1-yl)ethyl)cyclohexyl)furyl-2-carboxamide,
I-20 cis-N-(4-(2-(4-(benzo[d]isothiazol-3-yl)piperazin-1-yl)ethyl)cyclohexyl)thienyl-2-carboxamide,
I-21 cis-N-(4-(2-(4-(benzo[d]isothiazol-3-yl)piperazin-1-yl)ethyl)cyclohexyl)-1H-pyrrolyl-2-carboxamide,
I-22 cis-N-(4-(2-(4-(benzo[d]isothiazol-3-yl)piperazin-1-yl)ethyl)cyclohexyl)-1H-indolyl-2-carboxamide,
I-23 cis-N-(4-(2-(4-(benzo[d]isothiazol-3-yl)piperazin-1-yl)ethyl)cyclohexyl)benzofuryl-2-carboxamide,
I-24 cis-N-(4-(2-(4-(benzo[d]isothiazol-3-yl)piperazin-1-yl)ethyl)cyclohexyl)benzo[b]thienyl-2-carboxamide,
☐-1 trans-N-(4-(2-(4-(benzo[d]isothiazol-3-yl)piperazin-1-yl)ethyl)cyclohexyl)thienyl-2-sulfamide,
☐-2 trans-N-(4-(2-(4-(benzo[d]isothiazol-3-yl)piperazin-1-yl)ethyl)cyclohexyl)-1H-pyrrolyl-3-sulfamide,
☐-3 trans-N-(4-(2-(4-(benzo[d]isothiazol-3-yl)piperazin-1-yl)ethyl)cyclohexyl)furyl-2-sulfamide,
☐-4 trans-N-(4-(2-(4-(benzo[d]isothiazol-3-yl)piperazin-1-yl)ethyl)cyclohexyl)benzo[b]thienyl-2-sulfamide,
☐-5 trans-N-(4-(2-(4-(benzo[d]isothiazol-3-yl)piperazin-1-yl)ethyl)cyclohexyl)benzofuryl-2-sulfamide,
☐-6 trans-N-(4-(2-(4-(benzo[d]isothiazol-3-yl)piperazin-1-yl)ethyl)cyclohexyl)-1H-indolyl-3-sulfamide,
☐-7 trans-N-(4-(2-(4-(benzo[d]isothiazol-3-yl)piperazin-1-yl)ethyl)cyclohexyl)-5-cyanofuryl-2-sulfamide,
☐-8 trans-N-(4-(2-(4-(benzo[d]isothiazol-3-yl)piperazin-1-yl)ethyl)cyclohexyl)-5-chlorofuryl-2-sulfamide,
☐-9 trans-N-(4-(2-(4-(benzo[d]isothiazol-3-yl)piperazin-1-yl)ethyl)cyclohexyl)-5-methylfuryl-2-sulfamide
☐-10 trans-N-(4-(2-(4-(benzo[d]isothiazol-3-yl)piperazin-1-yl)ethyl)cyclohexyl)-5-tert-butylthienyl-2-sulfamide,
☐-11 trans-N-(4-(2-(4-(benzo[d]isothiazol-3-yl)piperazin-1-yl)ethyl)cyclohexyl)-5-chlorobenzo[b]thienyl-2-sulfamide,
☐-12 trans-N-(4-(2-(4-(benzo[d]isothiazol-3-yl)piperazin-1-yl)ethyl)cyclohexyl)-5-cyanobenzo[b]thienyl-2-sulfamide,
☐-13 trans-N-(4-(2-(4-(benzo[d]isothiazol-3-yl)piperazin-1-yl)ethyl)cyclohexyl)-5-methylbenzo[b]thienyl-2-sulfamide,
☐-14 trans-N-(4-(2-(4-(benzo[d]isothiazol-3-yl)piperazin-1-yl)ethyl)cyclohexyl)-5-nitrobenzo[b]thienyl-2-sulfamide,
☐-15 trans-N-(4-(2-(4-(benzo[d]isothiazol-3-yl)piperazin-1-yl)ethyl)cyclohexyl)-5-methoxylbenzofuryl-2-sulfamide
☐-16 cis-N-(4-(2-(4-(benzo[d]isothiazol-3-yl)piperazin-1-yl)ethyl)cyclohexyl)thienyl-2-sulfamide,
☐-17 cis-N-(4-(2-(4-(benzo[d]isothiazol-3-yl)piperazin-1-yl)ethyl)cyclohexyl)-1H-pyrrolyl-3-sulfamide,
☐-18 cis-N-(4-(2-(4-(benzo[d]isothiazol-3-yl)piperazin-1-yl)ethyl)cyclohexyl)furyl-2-sulfamide,
☐-19 cis-N-(4-(2-(4-(benzo[d]isothiazol-3-yl)piperazin-1-yl)ethyl)cyclohexyl)benzo[b]thienyl-2-sulfamide,
☐-20 cis-N-(4-(2-(4-(benzo[d]isothiazol-3-yl)piperazin-1-yl)ethyl)cyclohexyl)benzofuryl-2-sulfamide,
☐-21 cis-N-(4-(2-(4-(benzo[d]isothiazol-3-yl)piperazin-1-yl)ethyl)cyclohexyl)-1H-indolyl-3-sulfamide,
☐-22 cis-N-(4-(2-(4-(benzo[d]isothiazol-3-yl)piperazin-1-yl)ethyl)cyclohexyl)-5-methylfuryl-2-sulfamide,
☐-1 trans-(4-(2-(4-(benzo[d]isothiazol-3-yl)piperazin-1-yl)ethyl)cyclohexyl)methylcarbamate,
☐-2 trans-(4-(2-(4-(benzo[d]isothiazol-3-yl)piperazin-1-yl)ethyl)cyclohexyl)ethylcarbamate,
☐-3 trans-N-(4-(2-(4-(benzo[d]isothiazol-3-yl)piperazin-1-yl)ethyl)cyclohexyl)isobutylcarbamate,
☐-4 trans-(4-(2-(4-(benzo[d]isothiazol-3-yl)piperazin-1-yl)ethyl)cyclohexyl)cyclopropylcarbamate,
☐-5 trans-(4-(2-(4-(benzo[d]isothiazol-3-yl)piperazin-1-yl)ethyl)cyclohexyl)cyclohexylcarbamate,
☐-6 trans-(4-(2-(4-(benzo[d]isothiazol-3-yl)piperazin-1-yl)ethyl)cyclohexyl)phenylcarbamate,
☐-7 trans-(4-(2-(4-(benzo[d]isothiazol-3-yl)piperazin-1-yl)ethyl)cyclohexyl)-3-methoxylphenylcarbamate,
☐-8 trans-(4-(2-(4-(benzo[d]isothiazol-3-yl)piperazin-1-yl)ethyl)cyclohexyl)-2-methylphenylcarbamate,
☐-9 trans-(4-(2-(4-(benzo[d]isothiazol-3-yl)piperazin-1-yl)ethyl)cyclohexyl)-4-chlorophenylcarbamate,
☐-10 trans-(4-(2-(4-(benzo[d]isothiazol-3-yl)piperazin-1-yl)ethyl)cyclohexyl)-4-nitrophenylcarbamate,
☐-11 trans-(4-(2-(4-(benzo[d]isothiazol-3-yl)piperazin-1-yl)ethyl)cyclohexyl)benzylcarbamate,
☐-12 trans-(4-(2-(4-(benzo[d]isothiazol-3-yl)piperazin-1-yl)ethyl)cyclohexyl)benzofuryl-2-methylcarbamate,
☐-13 trans-(4-(2-(4-(benzo[d]isothiazol-3-yl)piperazin-1-yl)ethyl)cyclohexyl)thienyl-2-methylcarbamate,
☐-14 cis-(4-(2-(4-(benzo[d]isothiazol-3-yl)piperazin-1-yl)ethyl)cyclohexyl)methylcarbamate, ☐-15 cis-(4-(2-(4-(benzo[d]isothiazol-3-yl)piperazin-1-yl)ethyl)cyclohexyl)ethylcarbamate,
☐-16 cis-(4-(2-(4-(benzo[d]isothiazol-3-yl)piperazin-1-yl)ethyl)cyclohexyl)benzylcarbamate,
☐-1 trans-1-(4-(2-(4-(benzo[d]isothiazol-3-yl)piperazin-1-yl)ethyl)cyclohexyl)-3-phenylurea,
☐-2 trans-1-(4-(2-(4-(benzo[d]isothiazol-3-yl)piperazin-1-yl)ethyl)cyclohexyl)-3-phenylethyl urea,
☐-3 trans-1-(4-(2-(4-(benzo[d]isothiazol-3-yl)piperazin-1-yl)ethyl)cyclohexyl)-3-(pyridin-3-yl)urea,
☐-4 trans-1-(4-(2-(4-(benzo[d]isothiazol-3-yl)piperazin-1-yl)ethyl)cyclohexyl)-3-(furan-2-yl)urea,
☐-5 trans-1-(benzo[b]thien-2-yl)-3-(4-(2-(4-(benzo[d]isothiazol-3-yl) piperazin-1-yl)ethyl)cyclohexyl)urea,
☐-6 trans-3-(4-(2-(4-(benzo[d]isothiazol-3-yl)piperazin-1-yl)ethyl)cyclohexyl)-1-methyl-1-phenylurea,
☐-7 trans-3-(4-(2-(4-(benzo[d]isothiazol-3-yl)piperazin-1-yl)ethyl)cyclohexyl)-1-butyl-1-phenylurea,
☐-8 trans-3-(4-(2-(4-(benzo[d]isothiazol-3-yl)piperazin-1-yl)ethyl)cyclohexyl)-1-methyl-1-(thien-2-yl)urea,
☐-9 trans-1-(4-(2-(4-(benzo[d]isothiazol-3-yl)piperazin-1-yl)ethyl)cyclohexyl)-3-(3-methoxyphenyl)urea,
☐-10 trans-1-(4-(2-(4-(benzo[d]isothiazol-3-yl)piperazin-1-yl)ethyl)cyclohexyl)-3-(3-nitrophenyl)urea,
☐-11 trans-1-(4-(2-(4-(benzo[d]isothiazol-3-yl)piperazin-1-yl)ethyl)cyclohexyl)-3-benzoylurea,
☐-12 cis-1-(4-(2-(4-(benzo[d]isothiazol-3-yl)piperazin-1-yl)ethyl)cyclohexyl)-3-phenylurea,
☐-13 cis-1-(4-(2-(4-(benzo[d]isothiazol-3-yl)piperazin-1-yl)ethyl)cyclohexyl)-3-benzoylurea, or
☐-14 cis-1-(4-(2-(4-(benzo[d]isothiazol-3-yl)piperazin-1-yl)ethyl)cyclohexyl)-3-(furan-2-yl)urea.

The structures of the above preferred compounds are shown in the table below:

| No. | Structure |
|---|---|
| I-1 | $R_1{-}(\ )_n{-}C({=}O){-}$ (attached via wavy bond) |
| I-2 | $R_3{-}O{-}C({=}O){-}$ (attached via wavy bond) |
| I-3 | pyrrole-2-carboxamide-N-(cyclohexyl)-ethyl-piperazinyl-benzo[d]isothiazole |
| I-4 | indole-2-carboxamide-N-(cyclohexyl)-ethyl-piperazinyl-benzo[d]isothiazole |
| I-5 | benzofuran-2-carboxamide-N-(cyclohexyl)-ethyl-piperazinyl-benzo[d]isothiazole |

-continued
| No. | Structure |
|---|---|
| I-6 | 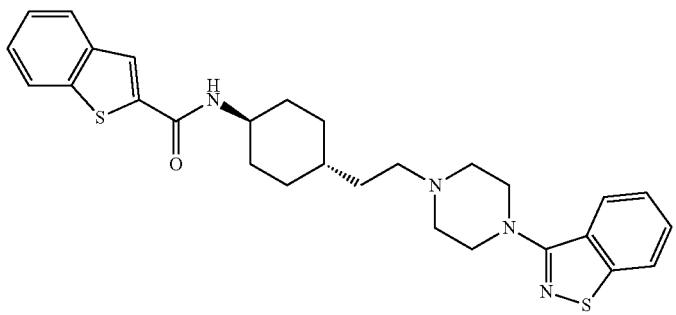 [SMILES: O=C(N[C@H]1CC[C@H](CCN2CCN(c3nsc4ccccc34)CC2)CC1)c1cc2ccccc2s1] |
| I-7 | 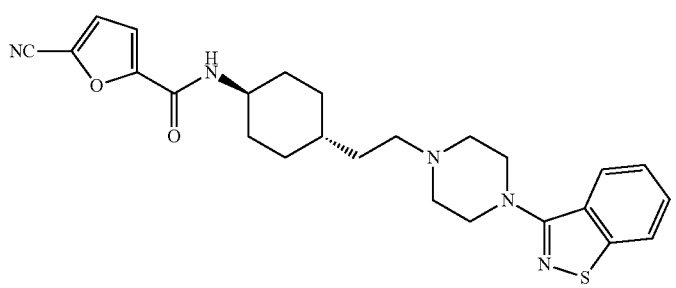 [SMILES: N#Cc1ccc(C(=O)N[C@H]2CC[C@H](CCN3CCN(c4nsc5ccccc45)CC3)CC2)o1] |
| I-8 | 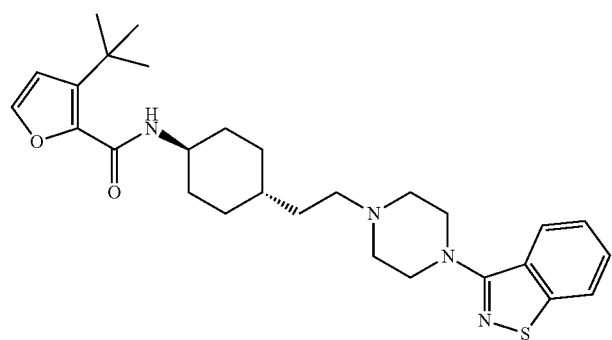 [SMILES: CC(C)(C)c1ccoc1C(=O)N[C@H]1CC[C@H](CCN2CCN(c3nsc4ccccc34)CC2)CC1] |
| I-9 | 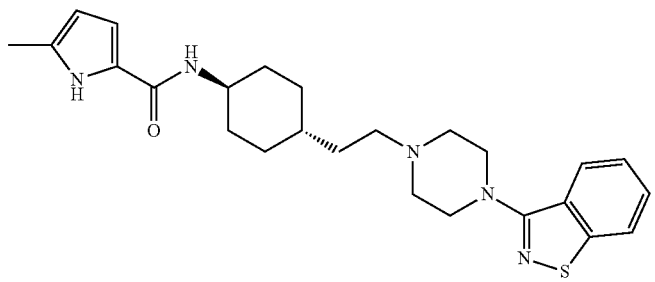 [SMILES: Cc1ccc(C(=O)N[C@H]2CC[C@H](CCN3CCN(c4nsc5ccccc45)CC3)CC2)[nH]1] |
| I-10 | 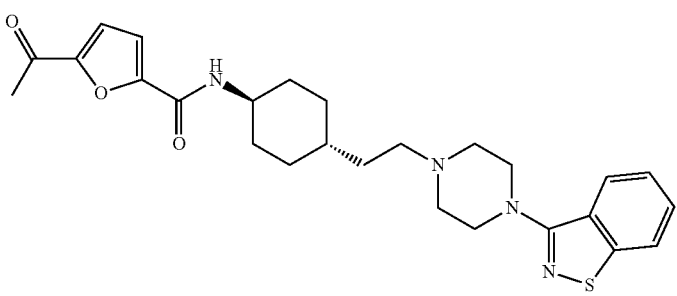 [SMILES: CC(=O)c1ccc(C(=O)N[C@H]2CC[C@H](CCN3CCN(c4nsc5ccccc45)CC3)CC2)o1] |

-continued
| No. | Structure |
|---|---|
| I-11 | 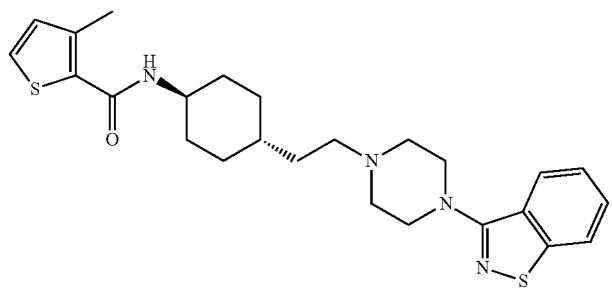 [SMILES: Cc1ccsc1C(=O)N[C@H]1CC[C@H](CCN2CCN(c3nsc4ccccc34)CC2)CC1] |
| I-12 | 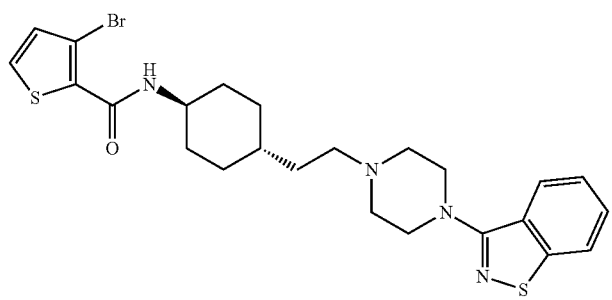 [SMILES: O=C(N[C@H]1CC[C@H](CCN2CCN(c3nsc4ccccc34)CC2)CC1)c1sccc1Br] |
| I-13 | 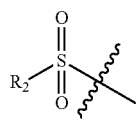 |
| I-14 | 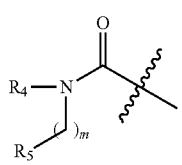 |
| I-15 | 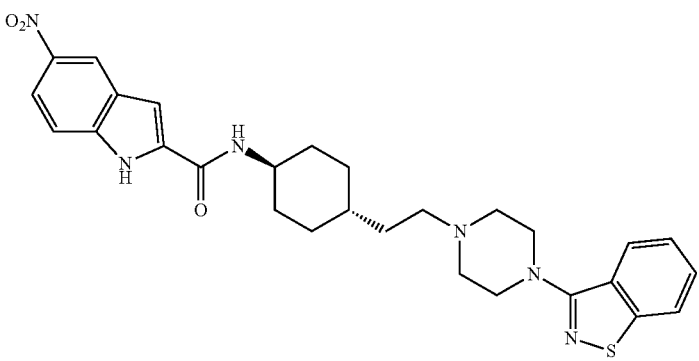 [SMILES: O=C(N[C@H]1CC[C@H](CCN2CCN(c3nsc4ccccc34)CC2)CC1)c1cc2cc([N+](=O)[O-])ccc2[nH]1] |
| I-16 | 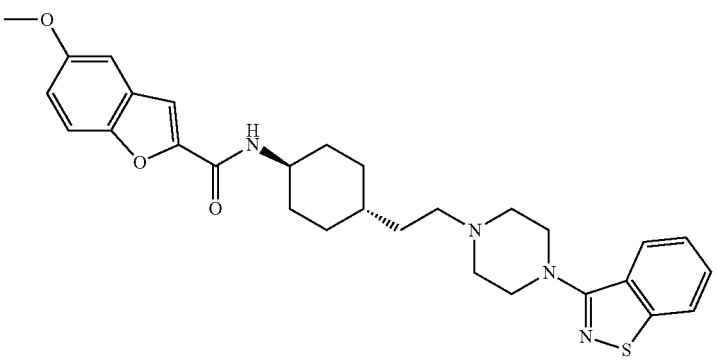 [SMILES: COc1ccc2oc(C(=O)N[C@H]3CC[C@H](CCN4CCN(c5nsc6ccccc56)CC4)CC3)cc2c1] |

| No. | Structure |
|---|---|
| I-17 | 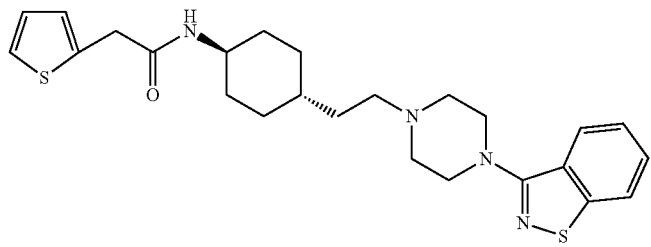 [SMILES: O=C(Cc1cccs1)N[C@H]1CC[C@H](CCN2CCN(c3nsc4ccccc34)CC2)CC1] |
| I-18 | 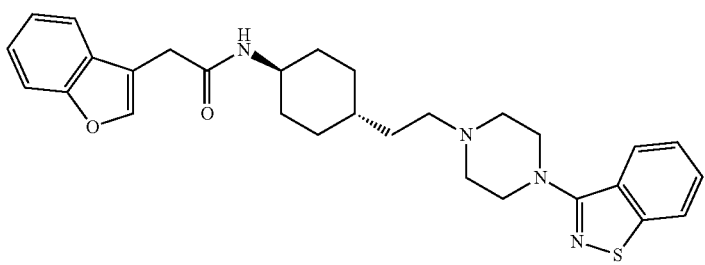 [SMILES: O=C(Cc1coc2ccccc12)N[C@H]1CC[C@H](CCN2CCN(c3nsc4ccccc34)CC2)CC1] |
| I-19 | 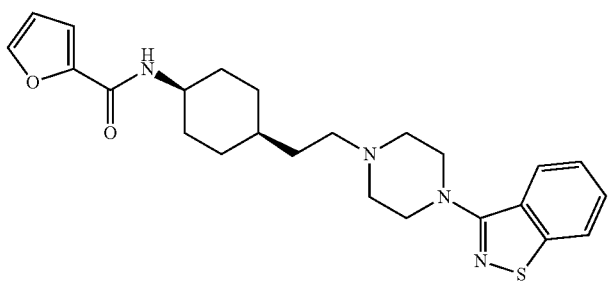 [SMILES: O=C(N[C@H]1CC[C@@H](CCN2CCN(c3nsc4ccccc34)CC2)CC1)c1ccco1] |
| I-20 | 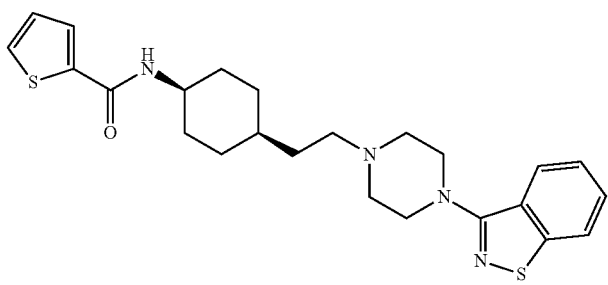 [SMILES: O=C(N[C@H]1CC[C@@H](CCN2CCN(c3nsc4ccccc34)CC2)CC1)c1cccs1] |
| I-21 | 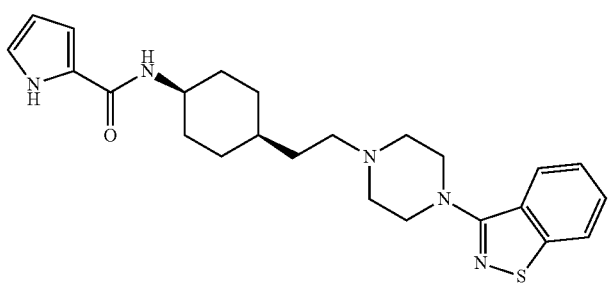 [SMILES: O=C(N[C@H]1CC[C@@H](CCN2CCN(c3nsc4ccccc34)CC2)CC1)c1ccc[nH]1] |

| No. | Structure |
|---|---|
| I-22 | 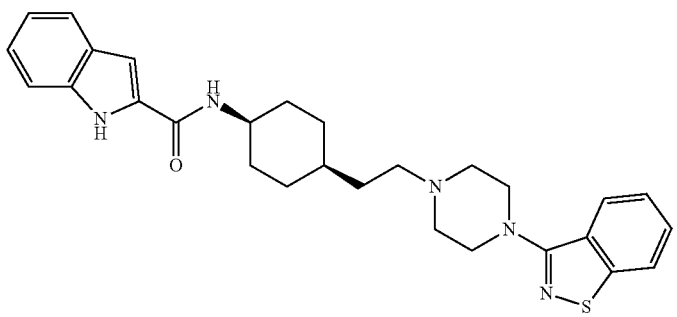 [SMILES: O=C(N[C@H]1CC[C@@H](CCN2CCN(c3nsc4ccccc34)CC2)CC1)c1cc2ccccc2[nH]1] |
| I-23 | 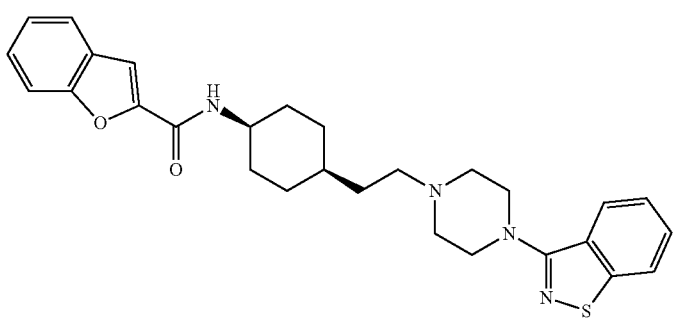 [SMILES: O=C(N[C@H]1CC[C@@H](CCN2CCN(c3nsc4ccccc34)CC2)CC1)c1cc2ccccc2s1] |
| I-24 | 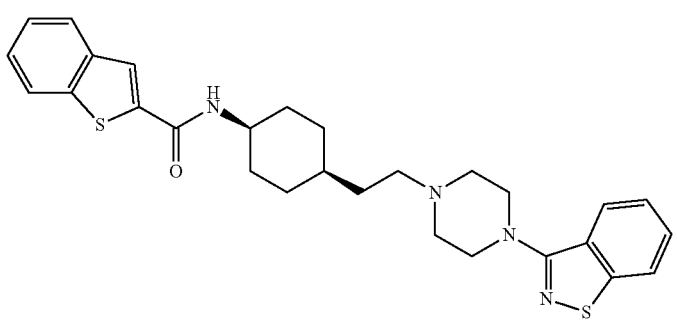 |
| II-1 | 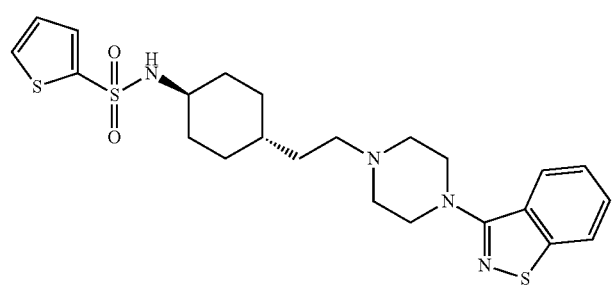 |
| II-2 | 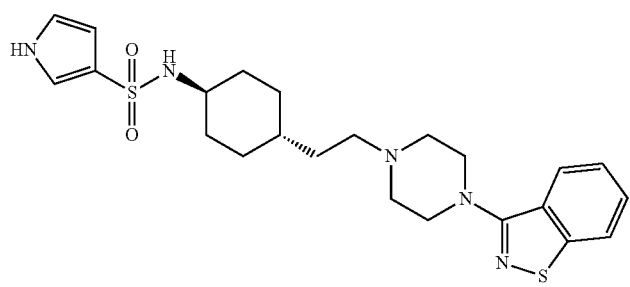 [SMILES: O=S(=O)(N[C@H]1CC[C@H](CCN2CCN(c3nsc4ccccc34)CC2)CC1)c1cc[nH]c1] |

| No. | Structure |
|---|---|
| □-3 | (furan-2-sulfonamide linked to cyclohexyl-ethyl-piperazinyl-benzisothiazole) |
| □-4 | (benzothiophene-2-sulfonamide linked to cyclohexyl-ethyl-piperazinyl-benzisothiazole) |
| □-5 | (benzofuran-2-sulfonamide linked to cyclohexyl-ethyl-piperazinyl-benzisothiazole) |
| □-6 | (1H-indole-3-sulfonamide linked to cyclohexyl-ethyl-piperazinyl-benzisothiazole) |
| □-7 | (5-cyanofuran-2-sulfonamide linked to cyclohexyl-ethyl-piperazinyl-benzisothiazole) |

| No. | Structure |
|---|---|
| □-8 | 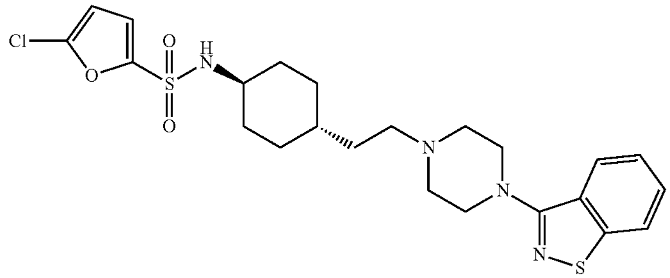 [SMILES: O=S(=O)(N[C@H]1CC[C@H](CCN2CCN(c3nsc4ccccc34)CC2)CC1)c1ccc(Cl)o1] |
| □-9 | 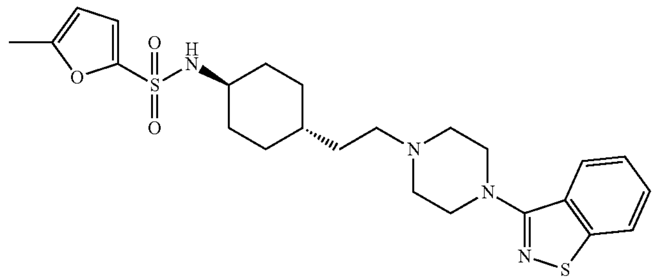 [SMILES: Cc1ccc(S(=O)(=O)N[C@H]2CC[C@H](CCN3CCN(c4nsc5ccccc45)CC3)CC2)o1] |
| □-10 | 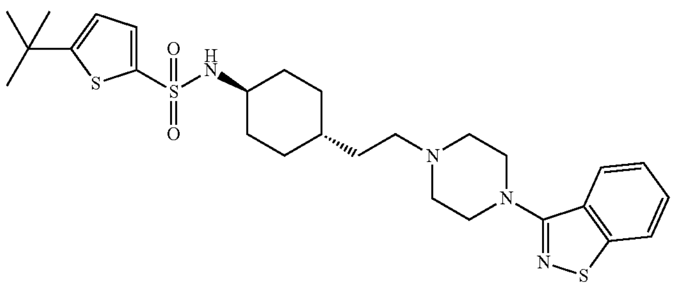 [SMILES: CC(C)(C)c1ccc(S(=O)(=O)N[C@H]2CC[C@H](CCN3CCN(c4nsc5ccccc45)CC3)CC2)s1] |
| □-11 | 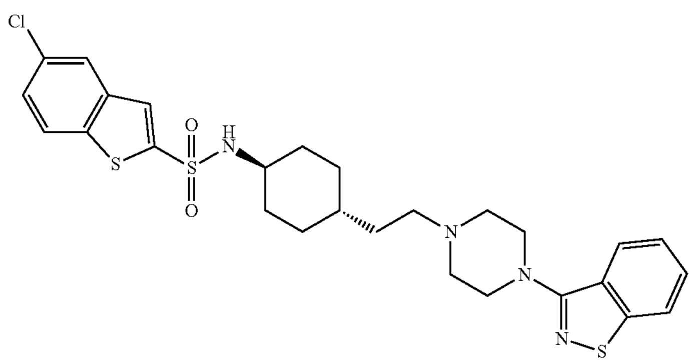 [SMILES: O=S(=O)(N[C@H]1CC[C@H](CCN2CCN(c3nsc4ccccc34)CC2)CC1)c1cc2cc(Cl)ccc2s1] |
| □-12 | 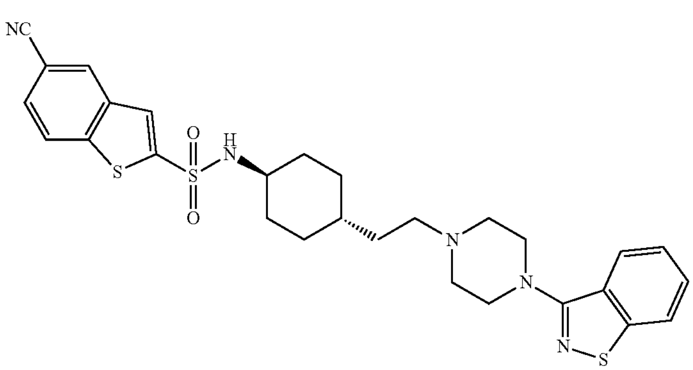 [SMILES: N#Cc1ccc2sc(S(=O)(=O)N[C@H]3CC[C@H](CCN4CCN(c5nsc6ccccc56)CC4)CC3)cc2c1] |

| No. | Structure |
|---|---|
| □-13 | 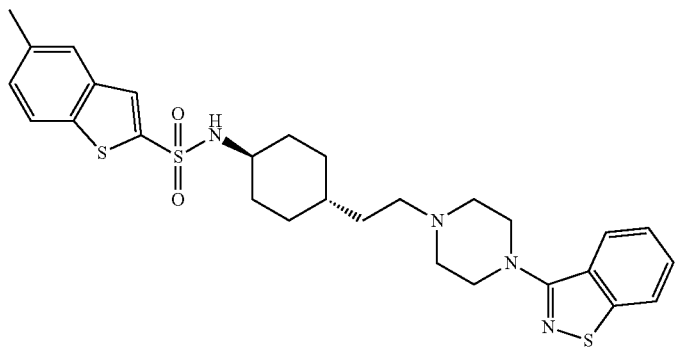 [SMILES: Cc1ccc2sc(S(=O)(=O)N[C@H]3CC[C@H](CCN4CCN(c5nsc6ccccc56)CC4)CC3)cc2c1] |
| □-14 | 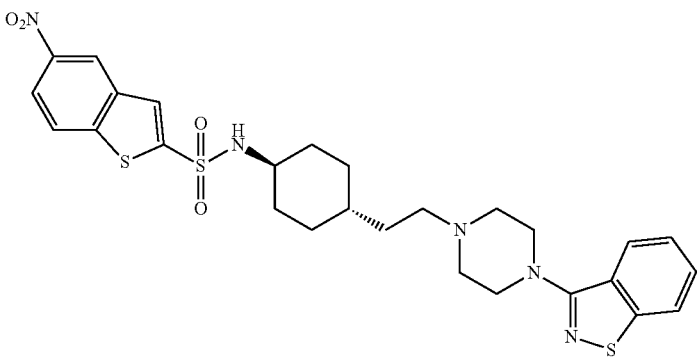 [SMILES: O=[N+]([O-])c1ccc2sc(S(=O)(=O)N[C@H]3CC[C@H](CCN4CCN(c5nsc6ccccc56)CC4)CC3)cc2c1] |
| □-15 | 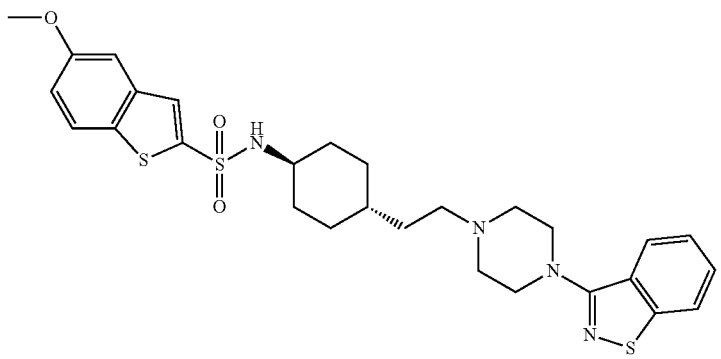 [SMILES: COc1ccc2sc(S(=O)(=O)N[C@H]3CC[C@H](CCN4CCN(c5nsc6ccccc56)CC4)CC3)cc2c1] |
| □-16 | 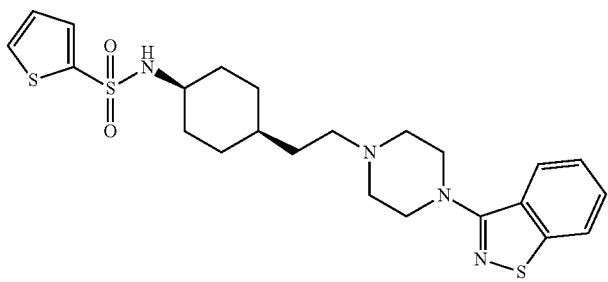 |

-continued
| No. | Structure |
|---|---|
| ☐-17 | 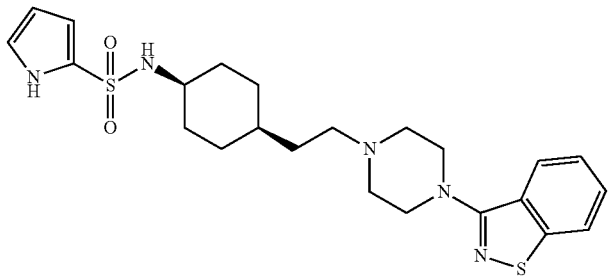 |
| ☐-18 | 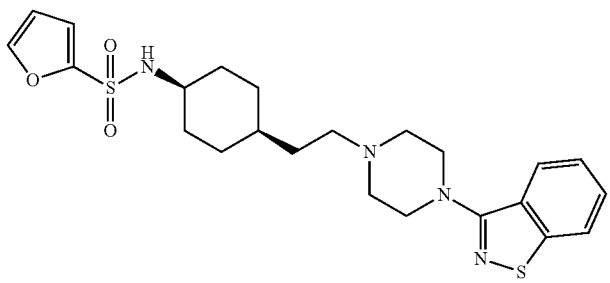 [SMILES: O=S(=O)(N[C@H]1CC[C@@H](CCN2CCN(c3nsc4ccccc34)CC2)CC1)c1cccs1] |
| ☐-19 | 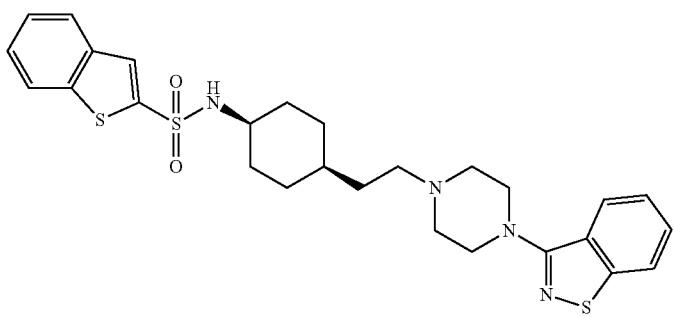 |
| ☐-20 | 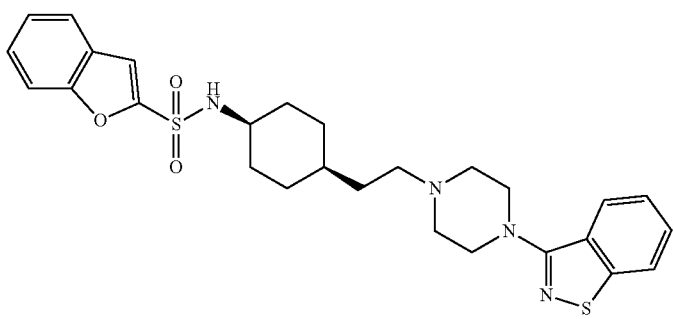 [SMILES: O=S(=O)(N[C@H]1CC[C@@H](CCN2CCN(c3nsc4ccccc34)CC2)CC1)c1cc2ccccc2s1] |
| ☐-21 | 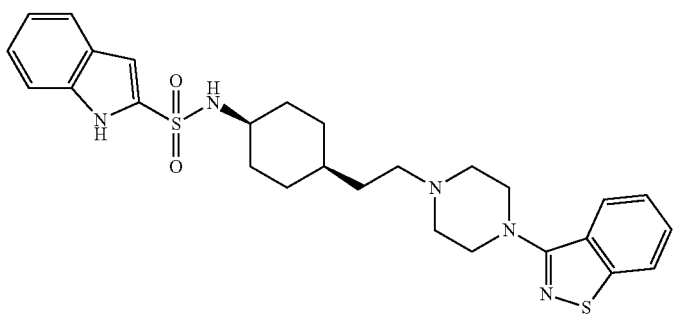 [SMILES: O=S(=O)(N[C@H]1CC[C@@H](CCN2CCN(c3nsc4ccccc34)CC2)CC1)c1cc2ccccc2[nH]1] |

-continued
| No. | Structure |
|---|---|
| ☐-22 | 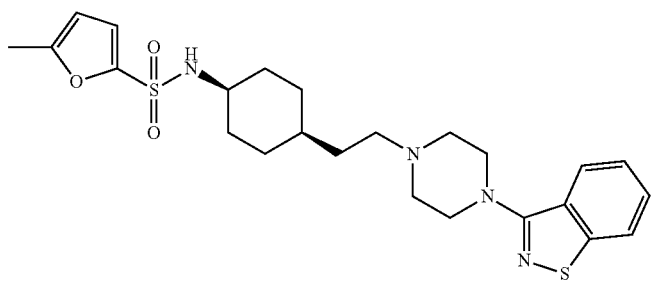 [SMILES: Cc1ccc(S(=O)(=O)N[C@H]2CC[C@@H](CCN3CCN(c4nsc5ccccc45)CC3)CC2)o1] |
| ☐-1 | 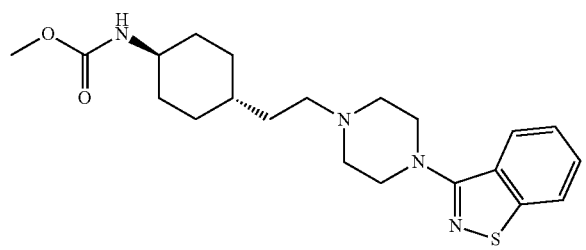 [SMILES: COC(=O)N[C@H]1CC[C@H](CCN2CCN(c3nsc4ccccc34)CC2)CC1] |
| ☐-2 | 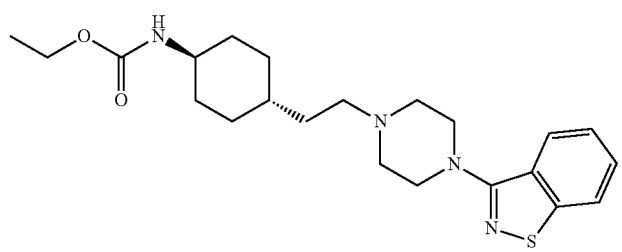 [SMILES: CCOC(=O)N[C@H]1CC[C@H](CCN2CCN(c3nsc4ccccc34)CC2)CC1] |
| ☐-3 | 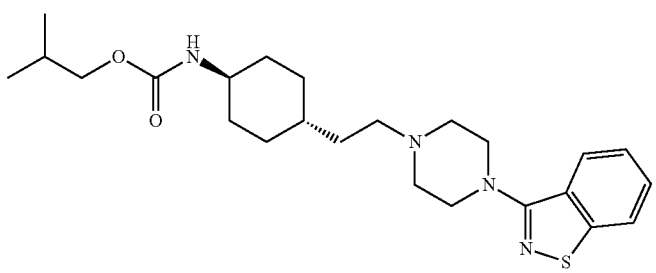 [SMILES: CC(C)COC(=O)N[C@H]1CC[C@H](CCN2CCN(c3nsc4ccccc34)CC2)CC1] |
| ☐-4 | 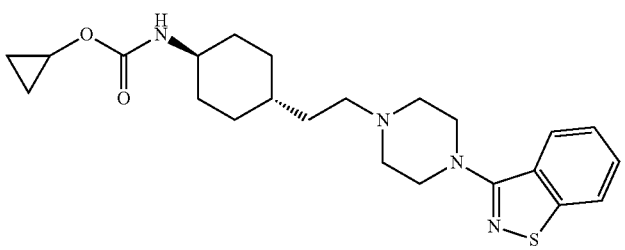 [SMILES: O=C(N[C@H]1CC[C@H](CCN2CCN(c3nsc4ccccc34)CC2)CC1)OC1CC1] |
| ☐-5 | 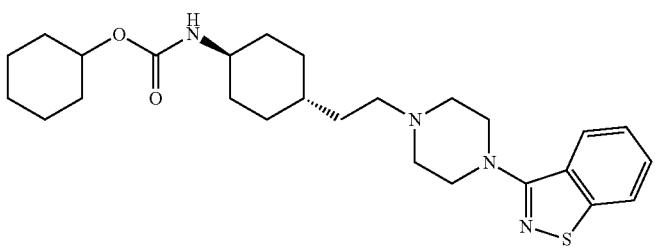 [SMILES: O=C(N[C@H]1CC[C@H](CCN2CCN(c3nsc4ccccc34)CC2)CC1)OC1CCCCC1] |

-continued
| No. | Structure |
|---|---|
| I-6 | 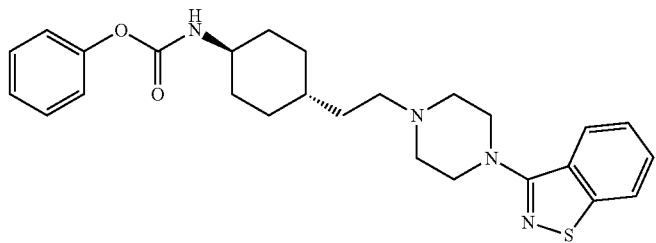 [SMILES: O=C(N[C@H]1CC[C@H](CCN2CCN(c3nsc4ccccc34)CC2)CC1)Oc1ccccc1] |
| I-7 | 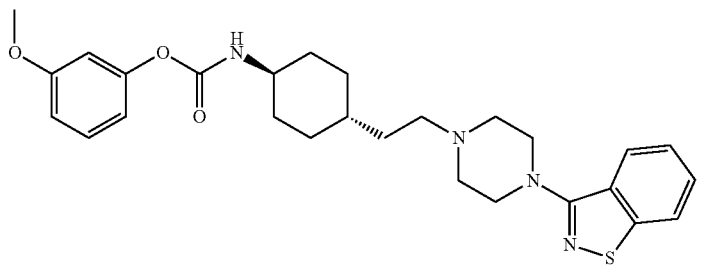 [SMILES: COc1cccc(OC(=O)N[C@H]2CC[C@H](CCN3CCN(c4nsc5ccccc45)CC3)CC2)c1] |
| I-8 | 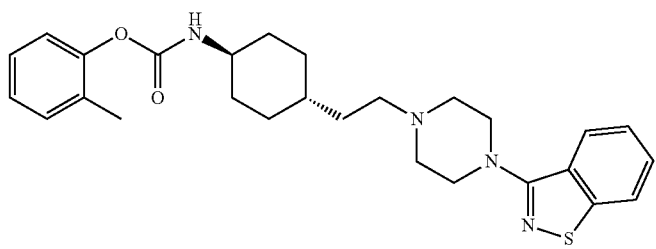 [SMILES: Cc1ccccc1OC(=O)N[C@H]1CC[C@H](CCN2CCN(c3nsc4ccccc34)CC2)CC1] |
| I-9 | 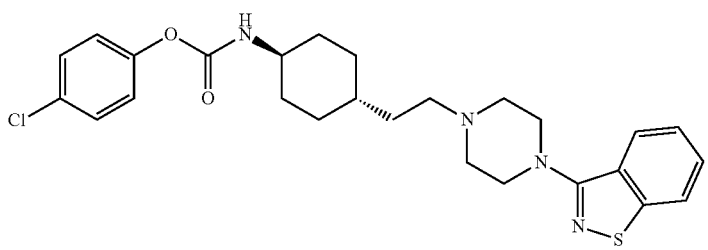 [SMILES: O=C(N[C@H]1CC[C@H](CCN2CCN(c3nsc4ccccc34)CC2)CC1)Oc1ccc(Cl)cc1] |
| I-10 | 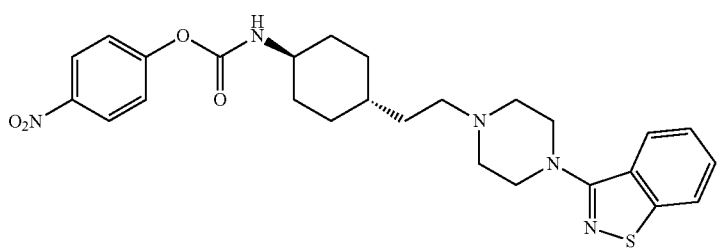 [SMILES: O=C(N[C@H]1CC[C@H](CCN2CCN(c3nsc4ccccc34)CC2)CC1)Oc1ccc([N+](=O)[O-])cc1] |
| I-11 | 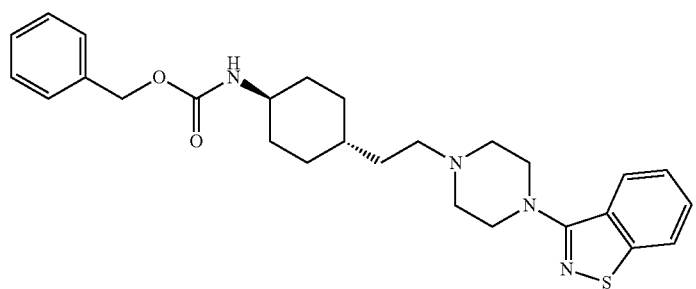 [SMILES: O=C(N[C@H]1CC[C@H](CCN2CCN(c3nsc4ccccc34)CC2)CC1)OCc1ccccc1] |

| No. | Structure |
|---|---|
| I-12 | 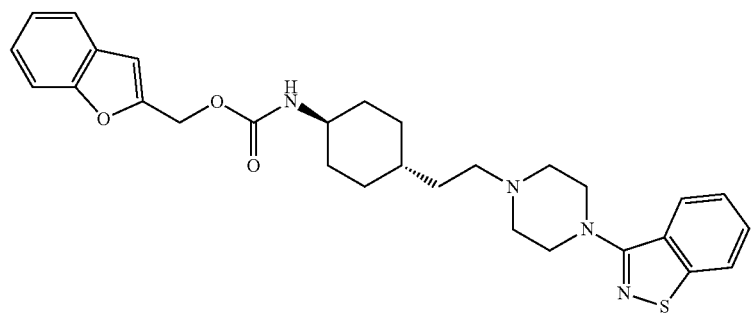 [SMILES: O=C(N[C@H]1CC[C@H](CCN2CCN(c3nsc4ccccc34)CC2)CC1)OCc1cc2ccccc2o1] |
| I-13 | 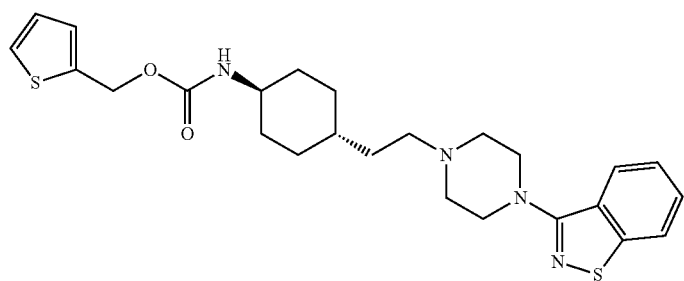 [SMILES: O=C(N[C@H]1CC[C@H](CCN2CCN(c3nsc4ccccc34)CC2)CC1)OCc1cccs1] |
| I-14 | 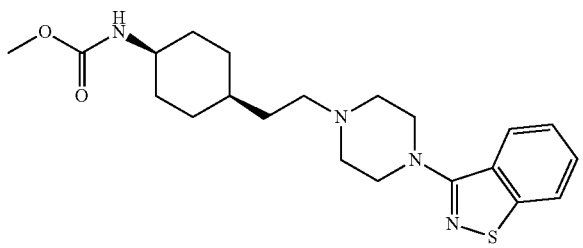 [SMILES: COC(=O)N[C@H]1CC[C@@H](CCN2CCN(c3nsc4ccccc34)CC2)CC1] |
| I-15 | 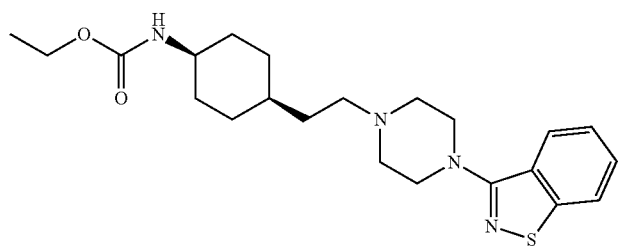 [SMILES: CCOC(=O)N[C@H]1CC[C@@H](CCN2CCN(c3nsc4ccccc34)CC2)CC1] |
| I-16 | 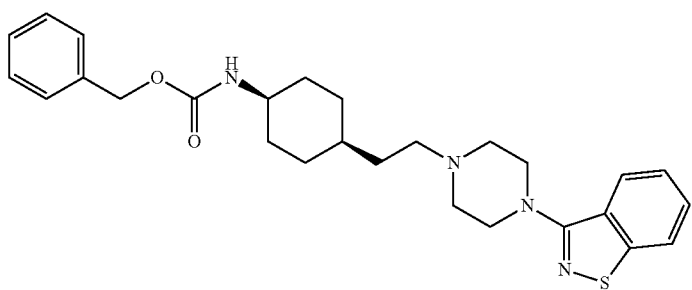 [SMILES: O=C(N[C@H]1CC[C@@H](CCN2CCN(c3nsc4ccccc34)CC2)CC1)OCc1ccccc1] |

| No. | Structure |
|---|---|
| ☐-1 | |
| ☐-2 | |
| ☐-3 | |
| ☐-4 | |
| ☐-5 | |
| ☐-6 | |

-continued
| No. | Structure |
|---|---|
| I-7 | 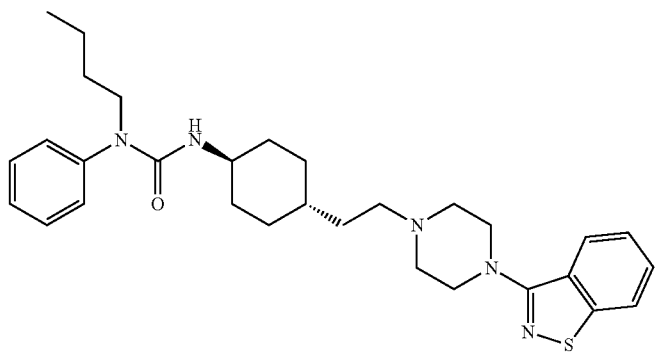 [SMILES: CCCCN(C(=O)N[C@H]1CC[C@H](CCN2CCN(c3nsc4ccccc34)CC2)CC1)c1ccccc1] |
| I-8 | 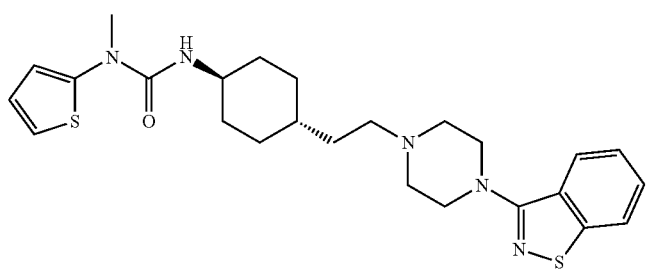 [SMILES: CN(C(=O)N[C@H]1CC[C@H](CCN2CCN(c3nsc4ccccc34)CC2)CC1)c1cccs1] |
| I-9 | 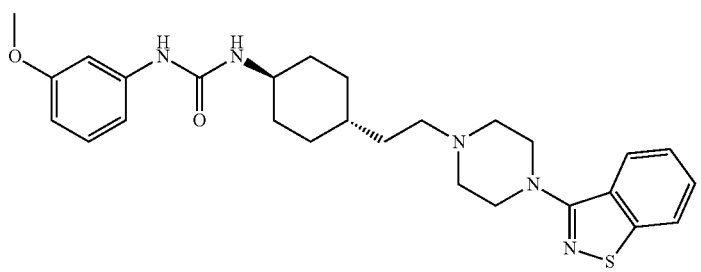 |
| I-10 | 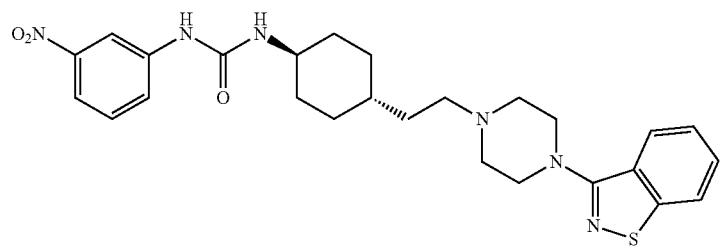 [SMILES: O=C(Nc1cccc([N+](=O)[O-])c1)N[C@H]1CC[C@H](CCN2CCN(c3nsc4ccccc34)CC2)CC1] |
| I-11 | 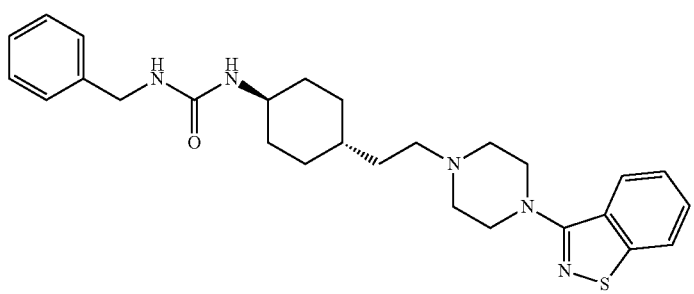 [SMILES: O=C(NCc1ccccc1)N[C@H]1CC[C@H](CCN2CCN(c3nsc4ccccc34)CC2)CC1] |

| No. | Structure |
|---|---|
| I-12 | 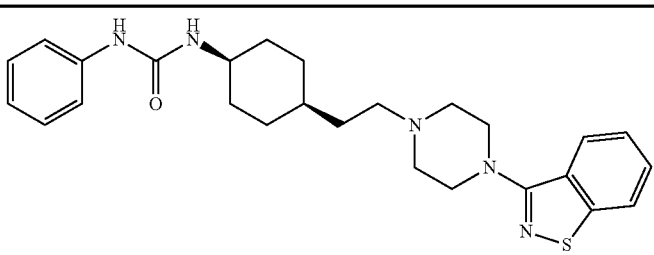 |
| I-13 | 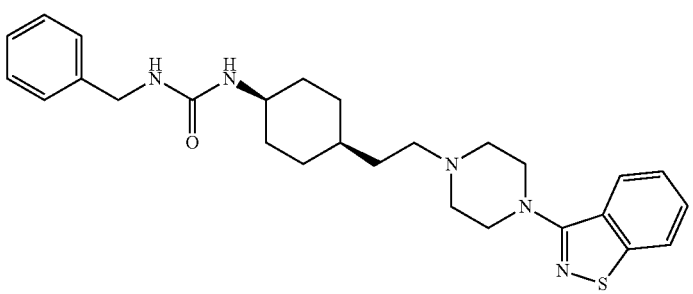 [SMILES: O=C(NCc1ccccc1)N[C@H]1CC[C@@H](CCN2CCN(c3nsc4ccccc34)CC2)CC1] |
| I-14 | 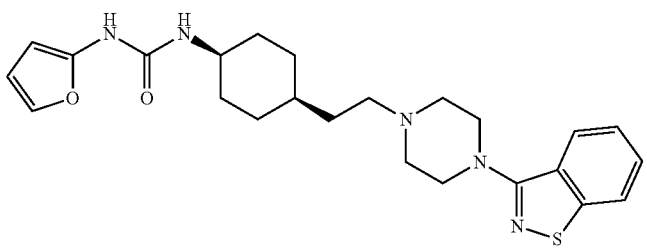 [SMILES: O=C(Nc1ccco1)N[C@H]1CC[C@@H](CCN2CCN(c3nsc4ccccc34)CC2)CC1] |

The present invention also relates to a composition for treating schizophrenia, said composition comprising a therapeutically effective amount of the compound having the structure of general formula (I) or the geometric isomers, free alkalies, salts, hydrates or solvates thereof and a pharmaceutically acceptable carrier.

The carrier refers to a conventional drug carrier in the pharmaceutical field, for example a diluent, an excipient (such as water), a filler such as starch, sucrose, lactose, microcrystalline cellulose etc., a binder such as a cellulose derivative, gelatin, polyvinylpyrrolidone etc., a wetting agent such as glycerol etc., a surfactant such as cetanol etc., a disintegrant such as calcium carbonate, crospovidone, sodium starch glycollate, etc., a lubricant such as talc, sodium stearoyl fumarate, calcium stearate, magnesium stearate, etc.

Well known methods in the field may be used to mix the therapeutically effective amount of the compound of the present invention with one or more of pharmaceutically acceptable carriers and to prepare conventional solid formulations such as tablet, powder, granule, capsule or injection, etc, in which the content of the active component is 0.1%-99.5% (by weight).

The compound of the present invention can be administered to the patient in need thereof orally or by injection. For oral administration, the compound may be prepared as conventional solid formulations such as tablet, powder, capsules or the like, while for administration by injection, the compound may be prepared as an injection solution. The administration dosages of the present invention can be varied depending on the route of administration, the age, body weight, and gender of the patient, the type and the severity of the treated disease, etc., which can be 1.5-500 mg/kg body weight/day.

The compound of the present invention can be synthesized by three reaction schemes, in which reaction scheme one is applicable to the synthesis of compounds in trans-form, reaction scheme two is applicable to the synthesis of compounds in cis-form, and reaction scheme three is applicable to the synthesis of compound IV. In addition, Cariprazine (RG-18) hydrochloride is also synthesized in the present invention according to the methods reported in WO2010070370 and WO2011073705 as a control sample for in vivo and in vitro activity screening.

Scheme One: for the systhesis of compounds in trans-form

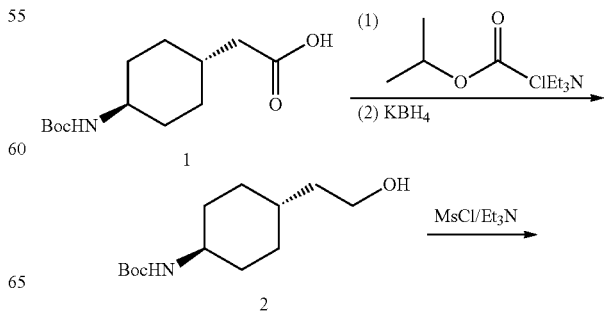

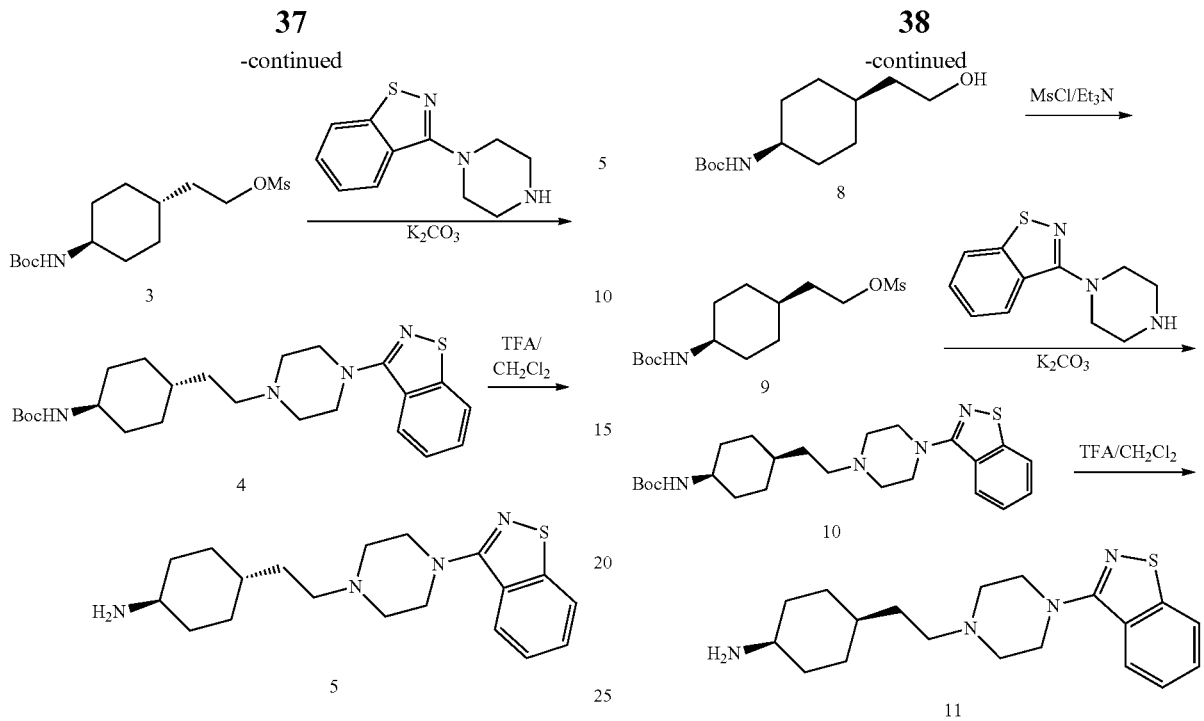

Compound 5 reacts with corresponding carbonyl chloride or sulfonyl chloride or carboxylic acid to yield the target compound, for example I-1

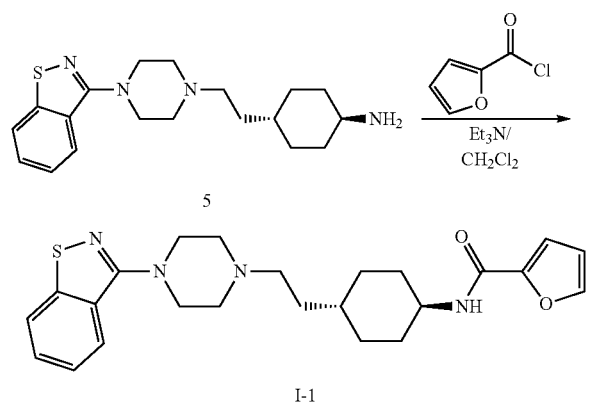

Scheme Two: for the synthesis of compounds in cis-form

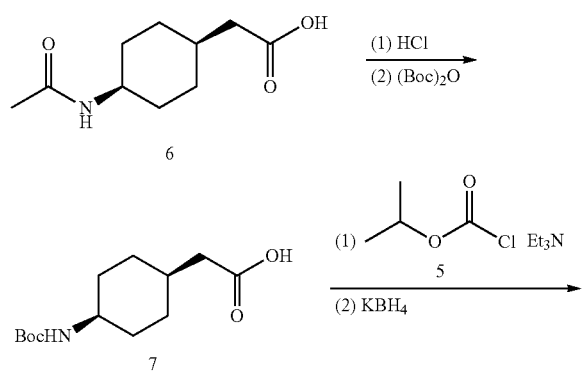

wherein the starting raw material 6 is prepared according to the method described in the reference Journal of Medicinal Chemistry, 1977, 20(2): 279290, and intermediate 7 can be obtained through the transformation of the protective group. Intermediate 7 can be reacted to yield compound 11 by the same method as scheme one. By reacting compound 11 in cis-form with corresponding carbonyl chloride or sulfonyl chloride or carboxylic acid, a corresponding target product can also be prepared. Specific synthetic methods can be found in the examples for preparing each of the compounds.

Scheme Three: for the systhesis of compounds of IV class

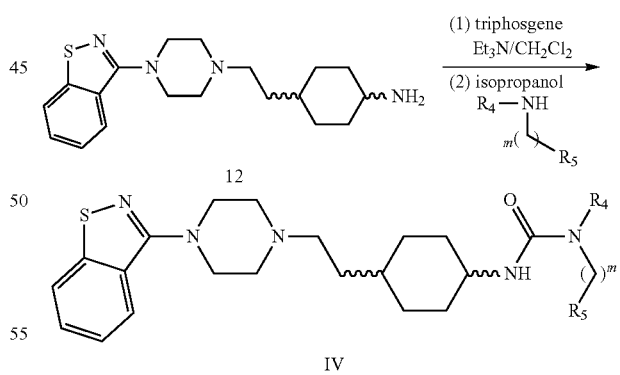

m is an integer between 0 and 2; R4 is hydrogen atom or C1-C4 alkyl; R5 is aryl, or aryl substituted with halogen, C1-C2 alkoxy, nitro or C1-C2 alkyl.

The starting raw material 12 corresponds to intermediate 5 or intermediate 11, wherein intermediate 5 is prepared according to scheme one, and intermediate 11 is prepared according to scheme two. 12 is reacted with triphosgene to produce isocyanate which is added into the solution of an amino-containing compound in isopropanol to yield the target product by one-pot method. The specific synthetic method can be found in the examples for preparing compounds of IV class.

It is demonstrated by pharmacological results that the benzoisothiazole compound (I) of the present invention shows strong affinity to both dopamine $D_3$ and 5-$HT_{1A}$ receptors, strong or moderate affinity to $D_2$ receptor, and good $D_3/D_2$ receptor selectivity, wherein the preferred compounds have the $D_3/D_2$ receptor selectivity in the range of 6:1 to 100:1, indicating that this kind of compounds are less liable to produce side effects such as catalepsy or the like and improvement effect on cognitive impairment. Surprisingly, this kind of compounds also have strong affinity to 5-$HT_{2A}$ receptor. It is found by comparing the compounds of the present invention with commercially available and developing anti-schizophrenia drugs that, the above working mechanism can overcome the side effects caused by the excessive $D_2$ blockage due to the currently studied drugs. Therefore, the side effects of anti-schizophrenia drugs can be reduced to a lower level, while the schizophrenic negative symptoms can be further improved. Thus, the benzoisothiazole compound of the present invention shows significant therapeutic effect over commercially available and developing anti-schizophrenia drugs.

The benzoisothiazole compound of the present invention may have improvement and therapeutic effect on multiple neuropsychiatric diseases, and can be used in the treatment of schizophrenia, depression, anxiety, drug abuse, mania, senile dementia, neuropathic pain or Parkinson's disease, etc., especially in the treatment of schizophrenia.

It is shown by in vitro receptor binding tests that most compounds of the present invention have strong affinity to dopamine $D_3$, 5-$HT_{1A}$, and 5-$HT_{2A}$ receptors (Ki<10 nmol or less), strong or moderate affinity to dopamine $D_2$ receptor (Ki<30 nmol), and good $D_3/D_2$ receptor selectivity. Representative compound for example I-6 has the $D_3/D_2$ receptor selectivity of up to 52:1, which is superior to the positive drug RGH-188 (with the selectivity of 8:1) and thus is worth in-depth research.

It is demonstrated by in vivo tests in animal models that the above compounds can significantly improve relevant symptoms in the apomorphine and MK-801 mouse models. The above effector targets and animal models are closely related with the nervous system diseases caused by dopaminergic system disorder etc., especially closely related with schizophrenia. Therefore, the compound of the present invention can be used to treat schizophrenia.

It is demonstrated by safety and pharmacokinetic researches that the compounds as recited in the claims all have a good oral absorption, a lower acute toxicity than RGH-188, and a wide therapeutic window, and the pharmacokinetic characteristics fulfil the requirements of druggability. Therefore, the compounds are worth being developed as novel anti-neuropsychiatric drugs.

In summary, the benzoisothiazole compounds of the present invention have strong affinity to dopamine $D_3$ receptor, and the representative compounds have good $D_3/D_2$ receptor selectivity, indicating that such compounds are less liable to produce side effects such as akathisia, extrapyramidal system effect (which are both caused by excessive blockage of $D_2$ receptor), catalepsy and the like, and possess potential effect of improving cognitive impairment. In addition, the compounds of the present invention have good affinity to 5-$HT_{1A}$ and 5-$HT_{2A}$ receptors, which further indicates that the compounds have effects of improving schizophrenic negative symptoms and cognition function, and thereby the anti-schizophrenia treatment spectrum is enlarged. It is demonstrated by in vivo tests in animals that I-1 and other representative compounds significantly improve relevant schizophrenic symptoms in the apomorphine and MK-801 mouse models. Thus, the compound of the present invention has good anti-schizophrenia effect. It is demonstrated by the preliminary researches on pharmacokinetics and safety that, the compounds of this class have a good oral absorption, and a lower acute toxicity ($LD_{50}$>2000 mg/Kg) than RGH-188 ($LD_{50}$=760 mg/Kg), and the results of bacterial reverse mutation tests are all negative. Therefore, the compound of the present invention has remarkable druggability, is liable to be used as novel anti-schizophrenia drugs, and is comparable to the prior art. Consequently, the present invention possesses novelty, inventiveness and substantive scientific progress.

The present invention is further described in details below by reference to the Examples. It is to be understood that this invention is not limited to the Examples.

EXAMPLE 1

Preparation of trans-N-(4-(2-(4-(benzo[d]isothiazol-3-yl)piperazin-1-yl)ethyl)cyclohexyl)furyl-2-carboxamide (I-1) and the salt thereof (1) Preparation of trans-N-tert-butoxycarbonyl-4-aminocyclohexylthanol (2)

Trans-N-tert-butoxycarbonyl-4-aminocyclohexylacetic acid (128.5 g, 0.5 mol) and dichloromethane (1 L) were added into a 4-neck flask (2 L), and cooled under ice bath to 0° C., followed by the dropwise addition of triethylamine (1.25 mol). Isopropyl chloroformate (0.6 mol) was slowly added dropwise at the temperature not exceeding 5° C., and then stirred at room temperature (RM) for 3 h and cooled to 5° C. Cold water (500 mL) was added and then stirred for 0.5 h. Layers were separated, and the organic layer was washed with saturated saline (400 mL×1), and evaporated to dryness. Under $N_2$ protection, anhydrous THF (1 L) was added to the residue, and the temperature was reduced to 0° C. $KBH_4$ (0.5 mol) was added slowly in portion at the temperature not exceeding 5° C., then stirred at RM for 3 h, and cooled below 5° C. Saturated ammonium chloride solution was slowly added dropwise until no bubbles were generated. The system was concentrated under reduced pressure to near dryness, and added with water (400 mL) and dichloromethane (500 mL) for distribution. The organic layer was washed sequentially with saturated $Na_2CO_3$ aqueous solution, water, and saturated saline, and evaporated to dryness, to give the intermediate trans-N-tert-butoxycarbonyl-4-aminocyclohxeylethanol (2) which was directly used for reaction in the next step.

(2) Preparation of trans-N-tert-butoxycarbonyl-4-aminocyclohexylethanol mesylate (3)

Trans-N-tert-butoxycarbonyl-4-aminocyclohexyl ethanol (2) (48.6 g, 0.2 mol), triethylamine (0.6 mol) and dichloromethane (500 mL) were added into a 4-neck flask (2 L), and cooled under ice-bath to 0° C. The solution of methane sulfonyl chloride (0.24 mol) in dichloromethane (200 mL) was slowly added dropwise, and then stirred at RM for 4 h. The reaction solution was washed sequentially with water (300 mL×2), 1% sodium hydroxide aqueous solution (300 mL×2), water (300 mL×1), and saturated saline (300 mL×1), evaporated to dryness, and recrystallized with 95% ethanol, to give an off white solid (52.1 g, yield 81%).

(3) Preparation of Intermediate tert-butyl trans-N-4-(2-(4-(benzo[d]isothiazol-3-yl)piperazin-1-yl)ethyl) cyclohexylcarbamate (4)

Intermediate (3) (32.1 g, 0.1 mol), 3-(piperazin-1-yl) benzo[d]isothiazole (19.9 g, 0.09 mol), anhydrous potassium carbonate (37.3 g, 0.27 mol) and DMF (500 mL) were added into a single neck flask (1 L), reacted overnight at 60° C. and filtered. The filter cake was washed with DMF (60 mL×2). The filtrate was combined and evaporated to dryness, and the residue was recrystallized with anhydrous ethanol, to give intermediate 4 (24.8 g, yield 62%).

(4) Preparation of Intermediate trans-4-(2-(4-(benzo[d]isothiazol-3-yl)piperazin-1-yl)ethyl)cyclohexylamine (5)

4 (50 mmol), and dichloromethane (200 mL) were added into a 3-neck flask (500 mL), and trifluoroacetic acid (35 mL) was slowly added dropwise, and stirred overnight at RM. The system was washed sequentially with water (200 mL×2), 5% sodium carbonate solution (150 mL×2), and saturated saline (200 mL×1). The organic layer was evaporated to dryness, to give a white solid (15.8 g, yield 91.7%).

(5) Preparation of the Target Compound I-1

Compound 5 (0.23 mmol), triethylamine (0.75 mL) and dichloromethane (20 mL) were added into a 3-neck flask (50 mL), and cooled under ice-bath to 0° C. The solution of furyl-2-formyl chloride (0.28 mmol) in dichloromethane was slowly added dropwise, and then stirred at RM for 4 h. The system was washed sequentially with saturated $Na_2CO_3$ aqueous solution (5 mL×1), water (5 mL×1), and saturated saline (5 mL×1), and evaporated to dryness, and the residue was recrystallized with 95% ethanol, to give a white solid I-1 (0.08 g, yield 79.4%).

$^1$H NMR (DMSO-d$^6$, δ: ppm): 0.98-1.07 (m, 2H, A-H), 1.16-1.38 (m, 3H, A-H), 1.49-1.50 (m, 2H, A-H), 1.75-1.78 (m, 4H, A-H), 2.75 (t, 2H, J=7.6 Hz, N—CH$_2$), 3.03-3.13 (m, 4H, piperazine-CH$_2$), 3.63-3.68 (m, 4H, piperazine-CH$_2$), 3.76-3.77 (m, 1H, A-H), 6.59 (d×d, 1H, J=8.0 Hz, 4.0 Hz, Ar—H), 7.06 (d, 1H, J=4.0 Hz, Ar—H), 7.46 (t, 1H, J=8.0 Hz, Ar—H), 7.58 (t, 1H, J=8.0 Hz, Ar—H), 8.03-8.08 (m, 2H, Ar—H), 8.23 (d, 1H, J=8.0 Hz, Ar—H).

ESI-MS: 439 [M+H$^+$]

(6) Preparation of the Hydrochloride of the Target Compound I-1

Compound I-1 (1.0 mmol), 5% hydrochloric acid (1.0 mmol) and methanol (10 mL) were added into a single neck flask (50 mL), and stirred at RM for 1 h, to provide a clear reaction solution. The system was evaporated to dryness, added with isopropanol (5 mL) and stirred for 3 h. A white solid was precipitated and filtered, and the filter cake was baked to dryness, and recrystallized with 95% ethanol, to give the white solid (0.42 g, yield 88.1%).

Elemental analysis: $C_{24}H_{30}N_4O_2S.HCl$ (theoretical value %: C, 60.68; H, 6.58; N, 11.79; experimental value %: C, 60.46; H, 6.79; N, 11.54).

(7) Preparation of the Hydrobromide of the Target Compound I-1

With compound I-1 (1.0 mmol) and 5% hydrobromic acid (1.0 mmol) as the starting materials, a white solid (0.45 g, yield 86.9%) was obtained in accordance with the method for preparing the hydrochloride of compound I-1.

Elemental analysis: $C_{24}H_{30}N_4O_2S.HBr$ (theoretical value %: C, 55.49; H, 6.01; N, 10.78; experimental value %: C, 55.62; H, 5.91; N, 10.89).

(8) Preparation of the Sulfate of the Target Compound I-1

With compound I-1 (0.5 mmol) and 5% sulfuric acid (0.25 mmol) as the starting materials, a white solid (0.14 g, yield 57.5%) was obtained in accordance with the method for preparing the hydrochloride of compound I-1.

Elemental analysis: $C_{24}H_{30}N_4O_2S.\frac{1}{2}SO_4$ (theoretical value %: C, 59.11; H, 6.41; N, 11.49; experimental value %: C, 59.30; H, 6.25; N, 11.28).

(9) Preparation of the Mesylate of the Target Compound I-1

With compound I-1 (1 mmol) and methanesulfonic acid (1 mmol) as the starting materials, a white solid (0.41 g, yield 76.7%) was obtained in accordance with the method for preparing the hydrochloride of compound I-1.

Elemental analysis: $C_{24}H_{30}N_4O_2S.CH_4O_3S$ (theoretical value %: C, 56.16; H, 6.41; N, 10.48; experimental value %: C, 56.01; H, 6.29; N, 10.62).

EXAMPLE 2

Preparation of trans-N-(4-(2-(4-(benzo[d]isothiazol-3-yl)piperazin-1-yl)ethyl)cyclohexyl)thienyl-2-carboxamide (I-2) and the salt thereof With intermediate 5 (0.29 mmol) and thienyl-2-formyl chloride (0.35 mmol) as the starting materials, target compound I-2 (0.09 g, yield 66.7%) was obtained in accordance with the method for preparing compound I-1.

$^1$H NMR (DMSO-d$^6$, δ: ppm): 0.99-1.07 (m, 2H, A-H), 1.11-1.18 (m, 5H, A-H), 1.78-1.86 (m, 4H, A-H), 2.39 (t, 2H, J=7.8 Hz, N—CH$_2$), 2.59-2.4 (m, 4H, piperazine-CH$_2$), 3.44-3.49 (m, 4H, piperazine-CH$_2$), 3.62-4.70 (m, 1H, A-H), 7.38 (d×d, 1H, J=8.0 Hz, 4.0 Hz, Ar—H), 7.44 (t, 1H, J=7.6 Hz, Ar—H), 7.56 (t, 1H, J=7.6 Hz, Ar—H), 7.71 (d, 1H, J=4.0 Hz, Ar—H), 8.04-8.07 (m, 2H, Ar—H), 8.21 (d, 1H, J=8.0 Hz, Ar—H).

ESI-MS: 455 [M+H$^+$]

Preparation of the Mesylate of Compound I-2

With compound I-2 (0.1 mmol) and methanesulfonic acid (0.1 mmol) as the starting materials, a white solid (0.05 g, yield 90.2%) was obtained in accordance with the method for synthesizing the hydrochloride of compound I-1.

Elemental analysis: $C_{24}H_{30}N_4OS_2.CH_4O_3S$ (theoretical value %: C, 54.52; H, 6.22; N, 10.17; experimental value %: C, 54.39; H, 6.41; N, 10.02).

Preparation of the Mesylate Hemihydrate of Compound I-2

Compound I-2 (0.1 mmol), methanesulfonic acid (0.1 mmol), water (1 mL) and methanol (20 mL) were added into a single neck flask (50 mL), and stirred at RM for 1 h, to provide a clear reaction solution. The reaction solution was evaporated to dryness, to provide an oil. Isopropanol (5 mL) was added and stirred for 2 h. A white solid was precipitated and filtered, and the filter cake was baked to dryness, and recrystallized with 95% ethanol, to give the white solid (0.046 g, yield 82.3%).

Elemental analysis: $C_{24}H_{30}N_4OS_2 \cdot CH_4O_3S \cdot \frac{1}{2}H_2O$ (theoretical value %: C, 53.64; H, 6.30; N, 10.01; experimental value %: C, 53.82; H, 6.19; N, 10.30).

EXAMPLE 3

Preparation of trans-N-(4-(2-(4-(benzo[d]isothiazol-3-yl)piperazin-1-yl)ethyl)cyclohexyl)-1H-pyrrolyl-2-carboxamide (I-3) and the salt thereof Compound 5 (0.52 mmol), pyrrolyl-2-formic acid (0.44 mmol) and $CH_2Cl_2$ (20 mL) were added into a 3-neck flask (50 mL), and cooled under ice bath to 0° C. The solution of 4-dimethylaminopyridine (0.35 mmol) and 1-ethyl-(3-dimethylaminopropyl)carbonyldiimino hydrochloride (0.52 mmol) in dichloromethane was slowly added dropwise, and then stirred at RM for 19 h. The system was washed sequentially with saturated $Na_2CO_3$ aqueous solution (5 mL×2), water (5 mL×1), and saturated saline (5 mL×1), and evaporated to dryness, and the residue was recrystallized with 95% ethanol to give a white solid I-3 (0.12 g, yield 62.5%).

$^1$H NMR (DMSO-d$^6$, δ: ppm): 1.00-1.06 (m, 2H, A-H), 1.19-1.32 (m, 3H, A-H), 1.43-1.47 (m, 2H, A-H), 1.48-1.81 (m, 4H, A-H), 2.66 (t, 2H, J=7.4 Hz, N—$CH_2$), 2.88-2.91 (m, 4H, piperazine-$CH_2$), 3.52-3.53 (m, 4H, piperazine-$CH_2$) 3.63-3.66 (m, 1H, A-H), 6.04-6.06 (d×d, 1H, J=3.2 Hz, J=2.4 Hz, Ar—H), 6.75-6.77 (m, 1H, Ar—H), 6.8-6.82 (m, 1H, Ar—H), 7.45 (t, 1H, J=8.0 Hz, Ar—H), 7.57 (t, 1H, J=8.0 Hz, Ar—H), 8.05-8.08 (m, 2H, Ar—H).

ESI-MS: 438 [M+H$^+$]

Preparation of the Hydrobromide of Compound I-3

With compound I-3 (0.1 mmol) and 5% hydrobromic acid (0.1 mmol) as the starting materials, a white solid (0.04 g, yield 91.3%) was obtained in accordance with the method for synthesizing the hydrochloride of compound I-1.

Elemental analysis: $C_{24}H_{31}N_5OS \cdot HBr$ (theoretical value %: C, 55.59; H, 6.22; N, 13.51; experimental value %: C, 55.8; H, 6.07; N, 13.76).

EXAMPLE 4

Preparation of trans-N-(4-(2-(4-(benzo[d]isothiazol-3-yl)piperazin-1-yl)ethyl)cyclohexyl)-1H-indolyl-2-carboxamide (I-4)

With intermediate 5 (0.58 mmol) and indolyl-2-formic acid (0.48 mmol) as the starting materials, target compound I-4 (0.09 g, yield 38.5%) was obtained in accordance with the method for preparing compound I-3.

$^1$H NMR (DMSO-d$^6$, δ: ppm): 1.05-1.1 (m, 2H, A-H), 1.24-1.45 (m, 5H, A-H), 1.81-1.90 (m, 4H, A-H), 2.41 (t, 2H, J=7.8 Hz, N—$CH_2$), 2.60-2.62 (m, 4H, piperazine-$CH_2$), 3.45-3.47 (m, 4H, piperazine-$CH_2$), 3.76-3.78 (m, 1H, A-H), 7.02-7.05 (m, 1H, Ar—H), 7.12 (s, 1H, Ar—H), 7.16-7.20 (m, 1H, Ar—H), 7.42-7.4 (m, 2H, Ar—H), 7.54-7.60 (m, 2H, Ar—H), 8.00-8.05 (m, 2H, Ar—H).

ESI-MS: 488 [M+H$^+$]

EXAMPLE 5

Preparation of trans-N-(4-(2-(4-(benzo[d]isothiazol-3-yl)piperazin-1-yl)ethyl)cyclohexyl)benzofuryl-2-carboxamide-5 and the salt thereof With intermediate 5 (1.0 mmol) and benzofuryl-2-formyl chloride (1.1 mmol) as the starting materials, target compound I-5 (0.39 g, yield 80.7%) was obtained in accordance with the method for preparing compound I-1.

$^1$H NMR (DMSO-d$^6$, δ: ppm): 1.07-1.12 (m, 2, A-H), 1.25-1.46 (m, 5H, A-H), 1.83-1.91 (m, 4H, A-H), 2.44 (t, 2, J=7.8 Hz, N—$CH_2$), 2.61-2.62 (m, 4H, piperazine-$CH_2$), 3.46-3.48 (m, 4H, piperazine-$CH_2$), 3.77-3.79 (m, 1H, A-H), 7.11-7.13 (m, 3H, Ar—H), 7.20 (s, 1H, Ar—H), 7.32-7.34 (m, 2H, Ar—H), 7.51-7.53 (m, 1H, Ar—H), 7.78-7.80 (m, 1H, Ar—H), 8.22-8.25 (m, 1H, Ar—H).

ESI-MS: 489 [M+H$^+$]

Preparation of the Hydrochloride of Compound I-5

With compound I-5 (0.2 mmol) and 5% hydrochloric acid (0.2 mmol) as the starting materials, a white solid (0.08 g, yield 76.3%) was obtained in accordance with the method for synthesizing the hydrochloride of compound I-1.

Elemental analysis: $C_{28}H_{32}N_4O_2S \cdot HCl$ (theoretical value %: C, 64.04; H, 6.33; N, 10.67; experimental value %: C, 64.28; H, 6.47; N, 10.51).

Preparation of the Trifluoroacetate of Compound I-5

With compound I-5 (0.2 mmol) and 5% trifluoracetic acid (0.2 mmol) as the starting materials, a white solid (0.10 g, yield 82.6%) was obtained in accordance with the method for synthesizing the hydrochloride of compound I-1.

Elemental analysis: $C_{28}H_{32}N_4O_2S \cdot CF_3CO_2H$ (theoretical value %: C, 59.79; H, 5.52; N, 9.30; experimental value %: C, 59.61; H, 5.67; N, 9.13).

EXAMPLE 6

Preparation of trans-N-(4-(2-(4-(benzo[d]isothiazol-3-yl)piperazin-1-yl)ethyl)cyclohexyl)benzo[b]thienyl-2-carboxamide (I-6)

With intermediate 5 (1.0 mmol) and benzo[b]thienyl-2-formyl chloride (1.1 mmol) as the starting materials, target compound I-6 (0.44 g, yield 87.0%) was obtained in accordance with the method for preparing compound I-1.

$^1$H NMR (DMSO-d$^6$, δ: ppm): 1.06-1.10 (m, 2H, A-H), 1.23-1.41 (m, 4H, A-H), 1.80-1.87 (m, 5H, A-H), 2.42 (t, 2H, J=7.8 Hz, N—$CH_2$?), 2.63-2.65 (m, 4H), piperazine-$CH_2$), 3.47-3.48 (m, 4H, piperazine-$CH_2$), 3.76-3.78 (m, 1H, A-H), 7.12 (d, 1H, J=8.0 Hz, Ar—H), 7.23 (m, 2H, Ar—H), 7.35-7.36 (m, 2H, Ar—H), 7.54-7.56 (m, 2H, Ar—H), 7.71 (s, 1H, Ar—H), 8.19-8.22 (m, 1H, Ar—H).

ESI-MS: 505 [M+H$^+$]

EXAMPLE 7

Preparation of trans-N-(4-(2-(4-(benzo[d]isothiazol-3-yl)piperazin-1-yl)ethyl)cyclohexyl)-5-cyano-furyl-2-carboxamide (I-7)

With intermediate 5 (1.0 mmol) and 5-cyano-furyl-2-formyl chloride (1.2 mmol) as the starting materials, target compound I-7 (0.40 g, yield 86.3%) was obtained in accordance with the method for preparing compound I-1.

$^1$H NMR (DMSO-d$^6$, δ: ppm): 1.01-1.09 (m, 2H, A-H), 1.19-1.40 (m, 3H, A-H), 1.52-1.53 (m, 2H, A-H), 1.77-1.81 (m, 4H, A-H), 2.78 (t, 2H, J=7.6 Hz, N—CH$_2$), 3.05-3.16 (m, 4H, piperazine-CH$_2$), 3.64-3.70 (m, 4H, piperazine-CH$_2$), 3.78-3.79 (m, 1H, A-H), 7.16 (d, 1H, J=8.0 Hz, Ar—H), 7.48-7.49 (m, 2H, Ar—H), 7.58 (t, 1H, J=0.0H-z, Ar—H), 8.25-8.27 (m, 2H, Ar—H).

ESI-MS: 464 [M+H$^+$]

EXAMPLE 8

Preparation of trans-N-(4-(2-(4-(benzo[d]isothiazol-3-yl)piperazin-1-yl)ethyl)cyclohexyl)-3-tert-butylfuryl-2-carboxamide (I-8) With intermediate 5 (1.0 mmol) and 3-tert-butylfuryl-2-formyl chloride (1.2 mmol) as the starting materials, target compound I-8 (0.38 g, yield 76.9%) was obtained in accordance with the method for preparing compound I-1.

$^1$H NMR (DMSO-d$^6$, δ: ppm): 0.97-1.05 (m, 2H, A-H), 1.12 (s, 9H, A-H), 1.13-1.40 (m, 3H, A-H), 1.50-1.52 (m, 3H, A-H), 1.76-1.78 (m, 3H, A-H), 2.74 (t, 2H, J=7.6 Hz, N—CH$_2$), 3.05-3.14 (m, 4H, piperazine-CH$_2$), 3.64-3.69 (m, 4H, piperazine-CH$_2$), 3.78-3.79 (m, 1H, A-H), 6.56 (d, 1H, J=8.0 Hz, Ar—H), 7.44 (t, 1H, J=8.0H, Ar—H), 7.57 (t, 1H, J=0.0 Hz, Ar—H), 8.01-8.05 (m, 2H, Ar—H), 8.20 (d, 1H, J=8.0 Hz, Ar—H).

ESI-MS: 495 [M+H$^+$]

EXAMPLE 9

Preparation of trans-N-(4-(2-(4-(benzo[d]isothiazol-3-yl)piperazin-1-yl)ethyl)cyclohexyl)-5-methyl-1H-pyrrolyl-2-carboxamide (I-9)

With intermediate 5 (1.0 mmol) and 5-methyl-1H-pyrrolyl-2-formyl chloride (1.2 mmol) as the starting materials, target compound I-9 (0.26 g, yield 57.6%) was obtained in accordance with the method for preparing compound I-1.

$^1$H NMR (DMSO-d$^6$, δ: ppm): 0.99-1.04 (m, 2H, A-H), 1.18-1.31 (m, 3H, A-H), 1.41-1.45 (m, 2H, A-H), 1.46-1.79 (m, 4H, A-H), 2.34 (s, 3H, A-H), 2.63 (t, 2H, J=7.4 Hz, N—CH$_2$), 2.86-2.89 (m, 4H, piperazine-CH$_2$), 3.51-3.52 (m, 4H, piperazine-CH$_2$) 3.62-3.64 (m, 1H, A-H), 6.01-6.03 (d, 1H, J=3.6 Hz, Ar—H), 7.32 (d, 1H, J=3.6 Hz, Ar—H), 7.43 (t, 1H, J=8.0 Hz, Ar—H), 7.55 (t, 1H, J=8.0 Hz, Ar—H), 8.02-8.06 (m, 2H, Ar—H).

ESI-MS: 452 [M+H$^+$]

EXAMPLE 10

Preparation of trans 5-acetyl-N-(4-(2-(4-(benzo[d]isothiazol-3-yl)piperazin-1-yl)ethyl)cyclohexyl)furyl-2-carboxamide (I-10)

With intermediate 5 (1.0 mmol) and 5-acetyl-furyl-2-formyl chloride (1.2 mmol) as the starting materials, target compound I-10 (0.33 g, yield 68.5%) was obtained in accordance with the method for preparing compound I-1.

$^1$H NMR (DMSO-d$^6$, δ: ppm): 1.01-1.09 (m, 2H, A-H), 1.18-1.40 (m, 3H, A-H), 1.51-1.52 (m, 2H, A-H), 1.76-1.79 (m, 4H, A-H), 2.77 (t, 2H, J=7.6 Hz, N—CH$_2$), 2.81 (s, 3H, A-H), 3.05-3.16 (m, 4H, piperazine-CH$_2$), 3.65-3.70 (m, 4H, piperazine-CH$_2$), 3.78-3.79 (m, 1H, A-H), 7.21 (d, 1H, J=8.0 Hz, Ar—H), 7.49 (m, 2H, Ar—H), 7.61 (t, 1H, J=8.0 Hz, Ar—H), 8.06-8.11 (m, 2H, Ar—H).

ESI-MS: 481 [M+H$^+$]

EXAMPLE 11

Preparation of trans-N-(4-(2-(4-(benzo[d]isothiazol-3-yl)piperazin-1-yl)ethyl)cyclohexyl)-3-methylthienyl-2-carboxamide (I-11)

With intermediate 5 (1.0 mmol) and 3-methylfuryl-2-formyl chloride (1.2 mmol) as the starting materials, target compound I-11 (0.41 g, yield 87.5%) was obtained in accordance with the method for preparing compound I-1.

$^1$H NMR (DMSO-d$^6$, δ: ppm): 0.97-1.05 (m, 2H, A-H), 1.10-1.16 (m, 4H, A-H), 1.76-1.5 (m, 5, A-H), 2.31 (s, 3H, A-H), 2.38 (t, 2H, J=7.6 Hz, N—CH$_2$) 2.58-2.62 (m, 4H, piperazine-CH$_2$), 3.43-3.47 (m, 4H, piperazine-CH$_2$) 3.60-4.69 (m, 1H, A-H), 7.35 (d, 1H, J=8.0 Hz, Ar—H), 7.42 (t, 1H, J=7.6 Hz, Ar—H), 7.54 (t, 1H, J=7.6 Hz, Ar—H), 8.03-8.05 (m, 2H, Ar—H), 8.19 (d, 1H, J=8.0 Hz, Ar—H).

ESI-MS: 469 [M+H$^+$]

EXAMPLE 12

Preparation of trans-N-(4-(2-(4-(benzo[d]isothiazol-3-yl)piperazin-1-yl)ethyl)cyclohexyl)-3-bromothienyl-2-carboxamide (I-12)

With intermediate 5 (1.0 mmol) and 3-bromothienyl-2-formyl chloride (1.1 mmol) as the starting materials, target compound I-12 (0.47 g, yield 87.7%) was obtained in accordance with the method for preparing compound I-1.

$^1$H NMR (DMSO-d$^6$, δ: ppm): 1.01-1.08 (m, 2H, A-H), 1.13-1.20 (m, 5H, A-H), 1.80-1.88 (m, 4H, A-H), 2.40 (t, 2H, J=7.8 Hz, N—CH$_2$), 2.60-2.65 (m, 4H, piperazine-CH$_2$), 3.45-3.50 (m, 4H, piperazine-CH$_2$), 3.64-4.72 (m, 1H, A-H), 742 (d, 1H, J=8.0 Hz, Ar—H), 7.46 (t, 1H, J=7.6 Hz, Ar—H), 7.5 (t, 1H, J=7.6 Hz, Ar—H), 8.08-8.12 (m, 2H, Ar—H), 8.32 (d, 1H, J=8.0 Hz, Ar—H).

ESI-MS: 533 [M+H$^+$]

EXAMPLE 13

Preparation of trans-N-(4-(2-(4-(benzo[d]isothiazol-3-yl)piperazin-1-yl)ethyl)cyclohexyl)-3-methylbenzo[b]thienyl-2-carboxamide (I-13)

With intermediate 5 (1.0 mmol) and 3-methylbenzo[b]thienyl-2-formyl chloride (1.2 mmol) as the starting materials, target compound I-13 (0.47 g, yield 87.7%) was obtained in accordance with the method for preparing compound I-1.

$^1$H NMR (DMSO-d$^6$, δ: ppm): 1.05-1.09 (m, 2H, A-H), 1.22-1.40 (m, 4H, A-H), 1.78-1.85 (m, 5H, A-H), 2.41 (t, 2H, J=7.8 Hz, N—CH$_2$), 2.55 (s, 3H, A-H), 2.62-2.64 (m, 4H, piperazine-CH$_2$), 3.46-3.48 (m, 4H, piperazine-CH$_2$), 3.74-3.77 (m, 1H, A-H), 7.09 (d, 1H, J=8.0 Hz, Ar—H), 7.20

(m, 2H, Ar—H), 7.33-7.34 (m, 2H, Ar—H), 7.52-7.54 (m, 2H, Ar—H), 8.17-8.21 (m, 1H, Ar—H).
ESI-MS: 519 [M+H$^+$]

EXAMPLE 14

Preparation of trans-N-(4-(2-(4-(benzo[d]isothiazol-3-yl)piperazin-1-yl)ethyl)cyclohexyl)-3-chlorobenzo[b]thienyl-2-carboxamide (I-14)

With intermediate 5 (1.0 mmol) and 3-chlorobenzo[b]thienyl-2-formyl chloride (1.2 mmol) as the starting materials, target compound I-14 (0.44 g, yield 81.6%) was obtained in accordance with the method for preparing compound I-1.

$^1$H NMR (DMSO-d$^6$, δ: ppm): 1.09-1.14 (m, 2H, A-H), 1.25-1.44 (m, 4H, A-H), 1.82-1.89 (m, 5H, A-H), 2.45 (t, 2H, J=7.6 Hz, N—CH$_2$), 2.66-2.68 (m, 4H, piperazine-CH$_2$), 3.49-3.50 (m, 4H, piperazine-CH$_2$), 3.77-3.80 (m, 1H, A-H), 7.21 (d, 1H, J=8.0 Hz, Ar—H), 7.34 (m, 2H, Ar—H), 7.46-7.48 (m, 2H, Ar—H), 7.67-7.69 (m, 2H, Ar—H), 8.32-8.34 (m, 1H, Ar—H).
ESI-MS: 539 [M+H$^+$]

EXAMPLE 15

Preparation of trans-N-(4-(2-(4-(benzo[d]isothiazol-3-yl)piperazin-1-yl)ethyl)cyclohexyl)-5-nitro-1H-indolyl-2-carboxamide (I-15)

With intermediate 5 (0.58 mmol) and 5-nitro-1H-indolyl-2-formic acid (0.48 mmol) as the starting materials, target compound I-15 (0.11 g, yield 41.2%) was obtained in accordance with the method for preparing compound I-3.

$^1$H NMR (DMSO-d$^6$, δ: ppm): 1.11-1.17 (m, 2H, A-H), 1.29-1.50 (m, 5H, A-H), 1.85-1.94 (m, 4H, A-H), 2.46 (t, 2H, J=7.6 Hz, N—CH$_2$), 2.65-2.67 (m, 4H, piperazine-CH$_2$), 3.51-3.53 (m, 4H, piperazine-CH$_2$), 3.82-3.84 (m, 1H, A-H), 7.49 (d, 1H, J=8.0 Hz, Ar—H), 7.52 (s, 1H, Ar—H), 7.61-7.63 (m, 2H, Ar—H), 7.82 (d, 1H, J=8.4 Hz, Ar—H), 8.10-8.12 (m, 2H, Ar—H), 8.64 (s, 1H, Ar—H).
ESI-MS: 533 [M+H$^+$]

EXAMPLE 16

Preparation of trans-N-(4-(2-(4-(benzo[d]isothiazol-3-yl)piperazin-1-yl)ethyl)cyclohexyl)-5-methoxyl-benzofuryl-2-carboxamide (I-16)

With intermediate 5 (1.0 mmol) and 5-methoxylbenzofuryl-2-formyl chloride (1.2 mmol) as the starting materials, target compound I-16 (0.39 g, yield 75.2%) was obtained in accordance with the method for preparing compound I-1.

$^1$H NMR (DMSO-d$^6$, δ: ppm): 1.05-1.10 (m, 2H, A-H), 1.23-1.44 (m, 5H, A-H), 1.80-1.89 (m, 4H, A-H), 2.42 (t, 2H, J=7.6 Hz, N—CH$_2$), 2.59-2.61 (m, 4H, piperazine-CH$_2$), 3.43-3.45 (m, 4H, piperazine-CH$_2$), 3.75-3.77 (m, 1H, A-H), 4.05 (s, 3H, A-H), 7.18 (d, 1H, J=0.0 Hz, Ar—H), 7.30-7.32 (m, 3H, Ar—H), 7.48 (t, 1H, J=0.0 Hz, Ar—H), 7.52 (t, 1H, J=7.6 Hz, Ar—H), 7.82-7.85 (m, 2H, Ar—H).
ESI-MS: 519 [M+H$^+$]

EXAMPLE 17

Preparation of trans-N-(4-(2-(4-(benzo[d]isothiazol-3-yl)piperazin-1-yl)ethyl)cyclohexyl)-2-(thien-2-yl)acetamide (I-17)

With intermediate 5 (1.0 mmol) and thienyl-2-acetyl chloride (1.2 mmol) as the starting materials, target compound I-17 (0.27 g, yield 58.6%) was obtained in accordance with the method for preparing compound I-1.

$^1$H NMR (DMSO-d$^6$, δ: ppm): 0.97-1.05 (m, 2H, A-H), 1.09-1.16 (m, 5H, A-H), 1.76-1.83 (m, 4H, A-H), 2.37 (t, 2H, J=7.8 Hz, N—CH$_2$), 2.56-2.62 (m, 4H, piperazine-CH$_2$), 3.42-3.48 (m, 6H, A-H), 3.60-3.68 (m, 1H, A-H), 7.35 (d×d, 1H, J=8.0 Hz, 4.0 Hz, Ar—H), 7.41 (t, 1H, J=7.6 Hz, Ar—H), 7.53 (t, 1H, J=7.6 Hz, Ar—H), 7.70 (d, 1H, J=4.0 Hz, Ar—H), 8.02-8.04 (m, 2H, Ar—H), 8.17 (d, 1H, J=8.0 Hz, Ar—H).
ESI-MS: 469 [M+H$^+$]

EXAMPLE 18

Preparation of trans-N-(4-(2-(4-(benzo[d]isothiazol-3-yl)piperazin-1-yl)ethyl)cyclohexyl)-2-(benzofuran-3-yl)acetamide (I-18)

With intermediate 5 (1.0 mmol) and benzofuryl-3-acetyl chloride (1.2 mmol) as the starting materials, target compound I-18 (0.32 g, yield 64.1%) was obtained in accordance with the method for preparing compound I-1.

$^1$H NMR (DMSO-d$^6$, δ: ppm): 1.04-1.09 (m, 2H, A-H), 1.22-1.42 (m, 5H, A-H), 1.81-1.89 (m, 4H, A-H), 2.41 (t, 2H, J=7.8 Hz, N—CH$_2$), 2.58-2.59 (m, 4H, piperazine-CH$_2$), 3.43-3.45 (m, 4H, piperazine-CH$_2$), 3.75-3.77 (m, 1H, A-H), 4.02 (s, 2H, A-H), 7.09-7.12 (m, 3H, Ar—H), 7.30-7.32 (m, 2H, Ar—H), 7.50-7.52 (m, 1H, Ar—H), 7.75-7.87 (m, 1H, Ar—H), 7.91 (s, 1H, Ar—H), 8.23-8.26 (m, 1H, Ar—H).
ESI-MS: 503 [M+H$^+$]

EXAMPLE 19

Preparation of cis-N-(4-(2-(4-(benzo[d]isothiazol-3-yl)piperazin-1-yl)ethyl)cyclohexyl)furyl-2-carboxamide (I-19) and the salt thereof (1) Preparation of Intermediate 7

Cis-4-acetylaminocyclohexylacetic acid (6) (1.0 mol), 95% ethanol (1 L), and concentrated hydrochloric acid (300 mL) were added into a single neck flask (2 L), refluxed overnight, and evaporated to dryness. Anhydrous ethanol (500 mL) was added to the residue, evaporated to dryness, neutralized with triethylamine (300 mL), and added with acetone (1.5 L). The system was cooled to 0° C., and then the solution of tert-butoxyformic anhydride (1.2 mol) in acetone was slowly added dropwise, stirred for 30 h, and evaporated to dryness. The residue was stirred in 80% ethanol (250 mL), and filtered, and the filter cake was washed with water to give the intermediate 7 (203 g, yield 87.7%).

(2) Preparation of Intermediate 11

Intermediate 11 was prepared from intermediate 7 by the same method as the method for preparing intermediate 5 from material 1 in scheme one.

(3) Preparation of I-19

With intermediate 11 (0.1 mol) and furyl-2-formyl chloride (0.12 mol) as the starting materials, target compound I-19 (32.06 g, yield 73.1%) was obtained in accordance with the method for preparing compound I-1.

$^1$H NMR (DMSO-d$^6$, δ: ppm): 1.03-1, 12 (m, 2H, A-H), 1.21-1.53 (m, 3H, A-H), 1.54-1.55 (m, 2H, A-H), 1.80-1.83 (m, 4H, A-H), 2.81 (t, 2H, J=7.0 Hz, N—CH$_2$), 3.08-3.18 (m, 4H, piperazine-CH$_2$), 3.68-3.73 (m, 4H, piperazine-CH$_2$), 3.80-3.81 (m, 1H, A-H), 6.63 (d×d, 1H, J=8.0 Hz, 4.0 Hz, Ar—H), 7.11 (d, 1H, J=4.0 Hz, Ar—H), 7.50 (t, 1H, J=8.0 Hz, Ar—H), 7.62 (t, 1H, J=8.0 Hz, Ar—H), 8.07-8.12 (m, 2H, Ar—H), 8.28 (d, 1H, J=8.0 Hz, Ar—H).

ESI-MS: 439 [M+H$^+$]

(4) Preparation of the Hydrochloride of Compound I-19

With compound I-19 (1 mmol) and 5% hydrochloric acid (1 mmol) as the starting materials, a white solid (0.40 g, yield 83.9%) was obtained in accordance with the method for preparing the hydrochloride of compound compound I-1.

Elemental analysis: $C_{24}H_{30}N_4O_2S\cdot HCl$ (theoretical value %: C, 60.68; H, 6.58; N, 11.79; experimental value %: C, 60.77; H, 6.36; N, 11.91).

EXAMPLE 20

Preparation of cis-N-(4-(2-(4-(benzo[d]isothiazol-3-yl)piperazin-1-yl)ethyl)cyclohexyl)thienyl-2-carboxamide (I-20)

With intermediate 11 (1.0 mmol) and thienyl-2-formyl chloride (1.2 mmol) as the starting materials, target compound I-20 (0.32 g, yield 70.1%) was obtained in accordance with the method for preparing compound I-1.

$^1$H NMR (DMSO-d$^6$, δ: ppm): 1.03-1.12 (m, 2H, A-H), 1.15-1.22 (m, 5H, A-H), 1.83-1.91 (m, 4H, A-H), 2.43 (t, 2H, J=7.8 Hz, N—CH$_2$), 2.63-2.68 (m, 4H, piperazine-CH$_2$), 3.47-3.42 (m, 4H, piperazine-CH$_2$), 3.65-4.73 (m, 1H, A-H), 7.42 (d×d, 1H, J=8.0 Hz, 4.0 Hz, Ar—H), 7.48 (t, 1H, J=7.6 Hz, Ar—H), 7.59 (t, 1H, J=7.6 Hz, Ar—H), 7.74 (d, 1H, J=4.0 Hz, Ar—H), 8.04-8.07 (m, 2H, r-H), 8.24 (d, 1H, J=8.0 Hz, Ar—H).

ESI-MS: 455 [M+H$^+$]

EXAMPLE 21

Preparation of cis-N-(4-(2-(4-(benzo[d]isothiazol-3-yl)piperazin-1-yl)ethyl)cyclohexyl)-1H-pyrrolyl-2-carboxamide (I-21)

With intermediate 11 (1.0 mmol) and pyrrolyl-2-formic acid (0.85 mmol) as the starting materials, target compound I-21 (0.28 g, yield 75.2%) was obtained in accordance with the method for preparing compound I-3.

$^1$H NMR (DMSO-d$^6$, δ: ppm): 1.06-1.12 (m, 2H, A-H), 1.25-1.38 (m, 3H, A-H), 1.48-1.52 (m, 2H, A-H), 1.53-1.86 (m, 4H, A-H), 2.73 (t, 2H, J=7.4 Hz, N—CH$_2$), 2.94-2.97 (m, 4H, piperazine-CH$_2$), 3.57-3.58 (m, 4H, piperazine-CH$_2$) 3.68-3.71 (m, 1H, A-H), 6.10-6.12 (d×d, 1H, J=3.2 Hz, J=2.4 Hz, Ar—H), 6.81-6.83 (m, 1H, Ar—H), 6.87-6.88 (m, 1H, Ar—H), 7.51 (t, 1H, J=8.0 Hz, Ar—H), 7.63 (t, 1H, J=0.0H-z, Ar—H), 8.11-8.13 (m, 2H, Ar—H).

ESI-MS: 438 [M+H$^+$]

EXAMPLE 22

Preparation of cis-N-(4-(2-(4-(benzo[d]isothiazol-3-yl)piperazin-1-yl)ethyl)cyclohexyl)-1H-indolyl-2-carboxamide (I-22)

With intermediate 11 (0.58 mmol) and indolyl-2-formic acid (0.48 mmol) as the starting materials, target compound I-22 (0.12 g, yield 51.3%) was obtained in accordance with the method for preparing compound I-3.

$^1$H NMR (DMSO-d$^6$, δ: ppm): 1.12-1.18 (m, 2H, A-H), 1.31-1.52 (m, 5H, A-H), 1.88-1.96 (m, 4H, A-H), 2.50 (t, 2H, J=7.8 Hz, N—CH$_2$), 2.67-2.69 (m, 4H, piperazine-CH$_2$), 3.52-3.54 (m, 4H, piperazine-CH$_2$), 3.83-3.86 (m, 1H, A-H), 7.09-7.11 (m, 1H, Ar—H), 7.18 (s, 1H, Ar—H), 7.22-7.27 (m, 1H, Ar—H), 7.48-7.53 (m, 2H, Ar—H), 7.61-7.67 (m, 2H, Ar—H), 8.07-8.13 (m, 2H, Ar—H).

ESI-MS: 488 [M+H$^+$]

EXAMPLE 23

Preparation of cis-N-(4-(2-(4-(benzo[d]isothiazol-3-yl)piperazin-1-yl)ethyl)cyclohexyl)benzofuryl-2-carboxamide (I-23)

With intermediate 11 (1.0 mmol) and benzofuryl-2-formyl chloride (1.1 mmol) as the starting materials, target compound I-23 (0.36 g, yield 74.5%) was obtained in accordance with the method for preparing compound I-1.

$^1$H NMR (DMSO-d$^6$, δ: ppm): 1.10-1.15 (m, 2H, A-H), 1.28-1.49 (m, 5H, A-H), 1.86-1.94 (m, 4H, A-H), 2.47 (t, 2, J=7.8 Hz, N—CH$_2$), 2.64-2.65 (m, 4H, piperazine-CH$_2$), 3.49-3.51 (m, 4H, piperazine-CH$_2$), 3.80-3.82 (m, 1H, A-H), 7.14-7.16 (m, 3H, Ar—H), 7.23 (s, 1H, Ar—H), 7.35-7.37 (m, 2H, Ar—H), 7.54-7.56 (m, 1H, Ar—H), 7.82-7.84 (m, 1H, Ar—H), 8.26-8.29 (m, 1H, Ar—H).

ESI-MS: 489 [M+H$^+$]

EXAMPLE 24

Preparation of cis-N-(4-(2-(4-(benzo[d]isothiazol-3-yl)piperazin-1-yl)ethyl)cyclohexyl)benzo[b]thienyl-2-carboxamide (I-24)

With intermediate 11 (1.0 mmol) and benzo[b]thienyl-2-formyl chloride (1.1 mmol) as the starting materials, target compound I-24 (0.39 g, yield 77.1%) was obtained in accordance with the method for preparing compound I-1.

$^1$H NMR (DMSO-d$^6$, δ: ppm): 1.12-1.16 (m, 2H, A-H), 1.29-1.47 (m, 4H, A-H), 1.86-1.93 (m, 5H, A-H), 2.47 (t, 2H, J=7.8 Hz, N—CH$_2$), 2.68-2.70 (m, 4H, piperazine-CH$_2$), 3.52-3.53 (m, 4H, piperazine-CH$_2$), 3.82-3.84 (m, 1H, A-H), 7.18 (d, 1H, J=8.0 Hz, Ar—H), 7.29 (m, 2H, Ar—H), 7.40-7.41 (m, 2H, Ar—H), 7.59-7.61 (m, 2H, Ar—H), 7.76 (s, 1H, Ar—H), 8.25-8.26 (m, 1H, Ar—H).

ESI-MS: 505 [M+H$^+$]

EXAMPLE 25

Preparation of trans-N-(4-(2-(4-(benzo[d]isothiazol-3-yl)piperazin-1-yl)ethyl)cyclohexyl)thienyl-2-sulfamide (□-1) and the salt thereof With intermediate 5 (2.9 mmol) and thienyl-2-sulfonyl chloride (3.5 mmol) as the starting materials, target compound □-1 (0.5 g, yield 35.2%) was obtained in accordance with the method for preparing compound I-1.

$^1$H NMR (DMSO-d$^6$, δ: ppm): 0.93-0.98 (m, 2H, A-H), 1.17-1.25 (m, 3H, A-H), 1.55-1.60 (m, 2H, A-H), 1.66-1.71 (m, 4H, A-H), 2.69 (t, 2H, J=7.8 Hz, N—CH$_2$), 2.94-2.98 (m, 1H, A-H), 3.11-3.14 (m, 4H, piperazine-CH$_2$), 3.41-3.44 (m, 4H, piperazine-CH$_2$), 7.21 (t, 1H, J=4.0 Hz, Ar—H), 7.52 (t, 1H, J=8.0 Hz, Ar—H), 7.62-7.65 (m, 2H, Ar—H), 7.87 (d, 1H, J=4.0 Hz, Ar—H), 8.0-8.12 (m, 2H, Ar—H).

ESI-MS: 491 [M+H$^+$]

Preparation of the Hydrobromide of Compound □-1

With compound □-1 (1 mmol) and 5% hydrobromic acid (1 mmol) as the starting materials, a white solid (0.48 g, yield 83.4%) was obtained in accordance with the method for preparing the hydrochloride of compound I-1.

Elemental analysis: $C_{24}H_{30}N_4O_2S_3 \cdot HBr$ (theoretical value %: C, 48.33; H, 5.47; N, 9.80; experimental value %: C, 48.51; H, 5.62; N, 9.57).

Preparation of the Sulfate of Compound □-1

With compound □-1 (0.5 mmol) and 5% sulfuric acid (0.25 mmol) as the starting materials, a white solid (0.16 g, yield 58.8%) was obtained in accordance with the method for preparing the hydrochloride of compound I-1.

Elemental analysis: $C_{24}H_{30}N_4O_2S_3 \cdot \frac{1}{2}H_2SO_4$ (theoretical value %: C, 51.18; H, 5.79; N, 10.38; experimental value %: C, 51.02; H, 5.96; N, 10.14).

EXAMPLE 26

Preparation of trans-N-(4-(2-(4-(benzo[d]isothiazol-3-yl)piperazin-1-yl)ethyl)cyclohexyl)-1H-pyrrolyl-3-sulfamide (□-2)

With intermediate 5 (1.0 mmol) and pyrrolyl-3-sulfonyl chloride (1.2 mmol) as the starting materials, target compound □-2 (0.30 g, yield 62.7%) was obtained in accordance with the method for preparing compound I-1.

$^1$H NMR (DMSO-d$^6$, δ: ppm): 0.98-1.13 (m, 2H, A-H), 1.24-1.31 (m, 3H, A-H), 1.59-1.64 (m, 2H, A-H), 1.71-1.76 (m, 4H, A-H), 2.71 (t, 2H, J=7.8 Hz, N—CH$_2$), 2.99-3.01 (m, 1H, A-H), 3.16-3.19 (m, 4H, piperazine-CH$_2$) 3.47-3.50 (m, 4H, piperazine-CH$_2$), 6.14-6.16 (d, 1H, J=0.4 Hz, Ar—H), 0.8-6.88 (m, 2H, Ar—H), 7.51 (t, 1H, J=8.0 Hz, Ar—H), 7.60 (t, 1H, J=8.0 Hz, Ar—H), 8.07-8.10 (m, 2H, Ar—H).

ESI-MS: 474 [M+H$^+$]

EXAMPLE 27

Preparation of trans-N-(4-(2-(4-(benzo[d]isothiazol-3-yl)piperazin-1-yl)ethyl)cyclohexyl)furyl-2-sulfamide (□-3)

With intermediate 5 (1.0 mmol) and furyl-2-sulfonyl chloride (1.2 mmol) as the starting materials, target compound □-3 (0.28 g, yield 59.7%) was obtained in accordance with the method for preparing compound I-1.

$^1$H NMR (DMSO-d$^6$, δ: ppm): 0.92-0.97 (m, 2H, A-H), 1.16-1.24 (m, 3H, A-H), 1.54-1.59 (m, 2H, A-H), 1.64-1.69 (m, 4H, A-H), 2.67 (t, 2H, J=7.8 Hz, N—CH$_2$), 2.93-2.97 (m, 1H, A-H), 3.09-3.13 (m, 4H, piperazine-CH$_2$), 3.40-3.43 (m, 4H, piperazine-CH$_2$), 7.19 (t, 1H, J=4.0 Hz, Ar—H), 7.51 (t, 1H, J=8.0 Hz, Ar—H), 7.64-7.67 (m, 2H, Ar—H), 7.89 (d, 1H, J=40 Hz, Ar—H), 8.07-8.13 (m, 2H, Ar—H).

ESI-MS: 475 [M+H$^+$]

EXAMPLE 28

Preparation of trans-N-(4-(2-(4-(benzo[d]isothiazol-3-yl)piperazin-1-yl)ethyl)cyclohexyl)benzo[b]thienyl-2-sulfamide (□-4)

With intermediate 5 (1.0 mmol) and benzo[b]thienyl-2-sulfonyl chloride (1.2 mmol) as the starting materials, target compound □-4 (0.39 g, yield 7.4%) was obtained in accordance with the method for preparing compound I-1.

$^1$H NMR (DMSO-d$^6$, δ: ppm): 1.01-1.05 (m, 2H, A-H), 1.18-1.36 (m, 4H, A-H), 1.75-1.82 (m, 5H, A-H), 2.37 (t, 2H, J=7.8 Hz, N—CH$_2$), 2.95-2.98 (m, 1H, A-H), 3.15-3.18 (m, 4H, piperazine-C-2), 3.45-3.48 (m, 4H, piperazine-CH$_2$), 7.08 (d, 1H, J=8.0 Hz, Ar—H), 7.19 (m, 2H, Ar—H), 7.31-7.32 (m, 2H, Ar—H), 7.50-7.52 (m, 2H, Ar—HT), 7.69 (s, 1H, Ar—H), 8.16-8.19 (m, 1H, Ar—H).

ESI-MS: 541 [M+H$^+$]

EXAMPLE 29

Preparation of trans-N-(4-(2-(4-(benzo[d]isothiazol-3-yl)piperazin-1-yl)ethyl)cyclohexyl)benzofuryl-2-sulfamide (□-5) and the salt thereof With intermediate 5 (1.0 mmol) and benzofuryl-2-sulfonyl chloride (1.2 mmol) as the starting materials, target compound □-5 (0.36 g, yield 68.1%) was obtained in accordance with the method for preparing compound I-1.

$^1$H NMR (DMSO-d$^6$, δ: ppm): 1.03-1.08 (m, 2H, A-H), 1.21-1.42 (m, 5H, A-H), 1.79-1.87 (m, 4H, A-H), 2.40 (t, 2H, J=7.8 Hz, N—CH$_2$), 2.93-2.96 (m, 1H, A-H), 3.13-3.16 (m, 4H, piperazine-CH$_2$), 3.43-3.46 (m, 4H, piperazine-CH$_2$), 7.14-7.16 (m, 3H, H, 7.23 (s, 1H, Ar—H), 7.34-7.36 (m, 2H, Ar—H), 7.54-7.56 (m, 1H, Ar—H), 7.81-7.83 (m, 1H, Ar—H), 8.25-8.26 (m, 1H, Ar—H).

ESI-MS: 525 [M+H$^+$]

Preparation of the Hydrochloride of Compound □-5

With compound □-5 (0.2 mmol) and 5% HCl (0.2 mmol) as the starting materials, a white solid (0.10 g, yield 88.3%) was obtained in accordance with the method for preparing the hydrochloride of compound I-1.

Elemental analysis: $C_{27}H_{32}N_4O_3S_2 \cdot HCl$ (theoretical value %: C, 57.79; H, 5.93; N, 9.98; experimental value %: C, 57.58; H, 5.72; N, 9.86).

Preparation of the Trifluoroacetate of Compound □-5

With compound □-5 (0.2 mmol) and 5% trifluoroacetic acid (0.2 mmol) as the starting materials, a white solid (0.10 g, yield 81.6%) was obtained in accordance with the method for preparing the hydrochloride of compound I-1.

Elemental analysis: $C_{27}H_{32}N_4O_3S_2 \cdot CF_3CO_2H$ (theoretical value %: C, 54.53; H, 5.21; N, 8.77; experimental value %: C, 54.72; H, 5.03; N, 8.64).

EXAMPLE 30

Preparation of trans-N-(4-(2-(4-(benzo[d]isothiazol-3-yl)piperazin-1-yl)ethyl)cyclohexyl)-1H-indolyl-3-sulfamide (□-6)

With intermediate 5 (1.0 mmol) and indolyl-3-sulfonyl chloride (1.2 mmol) as the starting materials, target compound □-6 (0.22 g, yield 42.3%) was obtained in accordance with the method for preparing compound I-1.

$^1$H NMR (DMSO-d$^6$, δ: ppm): 0.94-0.99 (m, 2H, A-H), 1.18-1.2 (m, 3H, A-H), 1.56-1.61 (m, 2H, A-H), 1.67-1.72 (m, 4H, A-H), 2.70 (t, 2H, J=7.8 Hz, N—CH$_2$), 2.95-2.99 (m, 1H, A-H), 3.12-3.15 (m, 4H, piperazine-CH$_2$), 3.42-3.45 (m, 4H, piperazine-CH$_2$), 7.02-7.03 (m, 2H, Ar—H), 7.23 (t, 1H, J=8.0 Hz, Ar—H), 7.54 (t, 1H, J=8.0 Hz, Ar—H), 7.58

(d, 1H, J=4.0 Hz, Ar—H), 7.61 (s, 1H, Ar—H), 7.90 (d, 1H, J=4.0 Hz, Ar—H), 8.06-8.12 (m, 2H, Ar—H).
ESI-MS: 524 [M+H$^+$]

EXAMPLE 31

Preparation of trans-N-(4-(2-(4-(benzo[d]isothiazol-3-yl)piperazin-1-yl)ethyl)cyclohexyl)-5-cyanofuryl-2-sulfamide (□-7)

With intermediate 5 (1.0 mmol) and 5-cyanofuryl-2-sulfonyl chloride (1.2 mmol) as the starting materials, target compound □-7 (0.39 g, yield 78.6%) was obtained in accordance with the method for preparing compound I-1.
$^1$H NMR (DMSO-d$^6$, δ: ppm): 0.95-1.00 (m, 2H, A-H), 1.19-1.27 (m, 3H, A-H), 1.57-1.62 (m, 2H, A-H), 1.67-1.72 (m, 4H, A-H), 2.70 (t, 2H, J=7.8 Hz, N—CH$_2$), 2.97-3.01 (m, 1H, A-H), 3.12-3.16 (m, 4H, piperazine-CH$_2$), 3.43-3.46 (m, 4H, piperazine-CH$_2$), 7.24 (d, 1H, J=8.0 Hz, Ar—H), 7.56-7.57 (m, 2H, Ar—H), 7.66 (t, 1H, J=8.0 Hz, Ar—H), 8.33-8.35 (m, 2H, Ar—H).
ESI-MS: 500 [M+H$^+$]

EXAMPLE 32

Preparation of trans-N-(4-(2-(4-(benzo[d]isothiazol-3-yl)piperazin-1-yl)ethyl)cyclohexyl)-5-chlorofuryl-2-sulfamide (□-8)

With intermediate 5 (1.0 mmol) and 5-chlorofuryl-2-sulfonyl chloride (1.2 mmol) as the starting materials, target compound □-8 (0.27 g, yield 53.3%) was obtained in accordance with the method for preparing compound I-1.
$^1$H NMR (DMSO-d$^6$, δ: ppm): 0.94-0.99 (m, 2H, A-H), 1.18-1.26 (m, 3H, A-H), 1.56-1.61 (m, 2H, A-H), 1.66-1.71 (m, 4H, A-H), 2.69 (t, 2H, J=7.8 Hz, N—CH$_2$), 2.95-2.99 (m, 1H, A-H), 3.11-3.15 (m, 4H, piperazine-CH$_2$), 3.42-3.45 (m, 4H, piperazine-CH$_2$), 7.22 (d, 1H, J=0.0 Hz, Ar—H), 7.54-7.55 (m, 2H, Ar—H), 7.63 (t, 1H, J=8.0 Hz, Ar—H), 8.31-8.33 (m, 2H, Ar—H).
ESI-MS: 509 [M+H$^+$]

EXAMPLE 33

Preparation of trans-N-(4-(2-(4-(benzo[d]isothiazol-3-yl)piperazin-1-yl)ethyl)cyclohexyl)-5-methylfuryl-2-sulfamide (□-9)

With intermediate 5 (1.0 mmol) and 5-methylfuryl-2-sulfonyl chloride (1.2 mmol) as the starting materials, target compound □-9 (0.29 g, yield 59.6%) was obtained in accordance with the method for preparing compound I-1.
$^1$H NMR (DMSO-d$^6$, δ: ppm): 0.91-0.96 (m, 2H, A-H), 1.14-1.22 (m, 3H, A-H), 1.53-1.58 (m, 2H, A-H), 1.63-1.68 (m, 4H, A-H), 2.41 (m, 3H, A-H), 2.64 (t, 2H, J=7.8 Hz, N—CH$_2$), 2.91-2.95 (m, 1H, A-H), 3.07-3.12 (m, 4H, piperazine-CH$_2$), 3.38-3.42 (m, 4H, piperazine-CH$_2$), 7.08 (d, 1H, J=8.0 Hz, Ar—H), 7.40-7.41 (m, 2H, Ar—H), 7.49 (t, 1H, J=0.0 Hz, Ar—H), 8.17-8.19 (m, 2H, Ar—H).
ESI-MS: 489 [M+H$^+$]

EXAMPLE 34

Preparation of trans-N-(4-(2-(4-(benzo[d]isothiazol-3-yl)piperazin-1-yl)ethyl)cyclohexyl)-5-tert-butylthienyl-2-sulfamide (□-10)

With intermediate 5 (1.0 mmol) and 5-tert-butylthienyl-2-sulfonyl chloride (1.2 mmol) as the starting materials, target compound □-10 (0.18 g, yield 32.5%) was obtained in accordance with the method for preparing compound I-1.
$^1$H NMR (DMSO-d$^6$, δ: ppm): 0.90-0.95 (m, 2H, A-H), 1.14-1.22 (m, 3H, A-H), 1.47 (s, 9H, A-H), 1.53-1.57 (m, 2H, A-H), 1.63-1.68 (m, 4H, A-H), 2.66 (t, 2H, J=7.8 Hz, N—CH$_2$), 2.91-2.95 (m, 1H, A-H), 3.08-3.11 (m, 4H, piperazine-CH$_2$), 3.38-3.41 (m, 4H, piperazine-CH$_2$), 7.06 (d, 1H, J=8.0 Hz, Ar—H), 7.38-7.39 (m, 2H, Ar—H), 7.47 (t, 1H, J=8.0 Hz, Ar—H), 8.15-8.17 (m, 2H, Ar—H).
ESI-MS: 547 [M+H$^+$]

EXAMPLE 35

Preparation of trans-N-(4-(2-(4-(benzo[d]isothiazol-3-yl)piperazin-1-yl)ethyl)cyclohexyl)-5-chlorobenzo[b]thienyl-2-sulfamide (□-11)

With intermediate 5 (1.0 mmol) and 5-chlorobenzo[b]thienyl-2-sulfonyl chloride (1.2 mmol) as the starting materials, target compound □-11 (0.23 g, yield 39.4%) was obtained in accordance with the method for preparing compound I-1.
$^1$H NMR (DMSO-d$^6$, δ: ppm): 1.05-1.09 (m, 2H, A-H), 1.22-1.40 (m, 4H, A-H), 1.79-1.86 (m, 5H, A-H), 2.41 (t, 2H, J=7.8 Hz, N—CH$_2$), 2.99-3.02 (m, 1H, A-H), 3.19-3.22 (m, 4H, piperazine-CH$_2$), 3.49-3.52 (m, 4H, piperazine-CH$_2$), 7.32 (d, 1H, J=8.0 Hz, Ar—H), 7.35 (s, 1H, Ar—H), 7.44-7.46 (m, 2H, Ar—H), 7.65 (d, 1H, J=8.4 Hz, Ar—H), 7.93-7.95 (m, 2H, Ar—H), 8.47 (s, 1H, Ar—H).
ESI-MS: 575 [M+H$^+$]

EXAMPLE 36

Preparation of trans-N-(4-(2-(4-(benzo[d]isothiazol-3-yl)piperazin-1-yl)ethyl)cyclohexyl)-5-cyanobenzo[b]thienyl-2-sulfamide (□-12)

With intermediate 5 (1.0 mmol) and 5-cyanobenzo[b]thienyl-2-sulfonyl chloride (1.2 mmol) as the starting materials, target compound □-12 (0.34 g, yield 60.7%) was obtained in accordance with the method for preparing compound I-1.
$^1$H NMR (DMSO-d$^6$, δ: ppm): 1.10-1.14 (m, 2H, A-H), 1.27-1.45 (m, 4H, A-H), 1.84-1.91 (m, 5H, A-H), 2.46 (t, 2H, J=7.8 Hz, N—CH$_2$), 3.04-3.07 (m, 1H, A-H), 3.24-3.27 (m, 4H, piperazine-CH$_2$), 3.54-3.57 (m, 4H, piperazine-CH$_2$), 7.37 (d, 1H, J=0.0 Hz, Ar—H), 7.41 (s, 1H, Ar—H), 7.51-7.53 (m, 2H, Ar—H), 7.70 (d, 1H, J=8.4 Hz, Ar—H), 7.98-8.01 (m, 2H, Ar—H), 8.53 (s, 1H, Ar—H).
ESI-MS: 566 [M+H$^+$]

EXAMPLE 37

Preparation of trans-N-(4-(2-(4-(benzo[d]isothiazol-3-yl)piperazin-1-yl)ethyl)cyclohexyl)-5-methylbenzo[b]thienyl-2-sulfamide (□-13)

With intermediate 5 (1.0 mmol) and 5-cyanobenzo[b]thienyl-2-sulfonyl chloride (1.2 mmol) as the starting materials, target compound □-13 (0.34 g, yield 60.7%) was obtained in accordance with the method for preparing compound I-1.
$^1$H NMR (DMSO-d$^6$, δ: ppm): 0.99-1.03 (m, 2H, A-H), 1.16-1.34 (m, 4H, A-H), 1.73-1.80 (m, 5H, A-H), 2.28 (s, 3H, A-H), 2.35 (t, 2H, J=7.8 Hz, N—CH$_2$), 2.93-2.96 (m, 1H, A-H), 3.13-3.16 (m, 4H, piperazine-CH$_2$), 3.43-3.46 (m, 4H, piperazine-CH$_2$), 7.26 (d, 1H, J=8.0 Hz, Ar—H), 7.29

(s, 1H, Ar—H), 7.38-7.40 (m, 2H, Ar—H), 7.59 (d, 1H, J=8.4H-z, Ar—H), 7.87-7.89 (m, 2H, Ar—H), 8.41 (s, 1H, Ar—H).
ESI-MS: 555 [M+H+]

EXAMPLE 38

Preparation of trans-N-(4-(2-(4-(benzo[d]isothiazol-3-yl)piperazin-1-yl)ethyl)cyclohexyl)-5-nitrobenzo[b]thienyl-2-sulfamide (□-14)

With intermediate 5 (1.0 mmol) and 5-nitrobenzo[b]thienyl-2-sulfonyl chloride (1.2 mmol) as the starting materials, target compound □-14 (0.29 g, yield 49.2%) was obtained in accordance with the method for preparing compound I-1.
$^1$H NMR (DMSO-d$^6$, δ: ppm): 1.14-1.1 (m, 2H, A-H), 1.31-1.49 (m, 4H, A-H), 1.88-1.95 (m, 5H, A-H), 2.50 (t, 2H, J=7.8 Hz, N—CH$_2$), 3.08-3.11 (m, 1H, A-H), 3.28-3.31 (m, 4H, piperazine-CH$_2$), 3.58-3.61 (m, 4H, piperazine-CH$_2$), 7.41 (d, 1H, J=8.0 Hz, Ar—H), 7.45 (s, 1H, Ar—H), 7.55-7.57 (m, 2H, Ar—H), 7.75 (d, 1H, J=8.4 Hz, Ar—H), 8.02-8.05 (m, 2H, Ar—H), 8.58 (s, 1H, Ar—H).
ESI-MS: 586 [M+H+]

EXAMPLE 39

Preparation of trans-N-(4-(2-(4-(benzo[d]isothiazol-3-yl)piperazin-1-yl)ethyl)cyclohexyl)-5-methoxyl-benzofuryl-2-sulfamide (□-15)

With intermediate 5 (1.0 mmol) and 5-methoxylbenzofuryl-2-sulfonyl chloride (1.2 mmol) as the starting materials, target compound □-15 (0.25 g, yield 44.1%) was obtained in accordance with the method for preparing compound I-1.
$^1$H NMR (DMSO-d$^6$, δ: ppm): 1.00-1.05 (m, 2H, A-H), 1.18-1.39 (m, 5H, A-H), 1.76-1.84 (m, 4H, A-H), 2.37 (t, 2H, J=7.8 Hz, N—CH$_2$), 2.90-2.93 (m, 1H, A-H), 3.10-3.13 (m, 4H, piperazine-CH$_2$), 3.40-3.43 (m, 4H, piperazine-CH$_2$), 3.76 (s, 3H, A-H), 7.20 (d, 1H, J=8.0 Hz, Ar—H), 7.32-7.34 (m, 3H, Ar—H), 7.51 (t, 1H, J=8.0 Hz, Ar—H), 7.54 (t, 1H, J=7.6 Hz, Ar—H), 7.84-7.87 (m, 2H, Ar—H).
ESI-MS: 571 [M+H+]

EXAMPLE 40

Preparation of cis-N-(4-(2-(4-(benzo[d]isothiazol-3-yl)piperazin-1-yl)ethyl)cyclohexyl)thienyl-2-sulfamide (□-16) and the salt thereof With intermediate 11 (1.0 mmol) and thienyl-2-sulfonyl chloride (1.2 mmol) as the starting materials, target compound □-16 (0.19 g, yield 38.7%) was obtained in accordance with the method for preparing compound I-1.
$^1$H NMR (DMSO-d$^6$, δ: ppm): 0.98-1.03 (m, 2H, A-H), 1.23-1.31 (m, 3H, A-H), 1.61-1.66 (m, 2H, A-H), 1.72-1.77 (m, 4H, A-H), 2.75 (t, 2H, J=7.8 Hz, N—CH$_2$), 3.00-3.04 (m, 1H, A-H), 3.17-3.20 (m, 4H, piperazine-CH$_2$), 3.47-3.50 (m, 4H, piperazine-CH$_2$), 7, 27 (t, 1H, J=4.0 Hz, Ar—H), 7.58 (t, 1H, J=8.0 Hz, Ar—H), 7.68-7.71 (m, 2H, Ar—H), 7.93 (d, 1H, J=4.0 Hz, Ar—H), 8.12-8.18 (m, 2H, Ar—H).
ESI-MS: 491 [M+H+]

Preparation of the Hydrobromide of Compound □-16

With compound □-16 (0.1 mmol) and 5% hydrobromic acid (0.1 mmol) as the starting materials, a white solid (0.05 g, yield 90.5%) was obtained in accordance with the method for preparing the hydrochloride of compound I-1.
Elemental analysis: C$_{23}$H$_{30}$N$_4$O$_2$S$_3$.HBr (theoretical value %: C, 48.33; H, 5.47; N, 9.80; experimental value %: C, 48.17; H, 5.65; N, 10.02).

EXAMPLE 41

Preparation of cis-N-(4-(2-(4-(benzo[d]isothiazol-3-yl)piperazin-1-yl)ethyl)cyclohexyl)-1H-pyrrolyl-3-sulfamide (□-17)

With intermediate 11 (1.0 mmol) and pyrrolyl-3-sulfonyl chloride (1.2 mmol) as the starting materials, target compound □-17 (0.28 g, yield 58.5%) was obtained in accordance with the method for preparing compound I-1.
$^1$H NMR (DMSO-d$^6$, δ: ppm): 1.04-1.19 (m, 2H, A-H), 1.31-1.38 (m, 3H, A-H), 1.66-1.71 (m, 2H, A-H), 1.78-1.83 (m, 4H, A-H), 2.78 (t, 2H, J=7.8 Hz, N—CH$_2$), 3.06-3.08 (m, 1H, A-H), 3.23-3.26 (m, 4H, piperazine-CH$_2$) 3.54-3.57 (m, 4H, piperazine-CH$_2$), 6.20-6.22 (d, 1H, J=0.4.0 Hz, Ar—H), 6.92-6.94 (m, 2H, Ar—H), 7.57 (t, 1H, J=0.0 Hz, Ar—H), 7.66 (t, 1H, J=8.0 Hz, Ar—H), 8.13-8.16 (m, 2H, Ar—H).
ESI-MS: 474 [M+H+]

EXAMPLE 42

Preparation of cis-N-(4-(2-(4-(benzo[d]isothiazol-3-yl)piperazin-1-yl)ethyl)cyclohexyl)furyl-2-sulfamide (□-18)

With intermediate 11 (1.0 mmol) and furyl-2-sulfonyl chloride (1.2 mmol) as the starting materials, target compound □-18 (0.31 g, yield 66.1%) was obtained in accordance with the method for preparing compound I-1.
$^1$H NMR (DMSO-d$^6$, δ: ppm): 0.96-1.01 (m, 2H, A-H), 1.20-1.28 (m, 3H, A-H), 1.58-1.63 (m, 2H, A-H), 1.68-1.73 (m, 4H, A-H), 2.71 (t, 2H, J=7.8 Hz, N—CH$_2$), 2.97-3.01 (m, 1H, A-H), 3.13-3.17 (m, 4H, piperazine-CH$_2$), 3.44-3.47 (m, 4H, piperazine-CH$_2$), 7.23 (t, 1H, J=4.0 Hz, Ar—H), 7.55 (t, 1H, J=8.0 Hz, Ar—H), 7.68-7.71 (m, 2H, Ar—H), 7.93 (d, 1H, J=4.0 Hz, Ar—H), 8.12-8.18 (m, 2H, Ar—H).
ESI-MS: 475 [M+H+]

EXAMPLE 43

Preparation of cis-N-(4-(2-(4-(benzo[d]isothiazol-3-yl)piperazin-1-yl)ethyl)cyclohexyl)benzo[b]thienyl-2-sulfamide (□-19)

With intermediate 11 (1.0 mmol) and benzo[b]thienyl-2-sulfonyl chloride (1.2 mmol) as the starting materials, target compound □-19 (0.42 g, yield 80.0%) was obtained in accordance with the method for preparing compound I-1.
$^1$H NMR (DMSO-d$^6$, δ: ppm): 1.05-1.09 (m, 2H, A-H), 1.22-1.40 (m, 4H, A-H), 1.79-1.86 (m, 5H, A-H), 2.41 (t, 2H, J=7.8 Hz, N—CH$_2$), 2.99-3.02 (m, 1H, A-H), 3.19-3.22 (m, 4H, piperazine-CH$_2$), 3.49-3.52 (m, 4H, piperazine-CH$_2$), 7.13 (d, 1H, J=8.0 Hz, Ar—H), 7.24 (m, 2H, Ar—H), 7.36-7.37 (m, 2H, Ar—H), 7.55-7.57 (m, 2H, Ar—H), 7.74 (s, 1H, Ar—H), 8.21-8.24 (m, 1H, Ar—H).
ESI-MS: 541 [M+H$^+$]

EXAMPLE 44

Preparation of cis-N-(4-(2-(4-(benzo[d]isothiazol-3-yl)piperazin-1-yl)ethyl)cyclohexyl)benzofuryl-2-sulfamide (□-20)

With intermediate 11 (1.0 mmol) and benzofuryl-2-sulfonyl chloride (1.2 mmol) as the starting materials, target compound □-20 (0.32 g, yield 60.5%) was obtained in accordance with the method for preparing compound I-1.

$^1$H NMR (DMSO-d$^6$, δ: ppm): 1.10-1.15 (m, 2H, A-H), 1.28-1.49 (m, 5H, A-H), 1.86-1.94 (m, 4H, A-H), 2.47 (t, 2H, J=7.8 Hz, N—CH$_2$), 2.99-3.02 (m, 1H, A-H), 3.20-3.23 (m, 4H, piperazine-CH$_2$), 3.50-3.53 (m, 4H, piperazine-CH$_2$) 7.21-7.23 (m, 3H, Ar—H), 7.30 (s, 1H, Ar—H), 7.41-7.43 (m, 2H, Ar—H), 7.61-7.63 (m, 1H, Ar—H), 7.8-7.90 (m, 1H, Ar—H), 8.32-8.33 (m, 1H, Ar—H).
ESI-MS: 525 [M+H$^+$]

EXAMPLE 45

Preparation of cis-N-(4-(2-(4-(benzo[d]isothiazol-3-yl)piperazin-1-yl)ethyl)cyclohexyl)-1H-indolyl-3-sulfamide (□-21)

With intermediate 11 (1.0 mmol) and indolyl-3-sulfonyl chloride (1.2 mmol) as the starting materials, target compound □-21 (0.26 g, yield 50.0%) was obtained in accordance with the method for preparing compound I-1.

$^1$H NMR (DMSO-d$^6$, δ: ppm): 0.99-1.04 (m, 2H, A-H), 1.23-1.31 (m, 3H, A-H), 1.61-1.66 (m, 2H, A-H), 1.72-1.77 (m, 4H, A-H), 2.75 (t, 2H, J=7.8 Hz, N—CH$_2$), 3.02-3.06 (m, 1H, A-H), 3.17-3.20 (m, 4H, piperazine-CH$_2$), 3.47-3.50 (m, 4H, piperazine-CH$_2$), 7.07-7.08 (m, 2H, Ar—H), 7.28 (t, 1H, J=8.0 Hz, Ar—H), 7.59 (t, 1H, J=8.0 Hz, Ar—H), 7.63 (d, 1H, J=4.0 Hz, Ar—H), 7.66 (m, 1H, Ar—H), 7.95 (d, 1H, J=4.0 Hz, Ar—H), 8.12-8.17 (m, 2H, Ar—H).
ESI-MS: 524 [M+H$^+$]

EXAMPLE 46

Preparation of cis-N-(4-(2-(4-(benzo[d]isothiazol-3-yl)piperazin-1-yl)ethyl)cyclohexyl)-5-methylfuryl-2-sulfamide (□-22)

With intermediate 11 (1.0 mmol) and 5-methylfuryl-2-sulfonyl chloride (1.2 mmol) as the starting materials, target compound □-22 (0.33 g, yield 67.8%) was obtained in accordance with the method for preparing compound I-1.

$^1$H NMR (DMSO-d$^6$, δ: ppm): 0.97-1.02 (m, 2H, A-H), 1.20-1.28 (m, 3H, A-H), 1.59-1.64 (m, 2H, A-H), 1.69-1.74 (m, 4H, A-H), 2.47 (s, 3H, A-H), 2.70 (t, 2H, J=7.8 Hz, N—CH$_2$), 2.97-3.01 (m, 1H, A-H), 3.13-3.18 (m, 4H, piperazine-CH$_2$), 3.44-3.48 (m, 4H, piperazine-CH$_2$), 7.14 (d, 1H, J=8.0 Hz, Ar—H), 7.46-7.47 (m, 2H, Ar—H), 7.55 (t, 1H, J=0.0 Hz, Ar—H), 8.22-8.24 (m, 2H, Ar—H).
ESI-MS: 489 [M+H$^+$]

EXAMPLE 47

Preparation of trans-(4-(2-(4-(benzo[d]isothiazol-3-yl)piperazin-1-yl)ethyl)cyclohexyl)methylcarbamate (□-1)

With intermediate 5 (1.0 mmol) and methyl chloroformate (1.1 mmol) as the starting materials, target compound □-1 (0.36 g, yield 88.7%) was obtained in accordance with the method for preparing compound I-1.

$^1$H NMR (DMSO-d$^6$, δ: ppm): 0.93-1.02 (m, 2H, A-H), 1.20-1.31 (m, 3H, A-H), 1.40-1.41 (m, 2H, A-H), 1.73-1.81 (m, 4H, A-H), 2.53 (t, 2H, J=7.8 Hz, N—CH$_2$), 2.62-2.65 (m, 4H, piperazine-CH$_2$), 3.17-3.22 (m, 1H, A-H), 3.4-3.49 (m, 4H, piperazine-CH$_2$), 3.77 (s, 3H, A-H), 7.46 (t, 1H, J=8.0 Hz, Ar—H), 7.59 (t, 1H, J=8.0 Hz, Ar—H), 8.09-8.11 (m, 2H, Ar—H).
ESI-MS: 403 [M+H$^+$]

EXAMPLE 48

Preparation of trans-(4-(2-(4-(benzo[d]isothiazol-3-yl)piperazin-1-yl)ethyl)cyclohexyl)ethylcarbamate (□-2)

With intermediate 5 (1.0 mmol) and ethyl chloroformate (1.1 mmol) as the starting materials, target compound □-2 (0.38 g, yield 91.0%) was obtained in accordance with the method for preparing compound I-1.

$^1$H NMR (DMSO-d$^6$, δ: ppm): 0.92-1.01 (m, 2H, A-H), 1.15 (t, 3H, J=8.0 Hz, A-H), 1.19-1.30 (m, 3H, A-H), 1.39-1.40 (m, 2H, A-H), 1.72-1.80 (m, 4H, A-H), 2.51 (t, 2H, J=7.8 Hz, N—CH$_2$), 2.60-2.63 (m, 4H, piperazine-CH$_2$), 3.16-3.21 (m, 1H, A-H), 3.44-3.47 (m, 4H, piperazine-CH$_2$), 3.96 (q, 2H, J=8.0 Hz, A-H), 7.44 (t, 1H, J=8.0 Hz, Ar—H), 7.57 (t, 1H, J=8.0 Hz, Ar—H), 8.06-8.08 (m, 2H, Ar—H).
ESI-MS: 417 [M+H$^+$]

EXAMPLE 49

Preparation of trans-N-(4-(2-(4-(benzo[d]isothiazol-3-yl)piperazin-1-yl)ethyl)cyclohexyl)isobutylcarbamate (□-3)

With intermediate 5 (1.0 mmol) and isobutyl chloroformate (1.2 mmol) as the starting materials, target compound □-3 (0.40 g, yield 90.7%) was obtained in accordance with the method for preparing compound I-1.

$^1$H NMR (DMSO-d$^6$, δ: ppm): 0.89 (d, 6H, J=8.0 Hz, A-H), 0.91-1.00 (m, 2H, A-H), 1.18-1.29 (m, 3H, A-H), 1.37-1.39 (m, 3H, A-H), 1.70-1.78 (m, 4H, A-H), 2.50 (t, 2H, J=7.8 Hz, N—CH$_2$), 2.58-2.61 (m, 4H, piperazine-CH$_2$), 3.14-3.19 (m, 1H, A-H), 3.42-3.45 (m, 4H, piperazine-CH$_2$), 3.92 (d, 2H, J=8.0 Hz, A-H), 7.41 (t, 1H, J=8.0 Hz, Ar—H), 7.54 (t, 1H, J=8.0 Hz, Ar—H), 8.03-8.05 (m, 2H, Ar—H).
ESI-MS: 445 [M+H$^+$]

EXAMPLE 50

Preparation of trans-(4-(2-(4-(benzo[d]isothiazol-3-yl)piperazin-1-yl)ethyl)cyclohexyl)cyclopropylcarbamate (□-4)

With intermediate 5 (1.0 mmol) and cyclopropyl chloroformate (1.2 mmol) as the starting materials, target compound □-4 (0.35 g, yield 81.4%) was obtained in accordance with the method for preparing compound I-1.

$^1$H NMR (DMSO-d$^6$, δ: ppm): 0.61-0.65 (m, 2H, A-H), 0.80-0.84 (m, 2H, A-H), 0.93-1.04 (m, 2H, A-H), 1.21-1.32 (m, 3H, A-H), 1.39-1.41 (m, 2H, A-H), 1.74-1.82 (m, 4H, A-H), 2.52 (t, 2H, J=7.8 Hz, N—CH$_2$), 2.62-2.65 (m, 4H, piperazine-CH$_2$), 2.75-2.77 (m, 1, A-H), 3.17-3.22 (m, 1H, A-H), 3.46-3, 49 (m, 4H, piperazine-CH$_2$), 7.45 (t, 1H, J=8.0 Hz, Ar—H), 7.58 (t, 1H, J=8.0 Hz, Ar—H), 8.07-8.10 (m, 2H, Ar—H).
ESI-MS: 429 [M+H$^+$]

EXAMPLE 51

Preparation of trans-(4-(2-(4-(benzo[d]isothiazol-3-yl)piperazin-1-yl)ethyl)cyclohexyl)cyclohexylcarbamate (□-5)

With intermediate 5 (1.0 mmol) and cyclohexyl chloroformate (1.2 mmol) as the starting materials, target compound □-5 (0.35 g, yield 73.6%) was obtained in accordance with the method for preparing compound I-1.
$^1$H NMR (DMSO-d$^6$, δ: ppm): 0.89-0.98 (m, 2H, A-H), 1.16-1.27 (m, 8, A-H), 1.36-1.37 (m, 5H, A-H), 1.69-1.77 (m, 7H, A-H), 2.48 (t, 2H, J=7.8 Hz, N—CH$_2$), 2.57-2.60 (m, 4H, piperazine-CH$_2$), 3.13-3.18 (m, 1H, A-H), 3.41-3.44 (m, 4H, piperazine-CH$_2$), 3.93 (m, 1H, A-H), 7.41 (t, 1H, J=8.0 Hz, Ar—H), 7.55 (t, 1H, J=0.0 Hz, Ar—H), 8.02-8.04 (m, 2H, Ar—H).
ESI-MS: 471 [M+H$^+$]

EXAMPLE 52

Preparation of trans-(4-(2-(4-(benzo[d]isothiazol-3-yl)piperazin-1-yl)ethyl) cyclohexyl)phenylcarbamate (□-6)

With intermediate 5 (1.0 mmol) and phenyl chloroformate (1.2 mmol) as the starting materials, target compound □-6 (0.37 g, yield 80.7%) was obtained in accordance with the method for preparing compound I-1.
$^1$H NMR (DMSO-d$^6$, δ: ppm): 0.93-1.01 (m, 2H, A-H), 1.14-1.23 (m, 3H, A-H), 1.30-1.32 (m, 2H, A-H), 1.72-1.81 (m, 4H, A-H), 2.40 (t, 2H, J=7.8 Hz, N—CH$_2$), 2.54-2.58 (m, 4H, piperazine-CH$_2$), 3.21-3.27 (m, 1H, A-H), 3.68-3.72 (m, 4H, piperazine-CH$_2$), 7.24-7.33 (m, 5H, Ar—H), 7.41 (t, 1H, J=8.0 Hz, Ar—H), 7.54 (t, 1H, J=8.0 Hz, Ar—H), 8.04-8.10 (m, 2H, Ar—H).
ESI-MS: 465 [M+H$^+$]

EXAMPLE 53

Preparation of trans-(4-(2-(4-(benzo[d]isothiazol-3-yl)piperazin-1-yl)ethyl)cyclohexyl)-3-methoxyphenylcarbamate (□-7)

With intermediate 5 (1.0 mmol) and 3-methoxyphenyl chloroformate (1.2 mmol) as the starting materials, target compound □-7 (0.31 g, yield 61.9%) was obtained in accordance with the method for preparing compound I-1.
$^1$H NMR (DMSO-d$^6$, δ: ppm): 0.92-1.00 (m, 2H, A-H), 1.13-1.22 (m, 3H, A-H), 1.29-1.31 (m, 2H, A-H), 1.71-1.80 (m, 4H, A-H), 2.39 (t, 2H, J=7.8 Hz, N—CH$_2$), 2.52-2.56 (m, 4H, piperazine-CH$_2$), 3.20-3.26 (m, 1H, A-H), 3.66-3.70 (m, 4H, piperazine-CH$_2$), 3.92 (s, 3H, A-H), 7.02-7.10 (m, 4H, Ar—H), 7.39 (t, 1H, J=8.0 Hz, Ar—H), 7.52 (t, 1H, J=8.0 Hz, Ar—H), 8.01-8.07 (m, 2H, Ar—H).
ESI-MS: 495 [M+H$^+$]

EXAMPLE 54

Preparation of trans-(4-(2-(4-(benzo[d]isothiazol-3-yl)piperazin-1-yl)ethyl)cyclohexyl)-2-methylphenyl-carbamate (□-8)

With intermediate 5 (1.0 mmol) and 2-methylphenyl chloroformate (1.2 mmol) as the starting materials, target compound □-8 (0.35 g, yield 73.1%) was obtained in accordance with the method for preparing compound I-1.
$^1$H NMR (DMSO-d$^6$, δ: ppm): 0.90-0.98 (m, 2H, A-H), 1.11-1.20 (m, 3H, A-H), 1.27-1.29 (m, 2H, A-H), 1.69-1.78 (m, 4H, A-H), 2.10 (s, 3H, A-H), 2.39 (t, 2H, J=7.8 Hz, N—CH$_2$), 2.51-2.55 (m, 4H, piperazine-CH$_2$), 3.18-3.24 (m, 1H, A-H), 3.65-3.69 (m, 4H, piperazine-CH$_2$), 7.22-7.30 (m, 4H, Ar—H), 7.40 (t, 1H, J=8.0 Hz, Ar—H), 7.53 (t, 1H, J=8.0 Hz, Ar—H), 8.03-8.09 (m, 2H, Ar—H).
ESI-MS: 479 [M+H$^+$]

EXAMPLE 55

Preparation of trans-(4-(2-(4-(benzo[d]isothiazol-3-yl)piperazin-1-yl)ethyl)cyclohexyl)-4-chlorophenyl-carbamate (□-9)

With intermediate 5 (1.0 mmol) and 4-chlorophenyl chloroformate (1.2 mmol) as the starting materials, target compound □-9 (0.38 g, yield 76.4%) was obtained in accordance with the method for preparing compound I-1.
$^1$H NMR (DMSO-d$^6$, δ: ppm): 0.98-1.06 (m, 2H, A-H), 1.19-1.28 (m, 3H, A-H), 1.35-1.37 (m, 2H, A-H), 1.77-1.86 (m, 4H, A-H), 2.45 (t, 2H, J=7.8 Hz, N—CH$_2$), 2.59-2.63 (m, 4H, piperazine-CH$_2$), 3.26-3.32 (m, 1H, A-H), 3.73-3.77 (m, 4H, piperazine-CH$_2$), 7.34-7.41 (m, 4H, Ar—H), 7.49 (t, 1H, J=8.0 Hz, Ar—H), 7.62 (t, 1H, J=8.0 Hz, Ar—H), 8.12-8.18 (m, 2H, Ar—H).
ESI-MS: 499 [M+H$^+$]

EXAMPLE 56

Preparation of trans-(4-(2-(4-(benzo[d]isothiazol-3-yl)piperazin-1-yl)ethyl)cyclohexyl)-4-nitrophenyl-carbamate (□-10)

With intermediate 5 (1.0 mmol) and 4-nitrophenyl chloroformate (1.2 mmol) as the starting materials, target compound i-10 (0.43 g, yield 85.1%) was obtained in accordance with the method for preparing compound I-1.
$^1$H NMR (DMSO-d$^6$, δ: ppm): 1.02-1.10 (m, 2H, A-H), 1.23-1.32 (m, 3H, A-H), 1.40-1.42 (m, 2H, A-H), 1.82-1.91 (m, 4H, A-H), 2.48 (t, 2H, J=7.8 Hz, N—CH$_2$), 2.64-2.68 (m, 4H, piperazine-CH$_2$), 3.31-3.37 (m, 1H, A-H), 3.78-3.82 (m, 4H, piperazine-CH$_2$), 7.44 (d, 2H, J=8.0 Hz, Ar—H), 7.57 (t, 1H, J=8.0 Hz, Ar—H), 7.69 (t, 1H, J=8.0 Hz, Ar—H), 8.19 (d, 2H, J=8.0 Hz, Ar—H), 8.23-8.28 (m, 2H, Ar—H).
ESI-MS: 510 [M+H$^+$]

EXAMPLE 57

Preparation of trans-(4-(2-(4-(benzo[d]isothiazol-3-yl)piperazin-1-yl)ethyl)cyclohexyl)benzylcarbamate (□-1)

With intermediate 5 (1.0 mmol) and benzyl chloroformate (1.2 mmol) as the starting materials, target compound □-11 (0.39 g, yield 82.4%) was obtained in accordance with the method for preparing compound I-1.
$^1$H NMR (DMSO-d$^6$, δ: ppm): 0.94-1.02 (m, 2H, A-H), 1.15-1.24 (m, 3H, A-H), 1.31-1.33 (m, 2H, A-H), 1.73-1.82 (m, 4H, A-H), 2.41 (t, 2H, J=7.8 Hz, N—CH$_2$), 2.55-2.59 (m, 4H, piperazine-CH$_2$), 3.22-3.28 (m, 1H, A-H), 3.69-3.73 (m, 4H, piperazine-CH$_2$), 5.00 (s, 2H, A-H), 7.30-7.39 (m,

EXAMPLE 58

Preparation of trans-(4-(2-(4-(benzo[d]isothiazol-3-yl)piperazin-1-yl)ethyl)cyclohexyl)benzofuryl-2-methylcarbamate (□-12)

With intermediate 5 (1.0 mmol) and benzofuryl-2-methyl chloroformate (1.2 mmol) as the starting materials, target compound □-12 (0.25 g, yield 47.8%) was obtained in accordance with the method for preparing compound I-1.

$^1$H NMR (DMSO-d$^6$, δ: ppm): 1.05-1.13 (m, 2H, A-H), 1.26-1.35 (m, 3H, A-H), 1.42-1.44 (m, 2H, A-H), 1.83-1.92 (m, 4H, A-H), 2.51 (t, 2H, J=78 Hz, N—CH$_2$), 2.66-2.70 (m, 4H, piperazine-CH$_2$), 3.33-3.39 (m, 1H, A-H), 3.80-3.84 (m, 4H, piperazine-CH$_2$), 5.03 (s, 2H, A-H), 7.22-7.24 (m, 3H, Ar—H), 7.31 (s, 1H, Ar—H), 7.42-7.46 (m, 2H, Ar—H), 7.62-7.64 (m, 1H, Ar—H), 7.88-7.90 (m, 1H, Ar—H), 8.31-8.34 (m, 1H, Ar—H).

ESI-MS: 519 [M+H$^+$]

EXAMPLE 59

Preparation of trans-(4-(2-(4-(benzo[d]isothiazol-3-yl)piperazin-1-yl)ethyl)cyclohexyl)thienyl-2-methyl-carbamate (□-13)

With intermediate 5 (1.0 mmol) and thienyl-2-methyl chloroformate (1.2 mmol) as the starting materials, target compound □-13 (0.29 g, yield 59.3%) was obtained in accordance with the method for preparing compound I-1.

$^1$H NMR (DMSO-d$^6$, δ: ppm): 0.98-1.06 (m, 2H, A-H), 1.22-1.31 (m, 3H, A-H), 1.38-1.40 (m, 2H, A-H), 1.81-1.90 (m, 4H, A-H), 2.49 (t, 2H, J=7.8 Hz, N—CH$_2$), 2.63-2.67 (m, 4H, piperazine-CH$_2$), 3.30-3.36 (m, 1H, A-H), 3.77-3.81 (m, 4H, piperazine-CH$_2$), 5.13 (s, 2H, A-H), 7.45 (dxd, 1H, J=8.0 Hz, 4.0 Hz, Ar—H), 7.51 (t, 1H, J=7.6 Hz, Ar—H), 7.63 (t, 1H, J=7.6 Hz, Ar—H), 7.78 (d, 1H, J=4.0 Hz, Ar—H), 8.11-8.14 (m, 2H, Ar—H), 8.29 (d, 1H, J=8.0 Hz, Ar—H).

ESI-MS: 485 [M+H$^+$]

EXAMPLE 60

Preparation of cis-(4-(2-(4-(benzo[d]isothiazol-3-yl)piperazin-1-yl)ethyl)cyclohexyl)methylcarbamate (□-14)

With intermediate 11 (1.0 mmol) and methyl chloroformate (1.2 mmol) as the starting materials, target compound □-14 (0.33 g, yield 81.3%) was obtained in accordance with the method for preparing compound I-1.

$^1$H NMR (DMSO-d$^6$, δ: ppm): 0.97-1.06 (m, 2H, A-H), 1.24-1.35 (m, 3H, A-H), 1.44-1.45 (m, 2H, A-H), 1.77-1.85 (m, 4H, A-H), 2.57 (t, 2H, J=7.8 Hz, N—CH$_2$), 2.66-2.69 (m, 4H, piperazine-CH$_2$), 3.21-3.26 (m, 1H, A-H), 3.50-3.53 (m, 4H, piperazine-CH$_2$), 3.81 (s, 3H, A-H), 7.50 (t, 1H, J=8.0 Hz, Ar—H), 7.63 (t, 1H, J=8.0 Hz, Ar—H), 8.13-8.15 (m, 2H, Ar—H).

ESI-MS: 403 [M+H$^+$]

EXAMPLE 61

Preparation of cis-(4-(2-(4-(benzo[d]isothiazol-3-yl)piperazin-1-yl)ethyl)cyclohexyl)ethylcarbamate (□-15)

With intermediate 11 (1.0 mmol) and ethyl chloroformate (1.2 mmol) as the starting materials, target compound □-15 (0.36 g, yield 86.2%) was obtained in accordance with the method for preparing compound I-1.

$^1$H NMR (DMSO-d$^6$, δ: ppm): 0.95-1.04 (m, 2H, A-H), 1.18 (t, 3H, J=8.0 Hz, A-H), 1.22-1.33 (m, 3H, A-H), 1.42-1.43 (m, 2H, A-H), 1.75-1.83 (m, 4H, A-H), 2.54 (t, 2H, J=7.8 Hz, N—CH$_2$), 2.63-2.66 (m, 4H, piperazine-CH$_2$), 3.19-3.24 (m, 1H, A-H), 3.47-3.450 (m, 4H, piperazine-CH$_2$), 3.99 (q, 2H, J=8.0 Hz, A-H), 7.47 (t, 1H, J=8.0 Hz, Ar—H), 7.60 (t, 1H, J=8.0 Hz, Ar—H), 8.09-8.11 (m, 2H, Ar—H).

ESI-MS: 417 [M+H$^+$]

EXAMPLE 62

Preparation of cis-(4-(2-(4-(benzo[d]isothiazol-3-yl)piperazin-1-yl)ethyl)cyclohexyl)benzylcarbamate (□-16)

With intermediate 11 (1.0 mmol) and benzyl chloroformate (1.2 mmol) as the starting materials, target compound □-16 (0.32 g, yield 67.6%) was obtained in accordance with the method for preparing compound I-1.

$^1$H NMR (DMSO-d$^6$, δ: ppm): 0.97-1.05 (m, 2H, A-H), 1.18-1.27 (m, 3H, A-H), 1.34-1.36 (m, 2H, A-H), 1.76-1.85 (m, 4H, A-H), 2.44 (t, 2H, J=7.8 Hz, N—CH$_2$), 2.58-2.62 (m, 4H, piperazine-CH$_2$), 3.25-3.31 (m, 1H, A-H), 3.72-3.76 (m, 4H, piperazine-CH$_2$), 5.04 (s, 2H, A-H), 7.34-7.43 (m, 5H, Ar—H), 7.49 (t, 1H, J=8.0 Hz, Ar—H), 7.62 (t, 1H, J=8.0 Hz, Ar—H), 8.11-8.17 (m, 2H, Ar—H).

ESI-MS: 479 [M+H$^+$]

EXAMPLE 63

Preparation of trans-1-(4-(2-(4-(benzo[d]isothiazol-3-yl)piperazin-1-yl)ethyl)cyclohexyl)-3-phenylurea (□-1) and the salt thereof Triphosgene (0.48 mmol) and dichloromethane (10 mL) were added into a 3-neck flask (50 mL), and cooled under ice bath to −10° C.~−5° C. The solution of compound 5 (0.44 mmol) and triethylamine (1 mL) in dichloromethane (10 mL) was slowly added dropwise, and stirred for 2 h by maintaining the temperature between −10° C. and −5° C. Aniline (0.88 mmol) and isopropanol (5 mL) were added into a 3-neck flask (50 mL), and the reaction solution was cooled under ice bath to −10° C.~0° C. The above reaction solution was slowly added dropwise to the system, stirred for 2 h by maintaining the temperature was controlled between −10° C. and −5° C., and reacted at RM for 12 h. The system was washed sequentially with ammonium chloride aqueous solution (10 mL×2), water (10 mL×1), and saturated saline (10 mL×2), and evaporated to dryness, and the residue was recrystallized with 95% ethanol to give a white solid IV-1 (0.16 g, yield 80.4%).

¹H NMR (DMSO-d⁶, δ: ppm): 0.96-1.13 (m, 3H, A-H), 1.26-1.28 (m, 2H, A-H), 1.39-1.40 (m, 2H, A-H), 1.75-1.87 (m, 4H, A-H), 2.40 (t, 2H, J=7.8 Hz, N—CH₂), 2.61-2.64 (m, 4H, piperazine-CH₂), 3.34-3.36 (m, 1H, A-H), 3.46-3.49 (m, 4H, piperazine-CH₂), 7.23-7.25 (m, 1 t, Ar—H), 7.35 (d×d, 2H, J=8.4 Hz, J=8.0 Hz, Ar—H), 7.40 (d, 2H, J=8.0 Hz, Ar—H) 7.48 (t, 1H, J=8.0 Hz, Ar—H), 7.61 (t, 1H, J=8.0 Hz, Ar—H), 8.07-8.11 (m, 2H, Ar—H).

ESI-MS: 464 [M+H⁺]

Preparation of the hydro bromide of compound □-1

With compound □-1 (0.1 mmol) and 5% hydrobromic acid (0.1 mmol) as the starting materials, a white solid (0.04 g, yield 79.2%) was obtained in accordance with the method for preparing the hydrochloride of compound I-1.

Elemental analysis: C₂₆H₃₃N₅₀S.HBr (theoretical value %: C, 57.35; H, 6.29; N, 12.86; experimental value %: C, 57.21; H, 6.14; N, 12.98).

Preparation of the Mesylate of Compound □-1

With compound □-1 (0.1 mmol) and methanesulfonic acid (0.1 mmol) as the starting materials, a white solid (0.05 g, yield 81.8%) was obtained in accordance with the method for preparing the hydrochloride of compound I-1.

Elemental analysis: C₂₆H₃₃N₅₀S.H₄O₃S (theoretical value %: C, 57.35; H, 6.29; N, 12.86; experimental value %: C, 57.21; H, 6.14; N, 12.98).

Preparation of the p-Tosylate Trihydrate of Compound □-1

Compound □-1 (1.0 mmol), p-toluene sulfonic acid (1.0 mmol), water (2 mL) and methanol (20 mL) were added into a single neck flask (50 mL), and stirred at RM for 1.5 h to provide a clear reaction solution. The reaction solution was evaporated to dryness, to provide an oil. Isopropanol (10 mL) was added and stirred for 5 h. A white solid was precipitated and filtered, and the filter cake was baked to dryness, recrystallized with 95% ethanol to give the white solid (0.47 g, yield 68.1%).

Elemental analysis: C₂₆H₃₃N₅₀S.C₇H₈O₃S.3H₂O (theoretical value %: C, 57.45; H, 6.87; N, 10.15; experimental value %: C, 57.68; H, 6.61; N, 10.34).

EXAMPLE 64

Preparation of trans-1-(4-(2-(4-(benzo[d]isothiazol-3-yl)piperazin-1-yl)ethyl)cyclohexyl)-3-phenylethylurea (□-2)

With intermediate 5 (1.0 mmol) and phenylethylamine (2.0 mmol) as the starting materials, target compound □-2 (0.41 g, yield 83.8%) was obtained in accordance with the method for preparing compound □-1.

¹H NMR (DMSO-d⁶, δ: ppm): 0.92-1.09 (m, 3H, A-H), 1.22-1.24 (m, 2H, A-H), 1.36-1.37 (m, 2H, A-H), 1.71-1.84 (m, 4H, A-H), 2.37 (t, 2H, J=7.8 Hz, N—CH₂), 2.44 (t, 2H, J=8.0 Hz, A-H), 2.57-2.60 (m, 4H, piperazine-CH₂), 3.30-3.32 (m, 1H, A-H), 3.42-3.45 (m, 4H, piperazine-CH₂), 3.86 (t, 2H, J=8.0 Hz, A-H), 7.19-7.25 (m, 3H, Ar—H), 7.27-7.31 (m, 2H, Ar—H) 7.40 (t, 1H, J=8.0 Hz, Ar—H), 7.53 (t, 1H, J=0.0 Hz, Ar—H), 8.01-8.04 (m, 2H, Ar—H).

ESI-MS: 492 [M+H⁺]

EXAMPLE 65

Preparation of trans-1-(4-(2-(4-(benzo[d]isothiazol-3-yl)piperazin-1-yl)ethyl)cyclohexyl)-3-(pyridin-3-yl)urea (□-3)

With intermediate 5 (1.0 mmol) and 3-aminopyridine (2.0 mmol) as the starting materials, target compound □-3 (0.27 g, yield 58.1%) was obtained in accordance with the method for preparing compound □-1.

¹H NMR (DMSO-d⁶, δ: ppm): 0.98-1.15 (m, 3H, A-H), 1.29-1.31 (m, 2H, A-H), 1.42-1.43 (m, 2H, A-H), 1.78-1.90 (m, 4H, A-H), 2.42 (t, 2H, J=7.8 Hz, N—CH₂), 2.63-2.66 (m, 4H, piperazine-CH₂), 3.36-3.38 (m, 1H, A-H), 3.49-3.52 (m, 4H, piperazine-CH₂), 7.32 (d×d, 1H, J=0.4 Hz, J=8.0 Hz, Ar—H), 7.53 (t, 1H, J=8.0 Hz, Ar—H), 7.67 (t, 1H, J=0.0 Hz, Ar—H), 7.92-7.94 (m, 2H, Ar—H), 8.16-8.20 (m, 2H, Ar—H), 8.82 (s, 1H, Ar—H).

ESI-MS: 465 [M+H⁺]

EXAMPLE 66

Preparation of trans-1-(4-(2-(4-(benzo[d]isothiazol-3-yl)piperazin-1-yl)ethyl)cyclohexyl)-3-(furan-2-yl)urea (□-4) and the salt thereof With intermediate 5 (1.0 mmol) and 2-aminofuran (2.0 mmol) as the starting materials, target compound □-4 (0.39 g, yield 85.4%) was obtained in accordance with the method for preparing compound □-1.

¹H NMR (DMSO-d⁶, δ: ppm): 0.92-1.15 (m, 3H, A-H), 1.29-1.31 (m, 2H, A-H), 1.42-1.43 (m, 2H, A-H), 1.78-1.90 (m, 4H, A-H), 2.43 (t, 2H, J=7.8 Hz, N—CH₂), 2.64-2.67 (m, 4H, piperazine-CH₂), 3.37-3.39 (m, 1H, A-H), 3.49-3.52 (m, 4H, piperazine-CH₂), 6.62 (d×d, 1H, J=8.0 Hz, 4.0 Hz, Ar—H), 7.09 (d, 1H, J=41.0 Hz, Ar—H), 7.50 (t, 1H, J=8.0 Hz, Ar—H), 7.62 (t, 1H, J=8.0 Hz, Ar—H), 8.07-8.12 (m, 2H, Ar—H), 8.23 (d, 1H, J=0.0 Hz, Ar—H).

ESI-MS: 454 [M+H⁺]

Preparation of the Hydrobromide of Compound □-4

With compound □-4 (0.1 mmol) and 5% hydrobromic acid (0.1 mmol) as the starting materials, a white solid (0.03 g, yield 62.7%) was obtained in accordance with the method for preparing the hydrochloride of compound I-1.

Elemental analysis: C₂₄H₃₁N₅O₂S.HBr (theoretical value %: C, 53.93; H, 6.03; N, 13.10; experimental value %: C, 53.78; H, 6.26; N, 12.95).

EXAMPLE 67

Preparation of trans-1-(benzo[b]thien-2-yl)-3-(4-(2-(4-(benzo[d]isothiazol-3-yl)piperazin-1-yl)ethyl)cyclohexyl)urea (□-5)

With intermediate 5 (1.0 mmol) and 2-aminobenzo[b]thiophene (2.0 mmol) as the starting materials, target compound □-5 (0.26 g, yield 49.6%) was obtained in accordance with the method for preparing compound □-1.

¹H NMR (DMSO-d⁶, δ: ppm): 0.93-1.16 (m, 3H, A-H), 1.28-1.30 (m, 2H, A-H), 1.41-1.42 (m, 2H, A-H), 1.77-1.89

(m, 4H, A-H), 2.44 (t, 2H, J=7.8 Hz, N—CH$_2$), 2.63-2.66 (m, 4H, piperazine-CH$_2$), 3.36-3.38 (m, 1H, A-H), 3.48-3.51 (m, 4H, piperazine-CH$_2$), 6.67 (s, 1H, Ar—H), 7.13 (d, 1H, J=8.0 Hz, Ar—H), 7.25 (m, 2H, Ar—H), 7.36-7.37 (m, 2H, Ar—H), 7.56-7.58 (m, 2H, Ar—H), 8.20-8.23 (m, 1H, Ar—H).

ESI-MS: 520 [M+H$^+$]

EXAMPLE 68

Preparation of trans-3-(4-(2-(4-(benzo[d]isothiazol-3-yl)piperazin-1-yl)ethyl)cyclohexyl)-1-methyl-1-phenylurea (□-6)

With intermediate 5 (1.0 mmol) and N-methylaniline (2.0 mmol) as the starting materials, target compound □-6 (0.26 g, yield 49.6%) was obtained in accordance with the method for preparing compound □-1.

$^1$H NMR (DMSO-d$^6$, δ: ppm): 0.95-1.12 (m, 3H, A-H), 1.25-1.27 (m, 2H, A-H), 1.38-1.39 (m, 2H, A-H), 1.74-1.86 (m, 4H, A-H), 2.39 (t, 2H, J=7.8 Hz, N—CH$_2$), 2.60-2.63 (m, 4H, piperazine-CH$_2$), 3.33-3.35 (m, 1H, A-H), 3.98 (s, 3H, A-H), 3.44-3.47 (m, 4H, piperazine-CH$_2$), 7.21-7.23 (m, 1H, Ar—H), 7.32 (d×d, 2H, J=8.4 Hz, J=8.0 Hz, Ar—H), 7.38 (d, 2H, J=0.0 Hz, Ar—H) 7.47 (t, 1H, J=8.0 Hz, Ar—H), 7.60 (t, 1H, J=8.0 Hz, Ar—H), 8.06-8.10 (m, 2H, Ar—H).

ESI-MS: 478 [M+H$^+$]

EXAMPLE 69

Preparation of trans-3-(4-(2-(4-(benzo[d]isothiazol-3-yl)piperazin-1-yl)ethyl)cyclohexyl)-1-butyl-1-phenylurea (□-7)

With intermediate 5 (1.0 mmol) and N-butylaniline (2.0 mmol) as the starting materials, target compound □-7 (0.27 g, yield 52.4%) was obtained in accordance with the method for preparing compound □-1.

$^1$H NMR (DMSO-d$^6$, δ: ppm): 0.89 (t, 3H, J=8.0 Hz, A-H), 0.94-1.12 (m, 5H, A-H), 1.24-1.27 (m, 2H, A-H), 1.41-1.43 (m, 4H, A-H), 1.73-1.85 (m, 4H, A-H), 2.38 (t, 2H, J=7.8 Hz, N—CH$_2$), 2.59-2.61 (m, 4H, piperazine-CH$_2$), 3.32-3.34 (m, 1H, A-H), 3.44-3.46 (m, 4H, piperazine-CH$_2$), 4.01 (t, 2H, J=8.0 Hz, A-H), 7.18-7.20 (m, 1H, Ar—H), 7.30 (d×d, 2H, J=8.4 Hz, J=8.0 Hz, Ar—H), 7.36 (d, 2H, J=8.0 Hz, Ar—H) 7.44 (t, 1H, J=8.0 Hz, Ar—H), 7.57 (t, 1H, J=0.0 Hz, Ar—H), 8.03-8.7 (m, 2H, Ar—H).

ESI-MS: 520 [M+H$^+$]

EXAMPLE 70

Preparation of trans-3-(4-(2-(4-(benzo[d]isothiazol-3-yl)piperazin-1-yl)ethyl)cyclohexyl)-1-methyl-1-(thien-2-yl)urea (□-8)

With intermediate 5 (1.0 mmol) and N-methylthienyl-2-amine (2.0 mmol) as the starting materials, target compound □-8 (0.29 g, yield 60.7%) was obtained in accordance with the method for preparing compound □-1.

$^1$H NMR (DMSO-d$^6$, δ: ppm): 0.91-1.14 (m, 3H, A-H), 1.28-1.30 (m, 2H, A-H), 1.41-1.42 (m, 2H, A-H), 1.77-1.89 (m, 4H, A-H), 2.42 (t, 2H, J=7.8H, N—CH$_2$), 2.63-2.66 (m, 4H, piperazine-CH$_2$), 3.12 (s, 3H, A-H), 3.35-3.37 (m, 1H, A-H), 3.47-3.50 (m, 4H, piperazine-CH$_2$), 6.60 (d×d, 1H, J=8.0 Hz, 4.0 Hz, Ar—H), 7.07 (d, 1H, J=4.0 Hz, Ar—H), 7.48 (t, 1H, J=8.0 Hz, Ar—H), 7.61 (t, 1H, J=8.0 Hz, Ar—H), 8.05-8.10 (m, 2H, Ar—H), 8.23 (d, 1H, J=8.0 Hz, Ar—H).

ESI-MS: 484 [M+H$^+$]

EXAMPLE 71

Preparation of trans-1-(4-(2-(4-(benzo[d]isothiazol-3-yl)piperazin-1-yl)ethyl)cyclohexyl)-3-(3-methoxyphenyl)urea (□-9)

With intermediate 5 (1.0 mmol) and 3-methoxyaniline (2.0 mmol) as the starting materials, target compound □-9 (0.35 g, yield 71.8%) was obtained in accordance with the method for preparing compound □-1.

$^1$H NMR (DMSO-d$^6$, δ: ppm): 0.94-1.1 (m, 3H, A-H), 1.23-1.25 (m, 2H, A-H), 1.36-1.37 (m, 2H, A-H), 1.72-1.84 (m, 4H, A-H), 2.36 (t, 2H, J=7.8 Hz, N—CH$_2$), 2.59-2.62 (m, 4H, piperazine-CH$_2$), 3.32-3.34 (m, 1H, A-H), 3.44-3.47 (m, 4H, piperazine-CH$_2$), 3.76 (s, 3H, A-H), 6.98-7.07 (m, 4H, Ar—H), 7.35 (t, 1H, J=8.0 Hz, Ar—H), 7.48 (t, 1H, J=8.0 Hz, Ar—H), 8.03-8.09 (m, 2H, Ar—H).

ESI-MS: 494 [M+H$^+$]

EXAMPLE 72

Preparation of trans-1-(4-(2-(4-(benzo[d]isothiazol-3-yl)piperazin-1-yl)ethyl)cyclohexyl)-3-(3-nitrophenyl)urea (□-10) and the salt thereof With intermediate 5 (1.0 mmol) and 3-nitroaniline (2.0 mmol) as the starting materials, target compound □-10 (0.20 g, yield 39.6%) was obtained in accordance with the method for preparing compound □-1.

$^1$H NMR (DMSO-d$^6$, δ: ppm): 1.0-1.18 (m, 3H, A-H), 1.31-1.33 (m, 2H, A-H), 1.44-1.45 (m, 2H, A-H), 1.80-1.92 (m, 4H, A-H), 2.45 (t, 2H, J=7.8 Hz, N—CH$_2$), 2.66-2.69 (m, 4H, piperazine-CH$_2$), 3.40-3.42 (m, 1H, A-H), 3.51-3.54 (m, 4H, piperazine-CH$_2$), 7.41 (m, 2H, Ar—H), 7.48 (t, 1H, J=8.0 Hz, Ar—H), 7.68-7.70 (m, 2H, A-H), 8.14-8.20 (m, 2H, Ar—H), 8.42 (s, 1H, Ar—H).

ESI-MS: 509 [M+H$^+$]

Preparation of the Hydrobromide of Compound □-10

With compound □-410 (0.1 mmol) and 5% trifluoracetic acid (0.1 mmol) as the starting materials, a white solid (0.05 g, yield 79.2%) was obtained in accordance with the method for preparing the hydrochloride of compound I-1.

Elemental analysis: C$_{26}$H$_{32}$N$_6$O$_3$S.CF$_3$CO$_2$H (theoretical value %: C, 54.01; H, 5.34; N, 13.50; experimental value %: C, 54.27; H, 5.09; N, 13.36).

EXAMPLE 73

Preparation of trans-1-(4-(2-(4-(benzo[d]isothiazol-3-yl)piperazin-1-yl)ethyl)cyclohexyl)-3-benzoylurea (□-1)

With intermediate 5 (0.44 mmol) and benzylamine (0.88 mmol) as the starting materials, target compound □-11 (0.18 g, yield 87.0%) was obtained in accordance with the method for preparing compound □-1.

$^1$H NMR (DMSO-d$^6$, δ: ppm): 0.94-1.1 (m, 3H, A-H), 1.24-1.26 (m, 2H, A-H), 1.38-1.39 (m, 2H, A-H), 1.73-1.85 (m, 4H, A-H), 2.38 (t, 2H, J=7.8 Hz, N—CH$_2$), 2.59-2.62

(m, 4H, piperazine-CH$_2$), 3.32-3.34 (m, 1H, A-H), 3.44-3.47 (m, 4H, piperazine-CH$_2$), 4.20 (s, 2H, A-H), 7.21-7.27 (m, 3H, Ar—H), 7.30-7.34 (m, 2H, Ar—H) 7.44 (t, 1H, J=8.0 Hz, Ar—H), 7.57 (t, 1H, J=8.0 Hz, Ar—H), 8.04-8.07 (m, 2H, Ar—H).

ESI-MS: 478 [M+H$^+$]

EXAMPLE 74

Preparation of cis-1-(4-(2-(4-(benzo[d]isothiazol-3-yl)piperazin-1-yl)ethyl)cyclohexyl)-3-phenylurea (□-12)

With intermediate 11 (1.0 mmol) and aniline (2.0 mmol) as the starting materials, target compound □-12 (0.34 g, yield 82.6%) was obtained in accordance with the method for preparing compound □-1.

$^1$H NMR (DMSO-d$^6$, δ: ppm): 1.02-1.19 (m, 3H, A-H), 1.32-1.34 (m, 2H, A-H), 1.45-1.46 (m, 2H, A-H), 1.81-1.93 (m, 4H, A-H), 2.46 (t, 2H, J=7.8 Hz, N—CH$_2$), 2.67-2.70 (m, 4H, piperazine-CH$_2$), 3.40-3.42 (m, 1H, A-H), 3.52-3.55 (m, 4H, piperazine-CH$_2$), 7.29-7.31 (m, 1H, Ar—H), 7.41 (d×d, 2H, J=8.4 Hz, J=0.0 Hz, Ar—H), 7.46 (d, 2H, J=8.0 Hz, Ar—H) 7.55 (t, 1H, J=8.0 Hz, Ar—H), 7.67 (t, 1H, J=8.0 Hz, Ar—H), 8.14-8.18 (m, 2H, Ar—H).

ESI-MS: 464 [M+H$^+$]

EXAMPLE 75

Preparation of cis-1-(4-(2-(4-(benzo[d]isothiazol-3-yl)piperazin-1-yl)ethyl)cyclohexyl)-3-benzoylurea (□-13)

With intermediate 11 (1.0 mmol) and benzylamine (2.0 mmol) as the starting materials, target compound □-13 (0.38 g, yield 80.5%) was obtained in accordance with the method for preparing compound □-1.

$^1$H NMR (DMSO-d$^6$, δ: ppm): 0.99-1.16 (m, 3H, A-H), 1.29-1.31 (m, 2H, A-H), 1.43-1.44 (m, 2H, A-H), 1.78-1.90 (m, 4H, A-H), 2.43 (t, 2H, J=7.8 Hz, N—CH$_2$), 2.64-2.67 (m, 4H, piperazine-CH$_2$), 3.37-3.39 (m, 1H, A-H), 3.49-3.52 (m, 4H, piperazine-CH$_2$), 4.23 (s, 2H, A-H), 7.26-7.32 (m, 3H, Ar—H), 7.34-7.38 (m, 2H, Ar—H) 7.49 (t, 1H, J=8.0 Hz, Ar—H), 7.62 (t, 1H, J=8.0 Hz, Ar—H), 8.09-8.12 (m, 2H, Ar—H).

ESI-MS: 478 [M+H$^+$]

EXAMPLE 76

Preparation of cis-1-(4-(2-(4-(benzo[d]isothiazol-3-yl)piperazin-1-yl)ethyl)cyclohexyl)-3-(furan-2-yl) urea (□-14) and the salt thereof With intermediate 11 (1.0 mmol) and 2-aminofuran (2.0 mmol) as the starting materials, target compound □-14 (0.37 g, yield 81.3%) was obtained in accordance with the method for preparing compound □-1.

$^1$H NMR (DMSO-d$^6$, δ: ppm): 0.96-1.19 (m, 3H, A-H), 1.33-1.35 (m, 2H, A-H), 1.46-1.47 (m, 2H, A-H), 1.82-1.94 (m, 4H, A-H), 2.47 (t, 2H, J=7.8 Hz, N—CH$_2$), 2.68-2.71 (m, 4H, piperazine-CH$_2$), 3.41-3.43 (m, 1H, A-H), 3.53-3.56 (m, 4H, piperazine-CH$_2$), 6.65 (d×d, 1H, J=80 Hz, 4.0 Hz, Ar—H), 7.13 (d, 1H, J=4.0 Hz, Ar—H), 7.55 (t, 1H, J=8.0 Hz, Ar—H), 7.67 (t, 1H, J=8.0 Hz, Ar—H), 8.11-8.16 (m, 2H, Ar—H), 8.27 (d, 1H, J=8.0 Hz, Ar—H).

ESI-MS: 454 [M+H$^+$]

Preparation of the Sulfate of Compound □-4

With compound □-14 (0.5 mmol) and 5% sulfuric acid (0.25 mmol) as the starting materials, a white solid (0.15 g, yield 60.3%) was obtained in accordance with the method for preparing the hydrochloride of compound I-1.

Elemental analysis: C$_{24}$H$_{31}$N$_5$O$_2$S.½H$_2$SO$_4$ (theoretical value %: C, 57.35; H, 6.42; N, 13.93; experimental value %: C, 57.16; H, 0.58; N, 13.67).

Preparation of the Mesylate of Compound □-14

With compound □-14 (1.0 mmol) and methanesulfonic acid (1.0 mmol) as the starting materials, a white solid (0.43 g, yield 78.1%) was obtained in accordance with the method for preparing the hydrochloride of compound I-1.

Elemental analysis: C$_{24}$H$_{31}$N$_5$O$_2$S.CH$_4$O$_3$S (theoretical value %: C, 54.62; H, 6.42; N, 12.74; experimental value %: C, 54.8; H, 6.31; N, 12.93).

EXAMPLE 77

| 1. Tablet: the compound of the present invention | 10 mg |
|---|---|
| sucrose | 150 mg |
| corn starch | 37 mg |
| magnesium stearate | 3 mg |

Preparation method: the active ingredient, sucrose and corn starch are mixed, humidified with water, stirred uniformly, dried, crushed and sieved, added with magnesium stearate, mixed uniformly, and tableted. Each tablet weighs 200 mg, containing 10 mg active ingredient.

EXAMPLE 78

| 2. Injection: the compound of the present invention | 5 mg |
|---|---|
| water for injection | 95 mg |

Preparation method: the active ingredient is dissolved in water for injection, mixed uniformly, and filtered. The resulting solution is dispensed into ampoules under sterile condition at 10 mg/ampoule, and the content of active ingredients is 0.5 mg/ampoule.

EXAMPLE 79

Dopamine D$_2$ Receptor Binding Test

1. Experimental Materials:
(1) D$_2$ receptor Cell Transfection:

This experiment utilizes the plasmid vector containing the gene of D$_2$ receptor protein for transfecting HEK293 cells by calcium phosphate transfection method. By culturing the transfected cells in culture medium containing G418 and selecting cell clones followed by radioligand binding test, a stable cell strain capable of expressing the D$_2$ receptor protein stably is finally obtained.

(2) Materials for the Receptor Binding Test:

Isotopic ligand [$^3$H] Spiperone (113.0 Ci/mmol) purchased from Sigma Corporation; (+) spiperone purchased from RBI Corporation; GF/B glassfiber filter purchased from Whatman Corporation; imported and subpackaged Tris; PPO and POPOP purchased from Shanghai No. 1 Reagent Factory; and fat-soluble scintillation fluid. Beckman LS-6500 multifunction liquid scintillation counter.

2. Experimental Methods:

(1) Cells:

HEK-293 cells are infected with the recombinant viruses containing various genes. 48-72 h later, receptor proteins are massively expressed on the membrane. The cells are centrifuged at 1000 rpm for 5 min, then the culture supernatant is discarded and the cell pellets are collected, preserved in refrigerator at −20° C., and resuspended with Tris-HCl reaction buffer (pH=7.5) before use.

(2) Competitive Receptor Binding Test:

The compound to be tested, the radioligand (20 μL for each) and the receptor protein (160 μL) are added to a reaction tube, wherein the compound to be tested and the positive drug both have the final concentration of 10 μmol/L.

After being incubated in water bath at 30° C. for 50 min, the tube is immediately transferred to ice bath to stop the reaction. The mixture is subjected to rapid suction filtration through GF/C glassfiber filter on Millipore cell sample collector, washed with eluent (50 mM Tris-HCl, pH 7.5) (3 mL×3) and dried under microwave for 5-6 min. The filter is transferred to a centrifuge tube (0.5 mL), added with 500 μL fat-soluble scintillation fluid, left in the dark for over min, and counted to determine the radioactivity intensity. The percentage inhibition ratio for each compound to inhibit the isotopic ligand binding is calculated with the following equation:

inhibition ratio (I%)=(total binding tube CPM−compound CPM)/(total binding tube CPM−non-specific binding tube CPM)×100%

Each compound is tested in duplicate, and the tests are carried out independently twice.

Compounds with an inhibition ratio of over 95% are subjected to the receptor binding test at a series of concentrations so as to determine half maximal inhibitory concentration (IC$_{50}$, the concentration of the compound required for inhibiting 50% binding of [$^3$H]-Spiperone to D$_2$ receptor). Each concentration is tested in duplicate, and tests are carried out independently twice for each compound.

Ki=IC$_{50}$(1[L]/K$_D$ (Ki: the affinity of the drug to the receptor, L: the concentration of the radioligand, K$_D$: the value of the affinity of the radioligand to the receptor)

The results of the D$_2$ receptor binding test are shown in Table 1 below.

TABLE 1

Affinity of the compound to D$_2$ receptor (Ki: nmol)

| No. | Ki value |
|---|---|
| I-1 | 2.90 |
| I-2 | 0.19 |
| I-3 | 0.21 |
| I-4 | 0.43 |
| I-5 | 0.32 |
| I-6 | 1.81 |
| I-7 | 4.65 |
| I-8 | 18.71 |
| I-9 | 2.57 |
| I-10 | 5.04 |
| I-11 | 4.81 |
| I-12 | 3.15 |
| I-13 | 1.78 |
| I-14 | 9.43 |
| I-15 | 21.34 |
| I-16 | 1.05 |
| I-17 | 0.27 |
| I-18 | 0.23 |
| I-19 | 0.82 |
| I-20 | 1.20 |
| I-21 | 2.96 |
| I-22 | 1.90 |
| I-23 | 1.73 |
| I-24 | 10.75 |
| II-1 | 0.43 |
| II-2 | 3.07 |
| II-3 | 1.98 |
| II-4 | 1.69 |
| II-5 | 0.58 |
| II-6 | 3.62 |
| II-7 | 8.54 |
| II-8 | 10.75 |
| II-9 | 7.38 |
| II-10 | 17.12 |
| II-11 | 9.76 |
| II-12 | 8.82 |
| II-13 | 4.50 |
| II-14 | 6.49 |
| II-15 | 3.03 |
| II-16 | 1.75 |
| II-17 | 2.94 |
| II-18 | 1.22 |
| II-19 | 1.78 |
| II-20 | 6.40 |
| II-21 | 1.01 |
| II-22 | 2.09 |
| III-1 | 1.18 |
| III-2 | 0.71 |
| III-3 | 8.67 |
| III-4 | 3.26 |
| III-5 | 11.84 |
| III-6 | 3.19 |
| III-7 | 1.93 |
| III-8 | 2.07 |
| III-9 | 4.33 |
| III-10 | 12.41 |
| III-11 | 1.60 |
| III-12 | 5.73 |
| III-13 | 2.54 |
| III-14 | 2.26 |
| III-15 | 1.97 |
| III-16 | 0.98 |
| IV-1 | 1.06 |
| IV-2 | 9.15 |
| IV-3 | 0.88 |
| IV-4 | 0.80 |
| IV-5 | 6.77 |
| IV-6 | 1.45 |
| IV-7 | 14.82 |
| IV-8 | 0.92 |
| IV-9 | 3.01 |
| IV-10 | 3.64 |
| IV-11 | 1.40 |
| IV-12 | 1.86 |
| IV-13 | 1.02 |
| IV-14 | 2.07 |

The results show that compound I-1 etc. have strong or moderate affinity to dopamine D$_2$ receptor.

EXAMPLE 80

Dopamine $D_3$ Receptor Binding Test

The experiment is carried out by the method according to Journal of Pharmacology and Experimental Therapeutics 2010, 333(1): 328. With [$^3$H]methyl-spiperone (0.3 nM) as the ligand and (+)-butaclamol (10 LM) for determining non-specific binding, binding tests are carried out on human recombinant $D_3$ receptor (expressed in CHO cells).

The results of the $D_3$ receptor binding test are shown in Table 2.

TABLE 2

Affinity of the compound to $D_3$ receptor (Ki: nmol)

| No. | Ki value |
| --- | --- |
| I-1 | 0.13 |
| I-2 | 0.056 |
| I-3 | 0.31 |
| I-4 | 0.029 |
| I-5 | 0.078 |
| I-6 | 0.035 |
| I-7 | 3.21 |
| I-8 | 2.78 |
| I-9 | 1.43 |
| I-10 | 6.98 |
| I-11 | 0.37 |
| I-12 | 1.02 |
| I-13 | 1.42 |
| I-14 | 2.86 |
| I-15 | 4.03 |
| I-16 | 1.87 |
| I-17 | 0.10 |
| I-18 | 0.18 |
| I-19 | 0.25 |
| I-20 | 0.19 |
| I-21 | 0.84 |
| I-22 | 0.071 |
| I-23 | 1.04 |
| I-24 | 3.80 |
| □-1 | 0.043 |
| □-2 | 0.57 |
| □-3 | 0.062 |
| □-4 | 1.03 |
| □-5 | 0.085 |
| □-6 | 2.76 |
| □-7 | 8.19 |
| □-8 | 4.51 |
| □-9 | 1.73 |
| □-10 | 7.09 |
| □-11 | 3.60 |
| □-12 | 1.99 |
| □-13 | 0.85 |
| □-14 | 9.37 |
| □-15 | 2.18 |
| □-16 | 0.23 |
| □-17 | 0.093 |
| □-18 | 5.37 |
| □-19 | 1.70 |
| □-20 | 2.01 |
| □-21 | 0.92 |
| □-22 | 1.44 |
| □-1 | 0.10 |
| □-2 | 0.058 |
| □-3 | 0.093 |
| □-4 | 1.81 |
| □-5 | 4.30 |
| □-6 | 0.74 |
| □-7 | 1.05 |
| □-8 | 8.49 |
| □-9 | 11.58 |
| □-10 | 7.12 |
| □-11 | 0.061 |
| □-12 | 6.53 |
| □-13 | 0.95 |
| □-14 | 0.087 |
| □-15 | 0.46 |
| □-16 | 1.03 |
| □-1 | 1.42 |
| □-2 | 3.81 |
| □-3 | 0.068 |
| □-4 | 1.04 |
| □-5 | 10.02 |
| □-6 | 0.13 |
| □-7 | 8.22 |
| □-8 | 5.80 |
| □-9 | 2.71 |
| □-10 | 4.15 |
| □-11 | 0.18 |
| □-12 | 2.05 |
| □-13 | 0.67 |
| □-14 | 2.30 |

The results show that compound I-1 etc. have strong affinity to $D_3$ receptor, which is comparable to that of the positive drug RGH-18. It is shown in combination with the results of Example 79 that, the compounds of this class also possess good $D_3/D_2$ receptor selectivity.

EXAMPLE 81

5-$HT_{1A}$ Receptor Binding Test

1. Experimental Materials:

The isotopic ligand of 5-$H_{1A}$ receptor [$^3$H]0.8-OH-DPAT (purchased from PE Corporation), (+)5-hydroxytryptamine (purchased from Sigma Corporation), GF/B glassfiber filter (purchased from Whatman Corporation), fat-soluble scintillation fluid: PPO and POPOP (purchased from Shanghai No. 1 Reagent Factory), toluene (purchased from Sinopharm Chemical Reagent Co., Ltd), and Tris (imported and sub-packaged).

Cells: HEK-293 cells stably expressing 5-$HT_{1A}$ receptors as obtained by gene recombination are cultured for 3-5 days in cell culture medium DMEM supplemented with 10% serum. The cells are collected with PBS and centrifuged at −4° C. and 3000 rpm for 10 min, the supernatant is then discarded, and the cell pellets are collected, preserved in refrigerator at −80° C., and resuspended with $D_1$ Binding Buffer (pH 7.4) before use.

2. Experimental Methods:

Competitive inhibition ratio of each compound at the concentration of 10 μmol/L to inhibit the binding of [$^3$H]8-OH-DPAT to 5-$HT_{1A}$ receptor is determined for primary screening.

Compounds with an inhibition ratio of over 95% are subjected to the receptor binding test at a series of concentrations so as to determine half maximal inhibitory concentration ($IC_{50}$, the concentration of the compound required for inhibiting 50% binding of [$^3$H]8-OH-DPAT to 5-$HT_{1A}$ receptor). Each concentration is tested in duplicate, and tests are carried out independently twice for each compound.

| Total binding tube | [$^3$H].8-OH-DPAT | 20 μL |
| --- | --- | --- |
| | $D_1$ Binding Buffer | 20 μL |
| | Cells | 160 μL |
| Non-specific tube | [$^3$H].8-OH-DPAT | 20 μL |
| | 5-HT($10^{-4}$) | 20 μL |
| | Cells | 160 μL |

-continued

| | | |
|---|---|---|
| Tube with the compound to be tested | [³H].8-OH-DPAT | 20 μL |
| | The compound to be tested | 20 μL |
| | Cells | 160 μL |

The components are mixed to homogeneity, and then the above tubes are transferred to water bath at 30° C. (1 h), removed into ice bath immediately, and suction filtered on Harvest (with ice cold Tris eluate for 5 times). The filter membrane is dried over medium heat for 8 min, removed into a centrifuge tube (0.5 mL), added with scintillation fluid, and left standed for 30 min before measurement.

I%=(total binding CPM−the tested compound CPM)/(total binding CPM−non-specific CPM)× 100%

$K_i = IC_{50}/(1+[L]/K_D)$ ($K_i$: the affinity of the drug to the receptor, L: the concentration of the radioligand, $K_D$: the value of the affinity of the radioligand to the receptor)

The results of the 5-HT$_{1A}$ receptor binding test are shown in Table 3 below.

TABLE 3

Affinity of the compound to 5-HT$_{1A}$ receptor (Ki: nmol)

| No. | Ki value |
|---|---|
| I-1 | 1.30 |
| I-2 | 1.10 |
| I-3 | 0.52 |
| I-4 | 7.60 |
| I-5 | 8.96 |
| I-6 | 3.54 |
| I-7 | 4.01 |
| I-8 | 10.23 |
| I-9 | 1.78 |
| I-10 | 5.19 |
| I-11 | 2.84 |
| I-12 | 3.62 |
| I-13 | 4.07 |
| I-14 | 9.02 |
| I-15 | 8.45 |
| I-16 | 6.20 |
| I-17 | 0.98 |
| I-18 | 7.55 |
| I-19 | 1.37 |
| I-20 | 3.06 |
| I-21 | 3.78 |
| I-22 | 6.95 |
| I-23 | 5.48 |
| I-24 | 10.11 |
| □-1 | 3.30 |
| □-2 | 7.58 |
| □-3 | 2.87 |
| □-4 | 5.79 |
| □-5 | 10.64 |
| □-6 | 17.15 |
| □-7 | 6.08 |
| □-8 | 3.96 |
| □-9 | 2.10 |
| □-10 | 7.09 |
| □-11 | 18.37 |
| □-12 | 1.99 |
| □-13 | 8.66 |
| □-14 | 12.75 |
| □-15 | 7.19 |
| □-16 | 4.48 |
| □-17 | 6.71 |
| □-18 | 2.54 |
| □-19 | 7.03 |
| □-20 | 5.19 |
| □-21 | 8.50 |
| □-22 | 2.02 |

TABLE 3-continued

Affinity of the compound to 5-HT$_{1A}$ receptor (Ki: nmol)

| No. | Ki value |
|---|---|
| □-1 | 1.14 |
| □-2 | 0.20 |
| □-3 | 4.72 |
| □-4 | 3.95 |
| □-5 | 1.69 |
| □-6 | 0.58 |
| □-7 | 2.10 |
| □-8 | 3.93 |
| □-9 | 5.12 |
| □-10 | 9.30 |
| □-11 | 0.79 |
| □-12 | 2.63 |
| □-13 | 1.76 |
| □-14 | 2.55 |
| □-15 | 0.97 |
| □-16 | 2.14 |
| □-1 | 3.65 |
| □-2 | 8.03 |
| □-3 | 1.79 |
| □-4 | 2.64 |
| □-5 | 14.81 |
| □-6 | 4.60 |
| □-7 | 10.79 |
| □-8 | 3.92 |
| □-9 | 2.88 |
| □-10 | 9.07 |
| □-11 | 5.30 |
| □-12 | 5.14 |
| □-13 | 4.83 |
| □-14 | 6.09 |

The results show that compound I-1 etc. have strong affinity to 5-HT$_{1A}$ receptor, which is comparable to that of RGH-188.

EXAMPLE 82

5-HT$_{2A}$ Receptor Binding Test

1. Experimental Materials (1) 5-HT$_{2A}$ Cell Transfection:

This experiment utilizes the plasmid vector containing the gene of the 5-HT$_{2A}$ receptor protein for transfecting HEK293 cells by calcium phosphate transfection method. By culturing the transfected cells in culture medium containing G418 and selecting cell clones followed by radioligand binding test, a stable cell strain capable of expressing the 5-HT$_{2A}$ receptor protein stably is finally obtained.

(2) Materials for the Receptor Binding Test:

Isotopic ligand [³H]-Ketanserin (67.0 Ci/mmol) purchased from PerkinElmer Corporation; (+) spiperone purchased from RBI Corporation; GF/B glassfiber filter purchased from Whatman Corporation; imported and subpackaged Tris; PPO and POPOP purchased from Shanghai No. 1 Reagent Factory; and fat-soluble scintillation fluid. Beckman LS-6500 multifunction liquid scintillation counter.

2. Experimental Methods

HEK-293 cells are infected with the recombinant viruses containing various genes. 48-72 h later, receptor proteins are massively expressed on the membrane. The cells are centrifuged at 1000 rpm for 5 min, then the culture supernatant is discarded and the cell pellets are collected, preserved in refrigerator at −20° C., and resuspended with Tris-HCl reaction buffer (PH 7.7) before use.

Competitive receptor binding test: the compound to be tested, the radioligand (10 μl for each) and the receptor protein (80 μl) are added to a reaction tube, wherein the compound to be tested and the positive drug both have the final concentration of 10 μmol/L. After being incubated in water bath at 37° C. for 15 min, the tube is immediately transferred to ice bath to stop the reaction. The mixture is subjected to rapid suction filtration through GF/B glassfiber filter on Millipore cell sample collector, washed with eluent (50 mM Tris-HCl, PH 7.7) (3 ml×3) and dried in microwave oven for 8-9 min. The filter is transferred to a centrifuge tube (0.5 mL), added with 500 μL fat-soluble scintillation fluid, left in the dark for over 30 min, and counted to determine the radioactivity intensity. The percentage inhibition ratio for each compound to inhibit the isotopic ligand binding is calculated with the following equation:

inhibition ratio (1%)=(total binding tube CPM−compound CPM)/(total binding tube CPM−non-specific binding tube CPM)×100%

Each compound is tested in duplicate, and the tests are carried out independently twice.

Compounds with an inhibition ratio of over 95% are subjected to the receptor binding test at a series of concentrations so as to determine half maximal inhibitory concentration ($IC_{50}$, the concentration of the compound required for inhibiting 50% binding of [$^3$H]-Ketanserin to 5-$HT_{2A}$ receptor). Each concentration is tested in duplicate, and tests are carried out independently twice for each compound.

$Ki=IC_{50}/(1+[L]/K_D)$ (Ki: the affinity of the drug to the receptor, L: the concentration of the radioligand, $K_D$: the value of the affinity of the radioligand to the receptor)

The results of the 5-$HT_{2A}$ receptor binding test are shown in Table 4 below.

TABLE 4

Affinity of the compound to 5-$HT_{2A}$ receptor (Ki: nmol)

| No. | Ki value |
|---|---|
| I-1 | 0.23 |
| I-2 | 0.15 |
| I-3 | 0.29 |
| I-4 | 0.64 |
| I-5 | 0.86 |
| I-6 | 0.72 |
| I-7 | 1.03 |
| I-8 | 2.55 |
| I-9 | 1.28 |
| I-10 | 3.79 |
| I-11 | 2.01 |
| I-12 | 2.89 |
| I-13 | 4.90 |
| I-14 | 3.52 |
| I-15 | 2.65 |
| I-16 | 1.12 |
| I-17 | 1.02 |
| I-18 | 1.87 |
| I-19 | 0.98 |
| I-20 | 0.57 |
| I-21 | 0.81 |
| I-22 | 1.33 |
| I-23 | 1.78 |
| I-24 | 2.00 |
| □-1 | 0.30 |
| □-2 | 1.06 |
| □-3 | 0.44 |
| □-4 | 0.88 |
| □-5 | 0.69 |
| □-6 | 1.47 |
| □-7 | 2.10 |
| □-8 | 1.96 |
| □-9 | 2.01 |
| □-10 | 5.58 |
| □-11 | 3.39 |
| □-12 | 5.20 |
| □-13 | 0.93 |

TABLE 4-continued

Affinity of the compound to 5-$HT_{2A}$ receptor (Ki: nmol)

| No. | Ki value |
|---|---|
| □-14 | 4.62 |
| □-15 | 1.29 |
| □-16 | 0.50 |
| □-17 | 1.01 |
| □-18 | 0.74 |
| □-19 | 2.05 |
| □-20 | 1.83 |
| □-21 | 3.97 |
| □-22 | 1.65 |
| □-1 | 1.16 |
| □-2 | 0.53 |
| □-3 | 3.09 |
| □-4 | 2.28 |
| □-5 | 1.63 |
| □-6 | 0.66 |
| □-7 | 1.42 |
| □-8 | 4.96 |
| □-9 | 8.01 |
| □-10 | 12.50 |
| □-11 | 0.37 |
| □-12 | 2.58 |
| □-13 | 0.60 |
| □-14 | 1.23 |
| □-15 | 0.89 |
| □-16 | 0.76 |
| □-1 | 0.83 |
| □-2 | 4.21 |
| □-3 | 0.49 |
| □-4 | 1.04 |
| □-5 | 8.93 |
| □-6 | 2.36 |
| □-7 | 10.69 |
| □-8 | 1.07 |
| □-9 | 2.84 |
| □-10 | 5.01 |
| □-11 | 0.91 |
| □-12 | 2.40 |
| □-13 | 1.27 |
| □-14 | 1.82 |

The results show that compound I-1 etc. have strong affinity to 5-$HT_{2A}$ receptor.

Summary of the Results of the Above In Vitro Receptor Binding Tests:

Compound I-1 etc. have strong affinity to 5-$HT_{1A}$ and $D_3$ receptor (Ki<10 nmol), which is similar to that of RGH-188; and strong affinity to 5-$HT_{2A}$ receptor, which is obviously superior to that of RGH-188. Such compounds have strong or moderate affinity to $D_2$ receptor, and most of the compounds have a $D_3/D_2$ receptor selectivity of greater than 10:1, which is superior to that of RGH-188 (with a selectivity of less than 10:1), indicating that such compounds have the potential of improving cognitive impairment, while the side effect may be lower than that of RGH-188.

The results of the affinity of the preferred compounds to four receptors are shown in Table 5 below.

TABLE 5

Affinities of compound I-1 etc. and RGH-188 to $D_2$, $D_3$, 5-$HT_{1A}$, and 5-$HT_{2A}$ receptors (Ki: nmol)

| No. | $D_2$ | $D_3$ | 5-$HT_{1A}$ | 5-$HT_{2A}$ |
|---|---|---|---|---|
| I-1 | 2.90 | 0.13 | 1.30 | 0.23 |
| I-2 | 0.19 | 0.056 | 1.10 | 0.15 |
| I-3 | 0.21 | 0.31 | 0.52 | 0.29 |
| I-4 | 0.43 | 0.029 | 7.60 | 0.64 |
| I-5 | 0.32 | 0.078 | 8.96 | 0.86 |
| I-6 | 1.81 | 0.035 | 3.54 | 0.72 |

TABLE 5-continued

Affinities of compound I-1 etc. and RGH-188 to $D_2$, $D_3$, $5\text{-}HT_{1A}$, and $5\text{-}HT_{2A}$ receptors (Ki: nmol)

| No. | $D_2$ | $D_3$ | $5\text{-}HT_{1A}$ | $5\text{-}HT_{2A}$ |
|---|---|---|---|---|
| I-7 | 4.65 | 3.21 | 4.01 | 1.03 |
| I-8 | 18.71 | 2.78 | 10.23 | 2.55 |
| I-9 | 2.57 | 1.43 | 1.78 | 1.28 |
| I-10 | 5.04 | 6.98 | 5.19 | 3.79 |
| I-11 | 4.81 | 0.37 | 2.84 | 2.01 |
| I-12 | 3.15 | 1.02 | 3.62 | 2.89 |
| I-13 | 1.78 | 1.42 | 4.07 | 4.90 |
| I-14 | 9.43 | 2.86 | 9.02 | 3.52 |
| I-15 | 21.34 | 4.03 | 8.45 | 2.65 |
| I-16 | 1.05 | 1.87 | 6.20 | 1.12 |
| I-17 | 0.27 | 0.10 | 0.98 | 1.02 |
| I-18 | 0.23 | 0.18 | 7.55 | 1.87 |
| I-19 | 0.82 | 0.25 | 1.37 | 0.98 |
| I-20 | 1.20 | 0.19 | 3.06 | 0.57 |
| I-21 | 2.96 | 0.84 | 3.78 | 0.81 |
| I-22 | 1.90 | 0.071 | 6.95 | 1.33 |
| I-23 | 1.73 | 1.04 | 5.48 | 1.78 |
| I-24 | 10.75 | 3.80 | 10.11 | 2.00 |
| □-1 | 0.43 | 0.043 | 3.30 | 0.30 |
| □-2 | 3.07 | 0.57 | 7.58 | 1.06 |
| □-3 | 1.98 | 0.062 | 2.87 | 0.44 |
| □-4 | 1.69 | 1.03 | 5.79 | 0.88 |
| □-5 | 0.58 | 0.085 | 10.64 | 0.69 |
| □-6 | 3.62 | 2.76 | 17.15 | 1.47 |
| □-7 | 8.54 | 8.19 | 6.08 | 2.10 |
| □-8 | 10.75 | 4.51 | 3.96 | 1.96 |
| □-9 | 7.38 | 1.73 | 2.10 | 2.01 |
| □-10 | 17.12 | 7.09 | 7.09 | 5.58 |
| □-11 | 9.76 | 3.60 | 18.37 | 3.39 |
| □-12 | 8.82 | 1.99 | 1.99 | 5.20 |
| □-13 | 4.50 | 0.85 | 8.66 | 0.93 |
| □-14 | 6.49 | 9.37 | 12.75 | 4.62 |
| □-15 | 3.03 | 2.18 | 7.19 | 1.29 |
| □-16 | 1.75 | 0.23 | 4.48 | 0.50 |
| □-17 | 2.94 | 0.093 | 6.71 | 1.01 |
| □-18 | 1.22 | 5.37 | 2.54 | 0.74 |
| □-19 | 1.78 | 1.70 | 7.03 | 2.05 |
| □-20 | 6.40 | 2.01 | 5.19 | 1.83 |
| □-21 | 1.01 | 0.92 | 8.50 | 3.97 |
| □-22 | 2.09 | 1.44 | 2.02 | 1.65 |
| □-1 | 1.18 | 0.10 | 1.14 | 1.16 |
| □-2 | 0.71 | 0.058 | 0.20 | 0.53 |
| □-3 | 8.67 | 0.093 | 4.72 | 3.09 |
| □-4 | 3.26 | 1.81 | 3.95 | 2.28 |
| □-5 | 11.84 | 4.30 | 1.69 | 1.63 |
| □-6 | 3.19 | 0.74 | 0.58 | 0.66 |
| □-7 | 1.93 | 1.05 | 2.10 | 1.42 |
| □-8 | 2.07 | 8.49 | 3.93 | 4.96 |
| □-9 | 4.33 | 11.58 | 5.12 | 8.01 |
| □-10 | 12.41 | 7.12 | 9.30 | 12.50 |
| □-11 | 1.60 | 0.061 | 0.79 | 0.37 |
| □-12 | 5.73 | 6.53 | 2.63 | 2.58 |
| □-13 | 2.54 | 0.95 | 1.76 | 0.60 |
| □-14 | 2.26 | 0.087 | 2.55 | 1.23 |
| □-15 | 1.97 | 0.46 | 0.97 | 0.89 |
| □-16 | 0.98 | 1.03 | 2.14 | 0.76 |
| □-1 | 1.06 | 1.42 | 3.65 | 0.83 |
| □-2 | 9.15 | 3.81 | 8.03 | 4.21 |
| □-3 | 0.88 | 0.068 | 1.79 | 0.49 |
| □-4 | 0.80 | 1.04 | 2.64 | 1.04 |
| □-5 | 6.77 | 10.02 | 14.81 | 8.93 |
| □-6 | 1.45 | 0.13 | 4.60 | 2.36 |
| □-7 | 14.82 | 8.22 | 10.79 | 10.69 |
| □-8 | 0.92 | 5.80 | 3.92 | 1.07 |
| □-9 | 3.01 | 2.71 | 2.88 | 2.84 |
| □-10 | 3.64 | 4.15 | 9.07 | 5.01 |
| □-11 | 1.40 | 0.18 | 5.30 | 0.91 |
| □-12 | 1.86 | 2.05 | 5.14 | 2.40 |
| □-13 | 1.02 | 0.67 | 4.83 | 1.27 |
| □-14 | 2.07 | 2.30 | 6.09 | 1.82 |
| RGH-188 | 0.78 | 0.09 | 2.16 | 20.50 |

EXAMPLE 83

In Vivo Anti-Schizophrenia Activity Tests for the Compounds

1. Apomorphine Model:

(1) Establishment of Apomorphine-Induced Schizophrenic Mouse Model 96 inbred C57BL/6 mice, half male and half female, are randomly divided into 8 groups for weight balance: a blank control group, a model control group, groups of the compounds as recited in the claims in gradient dosages (0.12, 0.22, 0.35, 0.40, and 0.90 mg·kg$^{-1}$) and RGH-188 group (0.40 mg·kg$^{-1}$). The drugs are administered by gastric gavage. The model control group is given the same volume of solvent by gastric gavage. 30 min after the administration of the compound to be tested, apomorphine solution (dissolved in 0.1% ascorbic acid) is intraperitoneally injected at 10.0 mL·kg$^{-1}$ body weight of mice to induce the establishment of the schizophrenic mouse model.

(2) Observation of Stereotyped Behaviors

After apomorphine is administered to the mice, the mice are observed as to whether stereotyped behaviors such as tail erection and wall-climbing etc. appear during the first 30 seconds of the periods of 6-10, 11-15, 16-20, 21-25, 26-30, 31-35, 36-40, 41-45, 46-50, 51-55, and 56-60 min, and are scored according to the following standards: 0, indicating no behaviors as stated above are observed in the 30 seconds (t<1 sec); 1, indicating discontinuous and moderate behaviors as stated above are observed in the 30 seconds (1 sec<t<3 sec); and 2, indicating continuous and intense behaviors as stated above are observed in the 30 seconds (t>3 sec). Total score of the stereotyped behaviors of the mice such as tail erection and wall-climbing in the 60 minutes is calculated. Calculation of $ED_{50}$: improvement ratio=(score of the stereotyped behaviors in the model control group−score of the stereotyped behaviors in the administration group)/score of the stereotyped behaviors in the model control group×100%, which is fitted into a regression equation for calculating $ED_{50}$.

(3) Administration and Post-Administration Observation

Mice are weighed on the day of administration, and the dosage is determined according to the body weight. The clinical response symptoms of the animals shall be recorded during the administration and test procedures.

(4) Statistical Method

All the data are presented in x̄±SD and processed with SPSS 17.0 software. The means of two samples are compared with t test and one-way ANOVA. p<0.05 indicates significant difference.

(5) Experimental Results

Detailed results are shown in Table 6~Table 8.

TABLE 6

Effects of the single oral administration of compound I-6 on the total stereotyped behaviors in the Apo.-induced schizophrenic mouse model

| Group | n | Dosages (mg · kg$^{-1}$) | Score of stereotyped behaviors | Improvement ratio (%) |
|---|---|---|---|---|
| Blank control group | 12 | — | 0.17 ± 0.39 | |
| Model control group | 12 | — | 26.33 ± 5.26** | |
| RGH-188 group | 12 | 0.40 | 6.41 ± 3.16 | 75.64 |
| I-6 group | 12 | 0.12 | 23.02 ± 8.32 | 12.59 |

TABLE 6-continued

Effects of the single oral administration of compound I-6 on the total stereotyped behaviors in the Apo.-induced schizophrenic mouse model

| Group | n | Dosages (mg · kg$^{-1}$) | Score of stereotyped behaviors | Improvement ratio (%) |
|---|---|---|---|---|
| I-6 group | 12 | 0.22 | 15.52 ± 6.25# | 41.07 |
| I-6 group | 12 | 0.35 | 5.48 ± 4.61## | 79.48 |
| I-6 group | 12 | 0.40 | 4.01 ± 3.65## | 84.80 |
| I-6 group | 12 | 0.90 | 0.71 ± 0.94## | 97.29 |

*P < 0.05, **P < 0.01, compared with the blank control group;
P < 0.05, ##P < 0.01, compared with the model control group The inhibition of the stereotyped behaviors of the mice caused by compounds I-1, I-4, and I-22 in this model is determined by the same method at reasonably designed administration dosages. Detailed results can be found in

TABLE 7

Inhibition of the total stereotyped behaviors in Apo.-induced schizophrenic mouse model by the single oral administration of compounds I-1, I-4, I-6 and I-22

| Compound | ED$_{50}$ (mg/Kg) |
|---|---|
| I-1 | 0.28 |
| I-4 | 0.37 |
| I-6 | 0.23 |
| I-22 | 0.59 |

The inhibition of the stereotyped behaviors of the mice caused by the compounds of □, □, and □ class in this model is determined by the same method at reasonably designed administration dosages. Detailed results can be found in Table 8.

TABLE 8

ED$_{50}$ values of the representative compounds of other classes in this model

| Compound | ED$_{50}$ (mg/Kg) | Compound | ED$_{50}$ (mg/Kg) |
|---|---|---|---|
| □-1 | 0.20 | □-11 | 0.10 |
| □-3 | 0.30 | □-14 | 0.45 |
| □-5 | 0.64 | □-3 | 0.12 |
| □-17 | 0.38 | □-6 | 0.48 |
| □-3 | 0.76 | □-11 | 0.53 |

The results of this test show that:

As compared with the blank control group, the model control group shows significantly increased total stereotyped behaviors (P<0.01), indicating that apomorphine induces the development of schizophrenic symptoms in mice.

As compared with the model control group, the positive drug RGH-188 and the compounds as recited in the claims all can significantly reduce the stereotyped behaviors in mice, and thus the compounds of the present invention have great effect of treating schizophrenic positive symptoms, given that the apomorphine-induced schizophrenia mnodel is a classical model for the positive symptoms of schizophrenia.

At the same dosage (0.40 mg/Kg), compound I-6 has a greater improvement ratio than RGH-188 for the stereotyped behaviors in mice, indicating a better in vivo activity of compound I-6 than that of RGH-188.

2. MK-801 Model:

(1) Establishment of MK-801-Induced Schizophrenic Mouse Model 80 inbred C57BL/6 mice, half male and half female, are randomly divided into 8 groups for gender and weight balance: a blank control group, a model control group, RGH-188 (0.05 mg/Kg) control group, and groups of the compounds as recited in the claims in gradient dosages (0.02, 0.03, 0.05, 0.09, and 0.15 mg/kg). Each animal is conditioned in a soundproof box for 30 min on the day before the experiment. On the next day, 30 min after the administration of the compound to be tested, 0.025 mg/mL MK-801 solution is intraperitoneally injected at 10.0 mL/kg body weight of mice to induce the establishment of the schizophrenic mouse model. The blank control group is intraperitoneally injected with the same volume of normal saline.

(2) Observation of Open-Field Movement

After MK-801 is administered, the mouse is placed into the soundproof box immediately, and the total distance of spontaneous movement of the mouse in 60 min is observed and recorded.

Improvement ratio=(the total distance of movement in the model control group−the total distance of movement in the administration group)/(the total distance of movement in the model control group)*100%

A regression equation is obtained according to the above equation, and ED$_{50}$ is obtained by calculation.

(3) Experiment Observation

Mice are weighed on the day of administration, and the dosage is determined according to the body weight. The clinical response symptoms of the animals are recorded during the test procedure.

(4) Statistical Method

All the data are presented in $\bar{x}$±SD and processed with SPSS 17.0 software. The means of two samples are compared with t test and one-way ANOVA. p<0.05 indicates significant difference.

(5) Experimental Results

Detailed results are shown in Table 9~Table 1.

TABLE 9

Effects of the single oral administration of compound I-6 on the total distance of the open-field movement in the MK-801-induced schizophrenic mouse model ($\bar{x}$ ± SD)

| Group | Animal number | Dosages (mg/kg) | Total distance of the spontaneous movement (cm) | Improvement ratio (%) |
|---|---|---|---|---|
| Normal control group | 10 | — | 10112.28 ± 3186.36 | |
| Model control group | 10 | — | 28896.87 ± 6547.22** | |
| RGH-188 group | 10 | 0.05 | 15847.04 ± 7432.19 | 45.16 |
| I-6 group | 10 | 0.02 | 19482.27 ± 11047.75 | 32.58 |
| I-6 group | 10 | 0.03 | 17280.33 ± 9364.31 | 40.20 |
| I-6 group | 10 | 0.05 | 11145.52 ± 6988.56# | 61.43 |
| I-6 group | 10 | 0.09 | 7796.38 ± 4382.94## | 73.02 |
| I-6 group | 10 | 0.15 | 3360.71 ± 734.45## | 88.37 |

*P < 0.05, **P < 0.01, compared with the normal control group;
P < 0.05, ##P < 0.01, compared with the model control group

TABLE 10

Effects of the single oral administration of compounds I-1, I-4, I-6, and I-22 on the total distance of the open-field movement in the MK-801-induced schizophrenic mouse model ($ED_{50}$)

| Compound | $ED_{50}$ (mg/Kg) |
| --- | --- |
| I-1 | 0.052 |
| I-4 | 0.073 |
| I-6 | 0.038 |
| I-22 | 0.062 |

The effects of the representative compounds of □, □, and □ classes on the open-field movement in mice are determined in this model by the same method at reasonably designed administration dosages.

TABLE 11

$ED_{50}$ values of the representative compounds of other classes in this model

| Compound | $ED_{50}$ (mg/Kg) | Compound | $ED_{50}$ (mg/Kg) |
| --- | --- | --- | --- |
| □-1 | 0.074 | □-11 | 0.092 |
| □-3 | 0.047 | □-14 | 0.058 |
| □-5 | 0.088 | □-3 | 0.11 |
| □-17 | 0.053 | □-6 | 0.084 |
| □-3 | 0.061 | □-11 | 0.060 |

The results of the test show that:
As compared with the blank control group, MK-801 ip. can successfully induce significantly increased distance of the open-field movement in mice, indicating that MK-801 can induce the development of schizophrenic symptoms in mice.
As compared with model group, RGH-188 and the compounds as recited in the claims can significantly improve the total distance of the open-field movement in mice, and thus the compounds of the present invention have great effect of treating schizophrenic negative symptoms, given that the open-field movement model induced by MK-801 is a conventional model for the negative symptoms of schizophrenia.
At the same dosage (0.05 mg/Kg), compound I-6 has a greater improvement ratio than RGH-188 for the open-field movement in mice, indicating a better activity of compound I-6 than that of RGH-188 in this model.

EXAMPLE 84

Acute toxicity tests for compounds I-1, I-4, I-6, and I-22
(1) Experimental Scheme
Toxicity symptoms and death in the ICR mice after the oral administration of RGH-188, compound I-1 etc. are observed for comparing the acute toxicity.
Vehicle preparation: an appropriate amount of tween-80 is weighed and diluted with deionized water to a concentration of 5% (g/v) tween-80.
Administration preparation: the compounds to be tested are weighed, respectively, and formulated into suspensions at concentrations of 6.25, 12.50, 25.00, 50.00 and 100.00 mg/mL (corresponding to 125, 250, 500, 1000, 2000 mg/kg, respectively) with 5% tween-80 solution.
Administration route: the administration routes for the compounds to be tested and the vehicle control group (0.5% tween-8) are both through oral administration.
Administration frequency: single administration, fasted overnight before administration.
Administration capacity: 20 mL/Kg.

Observation of general symptoms: the animals are observed at about 0.5, 1, 2, 4, and 6 hours respectively, after the first administration on the first day, and observed twice a day, one in the morning and one in the afternoon, on the second to the sixth day. Observed objects include but are not limited to general condition, behavior activity, gait and posture, eye, mouth, nose, gastrointestinal tract, skin and hair, and genitourinary tract.
(2) Statistical Analysis
Body weight is expressed in mean±SD. Comparison among groups is carried out with Levene's test and one-way ANOVA, followed by Dunnet t test if there exists a difference.
(3) Experimental Results are Shown in Table 12

TABLE 12

Results of the aute toxicity tests for single oral administration of compounds I-1, I-4, I-6, I-22 and RGH-188

| Tested compound | $LD_{50}$ (mg/Kg) |
| --- | --- |
| I-1 | 1670 mg/Kg |
| I-4 | >2000 mg/Kg |
| I-6 | >2000 mg/Kg |
| I-22 | 1530 mg/Kg |
| RGH-188 | 760 mg/Kg |

The results show that among the above tested compounds, compounds I-4 and I-6 both have the $LD_{50}$ of greater than 2000 mg/kg, indicating their acute toxicity is far below that of RGH-188 (760 mg/kg), and compounds I-1 and I-22 have the $LD_{50}$ values of 1670 mg/Kg and 1530 mg/Kg, respectively, indicating a better safety than that of RGH-188.

EXAMPLE 85

Acute toxicity tests for the representative compounds of II, III, and IV classes
(1) The acute toxicity of the representative compounds of □, □, □ classes is investigated with the method of Example 81.
(2) Experimental results are shown in Table 13

TABLE 13

Results of the acute toxicity tests for single oral administration of the representative compounds of □, □, □ classes and RGH-188

| Tested compound | $LD_{50}$ (mg/Kg) | Tested compound | $LD_{50}$ (mg/Kg) |
| --- | --- | --- | --- |
| □-1 | >2000 mg/Kg | □-14 | 1080 mg/Kg |
| □-3 | >2000 mg/Kg | □-3 | >2000 mg/Kg |
| □-5 | 1105 mg/Kg | □-6 | 1390 mg/Kg |
| □-17 | 1860 mg/Kg | □-11 | >2000 mg/Kg |
| □-3 | >2000 mg/Kg | RGH-188 | 760 mg/Kg |
| □-11 | 1240 mg/Kg | | |

The results show that among the above tested compounds, compounds □-1, □-3, □-3, □-3, and □-11 all have the $LD_{50}$ of greater than 2000 mg/Kg, indicating their acute toxicity is far below that of RGH-188 (760 mg/Kg), and compounds □-5, □-17, □-11, □-14, □-6 have the $LD_{50}$ values of 1105 mg/Kg, 1860 mg/Kg, 1240 mg/Kg, 1080 mg/Kg and 1390 mg/Kg, respectively, indicating a better safety than that of RGH-188.

EXAMPLE 86

Bacterial Reverse Mutation Tests for Compounds I-1, I-4, I-6, and I-22

Compounds I-1, RGH-188 etc. are investigated by the reverse mutation test with histidine-auxotrophic strains of *salmonella typhimurium* as to whether they lead to a gene mutation, so as to evaluate their potential mutagenicity.

(1) Formulation Method 0.0303 g compound to be tested is accurately weighed before use, and completely dissolved in a certain amount of the solvent DMSO under a sterile and ultrasonic condition to formulate a solution with the highest concentration of 100000.0 μg/mL, which is then serially diluted at a 1:2 (v/v) ratio to obtain solutions of 9 different concentrations, i.e. 33333.0, 11111.0, 3704.0, 1235.0, 412.0, 137.0, 46.0 and 15.0 μg/mL.

(2) Negative Control DMSO
(3) Positive Control

| Strain | Name | Without metabolic activation system (−S9) | | | With metabolic activation system (+S9) | | | |
|---|---|---|---|---|---|---|---|---|
| | | Company | Batch number | Final concentration | Name | Company | Batch number | Final concentration |
| TA98 | 2-nitrofluorene | Aldrich | 09213BA | 4 μg/well | 2-aminoanthracene | Aldrich | 15216JA | 0.6 μg/well |
| TA100 | sodium azide | Sigma | 043K0056 | 0.4 μg/well | 2-aminoanthracene | Aldrich | 15216JA | 0.6 μg/well |

(4) Strains

Histidine-auxotrophic mutant strains TA98 and TA100 of *Salmonella typhimurium* are purchased from MolTox Corporation, under the batch numbers of 4367D and 4370D, respectively.

(5) Metabolic Activation System

The metabolic activation system (S9) is purchased from MolTox Corporation, with the specification of 2 mL/bottle, the batch number of 2548, and the protein content of 38.5 mg/mL. It is the liver homogenate of the SD male rate induced with 500 mg/kg polychlorobiphenyl (Aroclor 1254).

S9, coenzyme □, glucose-6-phosphate, etc. are mixed to form the hepatic microsomal enzyme system (S9 mixture) before use.

(6) Official Experiment

The official experiment consists of two parallel tests with or without the metabolic activation system. By a standard plate incorporation method, the melted top layer culture medium (500 μL) containing 0.6% agar, 0.5% NaCl, 0.5 mM biotin and 0.5 mM histidine is mixed with the following materials:
the solution of the compound to be tested (or negative/positive control) (20 μL)
overnight culture broth (25 μL)
S9 mixture solution or 0.2 M sodium phosphate buffer (pH=7.4) (100 L), The mixture is shaken to homogeneity, plated on a prefabricated V-B underlayer medium, coagulated at RM, and placed inversely and incubated in a 37° C. incubator for 72 h, and the results are observed. In the official experiment, negative and positive control groups are provided for each strain, and each group is tested in duplicate wells.

(7) Experimental Results

Compounds I-1, 1-4, 1-6, I-22 and RGH-188 do not lead to obviously increased number of colonies with reverse mutations at any of the tested dosages, no matter there is S9 or not in the experimental system. Ames tests for all the tested compounds are negative.

EXAMPLE 87

Bacterial reverse mutation tests for the representative compounds of □, □, and □ classes (1) The bacterial reverse mutation tests for compounds □-1, □-3, □-5, □-17, □-3, □-11, □-14, □-3, □-6, and □-11 are carried out with the method of Example 87.

(2) Experimental Results

Compounds □-1, □-3, □-5, □-17, □-3, □-11, □-14, □-3, □-6, □-11 and RGH-188 do not lead to obviously increased number of colonies with reverse mutations at any of the tested dosages, no matter there is S9 or not in the experimental system. Ames tests for all the tested compounds are negative.

The invention claimed is:

1. The benzoisothiazole compound, characterized in that it is the compound having the structure of general formula (I) or the geometric isomers, free alkalies, salts, hydrates or solvates thereof:

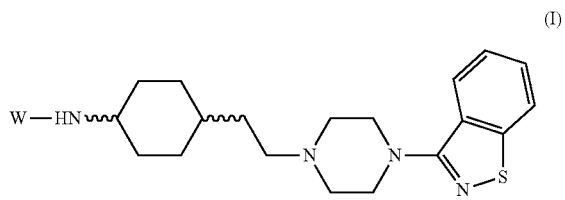

wherein:
W is:

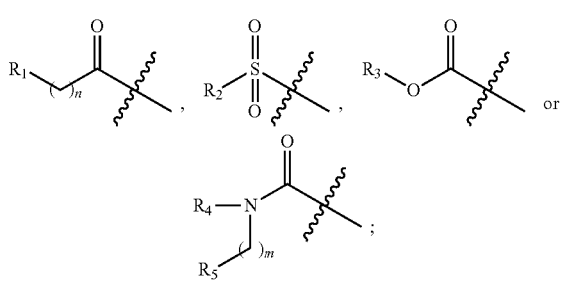

$R_1$ and $R_2$ independently represent heteroaryl or substituted heteroaryl;

n is 0, 1, 2 or 3; m is 0, 1 or 2;

$R_3$ represents $C_1$-$C_4$ alkyl, substituted $C_1$-$C_4$ alkyl, $C_3$-$C_6$ cycloalkyl, substituted $C_3$-$C_6$ cycloalkyl, phenyl, substituted phenyl, benzyl, substituted benzyl, heteroaryl, substituted heteroaryl, heteroarylmethyl, or substituted heteroarylmethyl;

$R_4$ is hydrogen atom or $C_1$-$C_4$ alkyl;

$R_5$ is phenyl, substituted phenyl, heteroaryl or substituted heteroaryl;

the heteroaryl represented by $R_1$ and $R_2$ is selected from furyl, pyrrolyl, thienyl, benzofuryl, indolyl or benzothienyl;

the substituent of the substituted heteroaryl represented by $R_1$ and $R_2$ is selected from halogen, cyano, $C_1$-$C_2$ alkyl carbonyl, nitro, methoxyl or $C_1$-$C_4$ alkyl;

the $C_1$-$C_4$ alkyl represented by $R_3$ can be substituted by 1-3 fluorine atom(s);

the substituent of the substituted cycloalkyl represented by $R_3$ is selected from $C_1$-$C_2$ alkyl;

the substituent of the substituted phenyl, substituted benzyl, substituted heteroaryl or substituted heteroarylmethyl represented by $R_3$ is selected from halogen, $C_1$-$C_2$ alkoxy, nitro or $C_1$-$C_2$ alkyl;

the heteroaryl represented by $R_3$ is selected from furyl, thienyl, pyridyl or benzofuryl;

the heteroarylmethyl represented by $R_3$ is selected from furylmethyl, thenyl, picolyl, benzofurylmethyl or benzothenyl;

the substituent of the substituted heteroaryl represented by R3 is selected from halogen, C1-C2 alkoxy, nitro or C1-C2 alkyl-substituted furyl, thienyl, pyridyl or benzofuryl;

the substituent of the substituted heteroarylmethyl represented by R3 is selected from halogen, C1-C2 alkoxy, nitro or C1-C2 alkyl-substituted furylmethyl, thenyl, picolyl, benzofurylmethyl or benzothenyl;

the heteroaryl represented by $R_5$ is selected from furyl, pyrrolyl, thienyl, pyridyl, benzofuryl, benzothienyl or indolyl; and the substituent of the substituted phenyl or substituted heteroaryl represented by $R_5$ is selected from halogen, $C_1$-$C_2$ alkoxy, nitro or $C_1$-$C_2$ alkyl.

2. The benzoisothiazole compound according to claim 1, characterized in that the hydrate is a hydrate containing 0.5-3 molecules of crystal water wherein the salt comprises a pharmaceutically acceptable anion.

3. The benzoisothiazole compound according to claim 2, characterized in that the salt further contains 0.5-6 molecules of crystal water.

4. A benzoisothiazole compound, characterized in that the compound is:

I-1 trans-N-(4-(2-(4-(benzo[d]isothiazol-3-yl)piperazin-1-yl)ethyl) cyclohexyl)furyl-2-carboxamide, I-2 trans-N-(4-(2-(4-(benzo[d]isothiazol-3-yl)piperazin-1-yl)ethyl) cyclohexyl)thienyl-2-carboxamide, I-3 trans-N-(4-(2-(4-(benzo[d]isothiazol-3-yl)piperazin-1-yl)ethyl) cyclohexyl)-1H-pyrrolyl-2-carboxamide, I-4 trans-N-(4-(2-(4-(benzo[d]isothiazol-3-yl)piperazin-1-yl)ethyl) cyclohexyl)-1H-indolyl-2-carboxamide, I-5 trans-N-(4-(2-(4-(benzo[d]isothiazol-3-yl)piperazin-1-yl)ethyl) cyclohexyl)benzofuryl-2-carboxamide, I-6 trans-N-(4-(2-(4-(benzo[d]isothiazol-3-yl)piperazin-1-yl)ethyl) cyclohexyl)benzo[b]thienyl-2-carboxamide, I-7 trans-N-(4-(2-(4-(benzo[d]isothiazol-3-yl)piperazin-1-yl)ethyl) cyclohexyl)-5-cyano-furyl-2-carboxamide, I-8 trans-N-(4-(2-(4-(benzo[d]isothiazol-3-yl)piperazin-1-yl)ethyl) cyclohexyl)-3-tert-butylfuryl-2-carboxamide, I-9 trans-N-(4-(2-(4-(benzo[d]isothiazol-3-yl)piperazin-1-yl)ethyl) cyclohexyl)-5-methyl-1 H-pyrrolyl-2-carboxamide, I-10 trans 5-acetyl-N-(4-(2-(4-(benzo[d]isothiazol-3-yl) piperazin-1-yl) ethyl)cyclohexyl)furyl-2-carboxamide, I-11 trans-N-(4-(2-(4-(benzo[d]isothiazol-3-yl)piperazin-1-yl)ethyl) cyclohexyl)-3-methylthienyl-2-carboxamide, I-12 trans-N-(4-(2-(4-(benzo[d]isothiazol-3-yl)piperazin-1-yl)ethyl) cyclohexyl)-3-bromothienyl-2-carboxamide, I-13 trans-N-(4-(2-(4-(benzo[d]isothiazol-3-yl)piperazin-1-yl)ethyl) cyclohexyl)-3-methylbenzo[b]thienyl-2-carboxamide, I-14 trans-N-(4-(2-(4-(benzo[d]isothiazol-3-yl)piperazin-1-yl)ethyl) cyclohexyl)-3-chlorobenzo[b]thienyl-2-carboxamide, I-15 trans-N-(4-(2-(4-(benzo[d]isothiazol-3-yl)piperazin-1-yl)ethyl) cyclohexyl)-5-nitro-1H-indolyl-2-carboxamide, I-16 trans-N-(4-(2-(4-(benzo[d]isothiazol-3-yl)piperazin-1-yl)ethyl) cyclohexyl)-5-methoxylbenzofuryl-2-carboxamide, I-17 trans-N-(4-(2-(4-(benzo[d]isothiazol-3-yl)piperazin-1-yl)ethyl) cyclohexyl)-2-(thien-2-yl)acetamide, I-18 trans-N-(4-(2-(4-(benzo[d]isothiazol-3-yl)piperazin-1-yl)ethyl) cyclohexyl)-2-(benzofuran-3-yl)acetamide, I-19 cis-N-(4-(2-(4-(benzo[d]isothiazol-3-yl)piperazin-1-yl)ethyl) cyclohexyl)furyl-2-carboxamide, I-20 cis-N-(4-(2-(4-(benzo[d]isothiazol-3-yl)piperazin-1-yl)ethyl) cyclohexyl)thienyl-2-carboxamide, I-21 cis-N-(4-(2-(4-(benzo[d]isothiazol-3-yl)piperazin-1-yl)ethyl) cyclohexyl)-1H-pyrrolyl-2-carboxamide, I-22 cis-N-(4-(2-(4-(benzo[d]isothiazol-3-yl)piperazin-1-yl)ethyl) cyclohexyl)-1H-indolyl-2-carboxamide, I-23 cis-N-(4-(2-(4-(benzo[d]isothiazol-3-yl)piperazin-1-yl)ethyl) cyclohexyl)benzofuryl-2-carboxamide, I-24 cis-N-(4-(2-(4-(benzo[d]isothiazol-3-yl)piperazin-1-yl)ethyl) cyclohexyl)benzo[b]thienyl-2-carboxamide, II-1 trans-N-(4-(2-(4-(benzo[d]isothiazol-3-yl)piperazin-1-yl)ethyl) cyclohexyl)thienyl-2-sulfamide, II-2 trans-N-(4-(2-(4-(benzo[d]isothiazol-3-yl)piperazin-1-yl)ethyl) cyclohexyl)-1H-pyrrolyl-3-sulfamide, II-3 trans-N-(4-(2-(4-(benzo[d]isothiazol-3-yl)piperazin-1-yl)ethyl) cyclohexyl)furyl-2-sulfamide, II-4 trans-N-(4-(2-(4-(benzo[d]isothiazol-3-yl)piperazin-1-yl)ethyl) cyclohexyl)benzo[b]thienyl-2-sulfamide, II-5 trans-N-(4-(2-(4-(benzo[d]isothiazol-3-yl)piperazin-1-yl)ethyl) cyclohexyl)benzofuryl-2-sulfamide, II-6 trans-N-(4-(2-(4-(benzo[d]isothiazol-3-yl)piperazin-1-yl)ethyl) cyclohexyl)-1H-indolyl-3-sulfamide, II-7 trans-N-(4-(2-(4-(benzo[d]isothiazol-3-yl)piperazin-1-yl)ethyl) cyclohexyl)-5-cyanofuryl-2-sulfamide, II-8 trans-N-(4-(2-(4-(benzo[d]isothiazol-3-yl)piperazin-1-yl)ethyl) cyclohexyl)-5-chlorofuryl-2-sulfamide, II-9 trans-N-(4-(2-(4-(benzo[d]isothiazol-3-yl)piperazin-1-yl)ethyl) cyclohexyl)-5-methylfuryl-2-sulfamide, II-10 trans-N-(4-(2-(4-(benzo[d]isothiazol-3-yl)piperazin-1-yl)ethyl) cyclohexyl)-5-tert-butylthienyl-2-sulfamide, II-11 trans-N-(4-(2-(4-(benzo[d]isothiazol-3-yl)piperazin-1-yl)ethyl) cyclohexyl)-5-chlorobenzo[b]thienyl-2-sulfamide, II-12 trans-N-(4-(2-(4-(benzo[d]isothiazol-3-yl)piperazin-1-yl)ethyl) cyclohexyl)-5-cyanobenzo[b]thienyl-2-sulfamide, II-13 trans-N-(4-(2-(4-(benzo[d]isothiazol-3-yl)piperazin-1-yl)ethyl) cyclohexyl)-5-methylbenzo[b]thienyl-2-sulfamide, II-14 trans-N-(4-(2-(4-(benzo[d]isothiazol-3-yl)piperazin-1-yl)ethyl) cyclohexyl)-5-nitrobenzo[b]thienyl-2-sulfamide, II-15 trans-N-(4-(2-(4-(benzo[d]isothiazol-3-yl)piperazin-1-yl)ethyl) cyclohexyl)-5-methoxylbenzofuryl-2-sulfamide, II-16 cis-N-(4-(2-(4-(benzo[d]isothiazol-3-yl)piperazin-1-yl)ethyl) cyclohexyl)thienyl-2-sulfamide, II-17 cis-N-(4-(2-(4-(benzo[d]isothiazol-3-yl)piperazin-1-yl)ethyl) cyclohexyl)-1H-pyrrolyl-3-sulfamide, II-18 cis-N-(4-(2-(4-(benzo[d]isothiazol-3-yl)piperazin-1-yl)ethyl) cyclohexyl)furyl-2-sulfamide, II-19 cis-N-(4-(2-(4-(benzo[d]isothiazol-3-yl)piperazin-1-yl)ethyl) cyclohexyl)benzo[b]thienyl-2-sulfamide, II-20 cis-N-(4-(2-(4-(benzo[d]isothiazol-3-yl)piperazin-1-yl)ethyl) cyclohexyl)benzofuryl-2-sulfamide, II-21 cis-N-(4-(2-(4-(benzo[d]isothiazol-3-yl)piperazin-1-yl)ethyl) cyclohexyl)-1H-indolyl-3-sulfamide, II-22 cis-N-(4-(2-(4-(benzo[d]isothiazol-3-yl)piperazin-1-yl)ethyl) cyclohexyl)-5-methylfuryl-2-sulfamide, III-1 trans-(4-(2-(4-(benzo[d]isothiazol-3-yl)piperazin-1-yl)ethyl) cyclohexyl)methylcarbamate, III-2 trans-(4-(2-(4-(benzo[d]isothiazol-3-yl)piperazin-1-yl)ethyl) cyclohexyl)ethylcarbamate, III-3 trans-N-(4-(2-(4-(benzo[d]isothiazol-3-yl)piperazin-1-yl)ethyl) cyclohexyl)isobutylcarbamate, III-4 trans-(4-(2-(4-(benzo[d]isothiazol-3-yl)piperazin-1-yl)ethyl) cyclohexyl)cyclopropylcarbamate, III-5 trans-(4-(2-(4-(benzo[d]isothiazol-3-yl)piperazin-1-yl)ethyl) cyclohexyl)cyclohexylcarbamate, III-6 trans-(4-(2-(4-(benzo[d]isothiazol-3-yl)piperazin-1-yl)ethyl) cyclohexyl)phenylcarbamate, III-7 trans-(4-(2-(4-(benzo[d]isothiazol-3-yl)piperazin-1-yl)ethyl) cyclohexyl)-3-methoxylphenylcarbamate, III-8 trans-(4-(2-(4-(benzo[d]isothiazol-3-yl)piperazin-1-yl)ethyl) cyclohexyl)-2-methylphenylcarbamate, III-9 trans-(4-(2-(4-(benzo[d]isothiazol-3-yl)piperazin-1-yl)ethyl) cyclohexyl)-4-chlorophenylcarbamate, III-10 trans-(4-(2-(4-(benzo[d]isothiazol-3-yl)piperazin-1-yl)ethyl) cyclohexyl)-4-nitrophenylcarbamate, III-11 trans-(4-(2-(4-(benzo[d]isothiazol-3-yl)piperazin-1-yl)ethyl) cyclohexyl)benzylcarbamate, III-12 trans-(4-(2-(4-(benzo[d]isothiazol-3-yl)piperazin-1-yl)ethyl) cyclohexyl)benzofuryl-2-methylcarbamate, III-13 trans-(4-(2-(4-(benzo[d]isothiazol-3-yl)piperazin-1-yl)ethyl) cyclohexyl)thienyl-2-methylcarbamate, III-14 cis-(4-(2-(4-(benzo[d]isothiazol-3-yl)piperazin-1-yl)ethyl) cyclohexyl)methylcarbamate, III-15 cis-(4-(2-(4-(benzo[d]isothiazol-3-yl)piperazin-1-yl)ethyl) cyclohexyl)ethylcarbamate, III-16 cis-(4-(2-(4-(benzo[d]isothiazol-3-yl)piperazin-1-yl)ethyl) cyclohexyl)benzylcarbamate, IV-1 trans-1-(4-(2-(4-(benzo[d]isothiazol-3-yl)piperazin-1-yl)ethyl) cyclohexyl)-3-phenylurea, IV-2 trans-1-(4-(2-(4-(benzo[d]isothiazol-3-yl)piperazin-1-yl)ethyl) cyclohexyl)-3-phenylethylurea, IV-3 trans-1-(4-(2-(4-(benzo[d]isothiazol-3-yl)piperazin-1-yl)ethyl) cyclohexyl)-3-(pyridin-3-yl)urea, IV-4 trans-1-(4-(2-(4-(benzo[d]isothiazol-3-yl)piperazin-1-yl)ethyl) cyclohexyl)-3-(furan-2-yl)urea, IV-5 trans-1-(benzo[b]thien-2-yl)-3-(4-(2-(4-(benzo[d]isothiazol-3-yl) piperazin-1-yl)ethyl)cyclohexyl)urea, IV-6 trans-3-(4-(2-(4-(benzo[d]isothiazol-3-yl)piperazin-1-yl)ethyl) cyclohexyl)-1-methyl-1-phenylurea, IV-7 trans-3-(4-(2-(4-(benzo[d]isothiazol-3-yl)piperazin-1-yl)ethyl) cyclohexyl)-1-butyl-1-phenylurea, IV-8 trans-3-(4-(2-(4-(benzo[d]isothiazol-3-yl)piperazin-1-yl)ethyl) cyclohexyl)-1-methyl-1-(thien-2-yl)urea, IV-9 trans-1-(4-(2-(4-(benzo[d]isothiazol-3-yl)piperazin-1-yl)ethyl) cyclohexyl)-3-(3-methoxyphenyl)urea, IV-10 trans-1-(4-(2-(4-(benzo[d]isothiazol-3-yl)piperazin-1-yl)ethyl) cyclohexyl)-3-(3-nitrophenyl)urea, IV-11 trans-1-(4-(2-(4-(benzo[d]isothiazol-3-yl)piperazin-1-yl)ethyl) cyclohexyl)-3-benzylurea, IV-12 cis-1-(4-(2-(4-(benzo[d]isothiazol-3-yl)piperazin-1-yl)ethyl) cyclohexyl)-3-phenylurea, IV-13 cis-1-(4-(2-(4-(benzo[d]isothiazol-3-yl)piperazin-1-yl)ethyl) cyclohexyl)-3-benzylurea, or IV-14 cis-1-(4-(2-(4-(benzo[d]isothiazol-3-yl)piperazin-1-yl)ethyl) cyclohexyl)-3-(furan-2-yl)urea, or a geometric isomer, free alkali, salt, hydrate or solvate thereof.

5. A composition for treating schizophrenia, characterized in that the composition comprises a therapeutically effective amount of an benzoisothiazole compound according to claim 1 or one or more of the geometric isomers, free alkalies, salts, hydrates or solvates thereof and a pharmaceutically acceptable carrier.

6. A method for treating schizophrenia, which comprises administering a therapeutically effective amount of a benzoisothiazole of claim 1 to a patient in need thereof.

7. A method for treating schizophrenia, which comprises administering a therapeutically effective amount of the composition of claim 5 to a patient in need thereof.

8. An anti-schizophrenia composition comprising a benzoisothiazole compound of claim j and a pharmaceutically acceptable carrier.

9. A composition for treating schizophrenia, wherein the composition comprises a therapeutically effective amount of one of the benzoisothiazole compounds according to claim 4, or a geometric isomer, free alkali, salt, hydrate or solvate thereof, and a pharmaceutically acceptable carrier.

10. A method for treating schizophrenia, which comprises administering a therapeutically effective amount of a benzoisothiazole compound of claim 4 to a patient in need thereof.

11. A method for treating schizophrenia, which comprises administering a therapeutically effective amount of the composition of claim 9 to a patient in need thereof.

12. An anti-schizophrenia composition comprising a benzoisothiazole compound of claim 4 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 9,550,741 B2 | Page 1 of 1 |
| APPLICATION NO. | : 14/889831 | |
| DATED | : January 24, 2017 | |
| INVENTOR(S) | : Jianqi Li et al. | |

It is certified that error appears in the above-identified patent and that said Letters Patent is hereby corrected as shown below:

In the Claims

Claim 8 at Column 88, Line 42: Please change "claim j" to --claim 1--.

Signed and Sealed this
Ninth Day of May, 2017

Michelle K. Lee
*Director of the United States Patent and Trademark Office*